United States Patent
Barbachyn et al.

(10) Patent No.: US 8,420,646 B2
(45) Date of Patent: Apr. 16, 2013

(54) TRICYCLIC TETRAHYDROQUINOLINE ANTIBACTERIAL AGENTS

(75) Inventors: Michael Robert Barbachyn, Ann Arbor, MI (US); Paul Joseph Dobrowolski, Saline, MI (US); Alexander Ross Hurd, Ann Arbor, MI (US); Dennis Joseph McNamara, Ann Arbor, MI (US); John Raymond Palmer, Fishers, IN (US); Arthur Glenn Romero, Chesterfield, MO (US); J. Craig Ruble, Greenwood, IN (US); Debra Ann Sherry, Chelsea, MI (US); Lisa Marie Thomasco, Groton, CT (US); Peter Laurence Toogood, Ann Arbor, MI (US)

(73) Assignee: PAH P&U LLC, New York, NY (US)

( * ) Notice: Subject to any disclaimer, the term of this patent is extended or adjusted under 35 U.S.C. 154(b) by 0 days.

(21) Appl. No.: 12/972,921

(22) Filed: Dec. 20, 2010

(65) Prior Publication Data
US 2011/0092494 A1    Apr. 21, 2011

Related U.S. Application Data

(63) Continuation of application No. 12/549,407, filed on Aug. 28, 2009, now abandoned, and a continuation of application No. 11/715,213, filed on Mar. 7, 2007, now Pat. No. 7,605,157, which is a continuation of application No. 10/677,551, filed on Oct. 2, 2003, now Pat. No. 7,208, 490.

(60) Provisional application No. 60/457,622, filed on Mar. 26, 2003, provisional application No. 60/427,189, filed on Nov. 18, 2002, provisional application No. 60/416,685, filed on Oct. 7, 2002.

(51) Int. Cl.
| | |
|---|---|
| A61K 31/5383 | (2006.01) |
| A61K 31/527 | (2006.01) |
| C07D 498/20 | (2006.01) |
| C07D 471/20 | (2006.01) |
| C07D 498/04 | (2006.01) |

(52) U.S. Cl.
USPC ............... 514/249; 544/344; 544/231

(58) Field of Classification Search .......... 544/344, 544/231; 514/249
See application file for complete search history.

(56) References Cited

U.S. PATENT DOCUMENTS

| 5,011,860 A | 4/1991 | Blythin et al. ............. 514/861 |
| 5,847,149 A | 12/1998 | Fuss et al. ............. 548/136 |
| 7,208,490 B2 | 4/2007 | Barbachyn et al. ......... 514/230.2 |

FOREIGN PATENT DOCUMENTS

| WO | WO 0234753 | 5/2002 |
| WO | WO 03091252 | 11/2003 |
| WO | WO 2004033449 | 4/2004 |

OTHER PUBLICATIONS

Cecil Textbook of Medicine (20th Edition, vol. 2, 1996, pp. 1739-1747).*
CAS Registry No. 728036-02-0, Aug. 10, 2004, Chemical Block Ltd.
CAS Registry No. 727671-74-1, Aug. 10, 2004, Chemical Block Ltd.
CAS Registry No. 727371-95-1, Jun. 1, 2004, TimTec, Inc.
CAS Registry No. 727371-95-1, Aug. 10, 2004, Chemical Block Ltd.
CAS Registry No. 727370-63-0, Jun. 1, 2004, TimTec, Inc.
CAS Registry No. 704878-08-0, Jun. 1, 2004, TimTec, Inc.
CAS Registry No. 704878-08-0, Aug. 10, 2004, Chemical Block.
CAS Registry No. 704878-08-0, Sep. 17, 2004, Interchim.
CAS Registry No. 704878-02-4, Aug. 10, 2004, Chemical Block Ltd.
CAS Registry No. 704878-02-4, Sep. 17, 2004, Interchim.
CAS Registry No. 696658-91-0, Sep. 17, 2004, Interchim.
CAS Registry No. 696658-91-0, Aug. 10, 2004, Chemical Block Ltd.
CAS Registry No. 696630-59-8, Jan. 1, 2004, Ambinter.
CAS Registry No. 696630-59-8, Aug. 10, 2004, Chemical Block Ltd.
CAS Registry No. 696630-59-8, Sep. 17, 2004, Interchim.
CAS Registry No. 695220-71-4, Aug. 10, 2004, Chemical Block Ltd.
CAS Registry No. 695220-71-4, Sep. 17, 2004, Interchim.
CAS Registry No. 695211-59-7, Jan. 1, 2004, Ambinter.
CAS Registry No. 695211-59-7, Jun. 1, 2004, TimTec, Inc.
CAS Registry No. 695211-59-7, Aug. 10, 2004, Chemical Block Ltd.
CAS Registry No. 695211-59-7, Sep. 17, 2004, Interchim.
CAS Registry No. 695211-58-6, Jan. 1, 2004, Ambinter.
CAS Registry No. 695211-58-6, Jun. 1, 2004, TimTec, Inc.
CAS Registry No. 695211-58-6, Aug. 10, 2004, Chemical Block Ltd.
CAS Registry No. 695211-58-6, Sep. 17, 2004, Interchim.
CAS Registry No. 695202-34-7, Jan. 1, 2004, Ambinter.
CAS Registry No. 695202-34-7, Aug. 10, 2004, Chemical Block Ltd.
CAS Registry No. 695202-34-7, Sep. 17, 2004, Interchim.
CAS Registry No. 695202-34-7, Jun. 1, 2004, TimTec, Inc.
CAS Registry No. 663946-83-6, Mar. 1, 2005, SPECS.
CAS Registry No. 401608-21-7, May 18, 2005, Labo Test.

(Continued)

Primary Examiner — Kahsay T Habte
(74) Attorney, Agent, or Firm — Martha A. Gammill

(57) ABSTRACT

The present invention is directed to tricyclic tetrahydroquinoline compounds of formula I, and pharmaceutically acceptable salts thereof

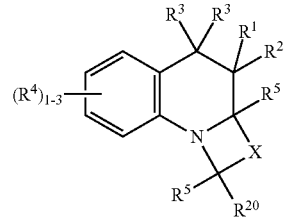

wherein the variables $R^1$, $R^2$, $R^3$, $R^4$, $R^5$, $R^{20}$ and X are as described herein and to pharmaceutical compositions thereof, that exhibit useful antibacterial activity against a wide range of human and veterinary pathogens.

27 Claims, No Drawings

OTHER PUBLICATIONS

CAS Registry No. 346630-58-8, retrieved from database 2005 Jul. 18, 2005.
CAS Registry No. 296244-43-4, Apr. 25, 2003, ChemDiv, Inc.
CAS Registry No. 296244-43-4, Aug. 11, 2003, Zelinsky Institute of Organic Chemistry.
CAS Registry No. 296244-43-4, Jan. 1, 2004, Ambinter.
CAS Registry No. 296244-43-4, Jun. 1, 2004, TimTec, Inc.
CAS Registry No. 296244-43-4, Aug. 10, 2004, Chemical Block Ltd.
CAS Registry No. 296244-43-4, Sep. 17, 2004, Interchim.
CAS Registry No. 296244-43-4, Feb. 21, 2005, AsinEx.
Declaration of Alexander R. Hurd including Exhibits I and II, Jun. 21, 2005 (exhibits I and II, 2002).
PCT International Search Report: PCT/IB 03/004389, Apr. 15, 2004.
Tiwari, et al "5-Nitro-4(2)-[Oxo-3H-Quinazolin-3-yl]-benzyideue-mailonylureas as Antibacterial Agents", J. Indian Chem Soc, 1980, pp. 1039-1040, vol. 57/100.
Beke, Gyula, et al., "Syntheis and Stereochemistry of Dispiro Substituted Pyridazines: Application of Ellipticity-Absorbance Ratio Spectra for Proving Enantiomeric Relationship by HPLC-CD/UV Detection", Chirality, 2002, vol. 14, pp. 365-371.
Csizmadia, Imre G., Journal of Molecular Structure (Theochem), 666, 2003, xii-xiv.
D'Yachenko, E. V., et al., "tert-Amino effect in heterocyclic chemistry. Synthesis of hydrogenated spiro derivatives of quinolines", Russian Chemical Bulletin, International Edition, Jun. 2004, vol. 53, No. 6, pp. 1240-1247.
Glukhareva, T. V., et al., "Synthesis of Spiro Derivatives of Pyrrolo[1,2-a]Quinoline", Chemistry of Heterocyclic Compounds, 2002, vol. 38, No. 11, pp. 1426-1427.
Karolyhazy, Laszlo, et al., "Thermochemical study on the ring closure reaction of 5-morpholino-4-vinylpyridazinones by tert-amino effect", Journal of Molecular Structure (Theochem), 2003, 666-667, pp. 667-680.
Boehm, H.-J. et al., J. Med. Chem., (2000), 43, 2664-2674.
Chen, D. K. et al., N. Engl. J Med, (1999), 341(4), 233-239.
Chopra, I. et al., JAMA (1996), 275(5), 401-403.
Database Chemcats Online, Chemical Abstracts Service, May 2003, XP002266425.
Gerlach, U. "Synthesis of Tricyclic Cyano-Substituted Tetrahydroquinolines by Radical Decyanation of Geminal Dinitriles", Tetrahedron Letters, 36(29), (1995), 5159-5162, XP004027630.
Gleave D. M. et al, "Synthesis and Antibacterial Activity of [6,5,5] and [6,6,5] Tricyclic Fused Oxazolidinones", Bioorganic & Medicinal Chemistry Letters, 8(10), May 1998. 1231-1236, XP004137053.
Kim, O. K. et al., Exp. Opin. Ther. Patents (1998), 8(8), 959-969.
Kotilainen, P. et al., J. Infect. Dis., (1990), 161, 41-44.
Maxwell, A., Trends in Microbiology (1997), 5(3), 102-109.
Maxwell, A., Mol. Microbiol., (1993), 9(4), 681-686.
Nijhuis, W. H. N. et al., "A Novel two Step Synthesis of Hexahydropyrazino[1, 2-Alphau]-quinolines", Synthesis, vol. 7, (1987), 641-645, XP002266422.
Nijuis, W. H. N. et al., Stereochemical Aspects of the tert-Amino effect, J. Org. Chem.,54(1),1998, 209-16, XP002266423.
Silver, L. L. and A. K. Bostian, Antimicrob. Agents and Chemother., Mar. 1993, 37(3), 377-383.
Trucksis, M. et al., Ann. Intern. Med. (1991), 114(5), 424-426.
Verboom, W. et al., "tert-Amino effect in Heterocyclic Synthesis" Journal of Organic Chemistry,(1984), 49(2), 269-276, XP002266421.
Groenen, L. C. et al. "The tertiary amino effect in heterocyclic synthesis: Mechanistic and computational study of the formation of six-membered rings" Tetrahedron 1988:44(14):4637-4644.
Nijhuis, W. H. N. et al., "The tert-amino effect in heterocyclic chemistry: synthesis of tetra- and pentacyclic compounds" Recl. Tray. Chem. Pays-Bas 1989:108, 172-178.
Ojea, V., et al. "Synthesis of New Heterotricyclic Compounds Containing the [1,8]Naphthyridine Group by Thermal Isomerization of 2-Dialkylamino-3-vinylpyridines" Synthesis 1991:798-802.
Ojea, V., et al. "Formation of New Heterotetracyclic Compounds by Ring Closure of 2-Amino-3-vinylpyridines" Synthesis 1992:152-157.
Richards, H. C. "Oxamniquine: A Drug for the Tropics", The Role of Organic Chemistry in Drug Research, 1985:271-289.
Schwartz, A., et al., "Applications of tert-amino effect and a nitrone-olefin 1,3-dipolar cycloaddition reaction: synthesis of novel angularly annulated diazino heterocycles" Journal of Molecular Structure (Theochem) 2000:528:49-57.
Joyeau, R., et al., "Synthesis of Benzocarbacephem and Benzocarbapenem Derivatives of Copper-promoted Intermolecular Aromatic Substitution", Chemical Society Perkin Transactions 1, 1987, pp. 1899-1907.

* cited by examiner

TRICYCLIC TETRAHYDROQUINOLINE ANTIBACTERIAL AGENTS

CROSS REFERENCE TO RELATED APPLICATIONS

This application is a continuation of U.S. patent application Ser. No. 10/677,551, filed on Oct. 2, 2003, which claims the benefit of U.S. Provisional Application Ser. No. 60/457,622, filed on Mar. 26, 2003, and U.S. Provisional Application Ser. No. 60/427,189, filed on Nov. 18, 2002, and U.S. Provisional Application 60/416,685, filed Oct. 7, 2002, all of which are incorporated herein by reference in their entireties.

TECHNICAL FIELD OF THE INVENTION

The subject invention discloses novel tetrahydroquinoline and related compounds, and pharmaceutical compositions thereof, that exhibit useful antibacterial activity against a wide range of human and veterinary pathogens, including gram-positive and gram-negative aerobic bacteria, as well as anaerobic organisms.

BACKGROUND OF THE INVENTION

The development of bacterial resistance to currently available antibacterial agents is a growing global health problem. Of particular concern are infections caused by multidrug-resistant pathogens. Such bacteria are associated with significant morbidity and mortality. A number of possible solutions to the developing bacterial resistance problem have been suggested (Silver, L. L.; Bostian, K. A. *Antimicrob. Agents Chemother.* 1993, 37, 377). Overall, the best overall solution to the bacterial resistance dilemma continues to be the identification and development of structurally novel antibacterial agents employing a unique mechanism of action (Chopra, I. et al. *JAMA*, 1996, 275, 401).

For instance, the quinolones are a widely prescribed group of bacterial DNA gyrase inhibitors. DNA gyrase is a tetrameric enzyme composed of two GyrA and two GyrB subunits that negatively supercoils DNA by a sequence of strand breaking, passage of the DNA through the interior of the enzyme complex, and resealing. The quinolines act at the GyrA subunit. Their mechanism of action involves stabilization or trapping of the cleaved gyrase-DNA complex. This inhibits the function of the essential DNA gyrase and leads to cell death. It should also be noted that the quinolones also inhibit, to varying degrees, bacterial topoisomerase IV, an essential tetrameric enzyme involved in the initiation of DNA decatenation, the process by which two daughter chromosomes are separated after division of a bacterial chromosome. Topoisomerase IV is composed of two ParC and two ParE subunits, which exhibit structural similarity to GyrA and GyrB, respectively. Representative quinolones include the fluoroquinolones ciprofloxacin, levofloxacin and gatifloxacin. Bacterial resistance to the fluoroquinolones is becoming increasingly problematic (Kotilainen, P. et al. *J. Infect. Dis.* 1990, 161, 41-44. Trucksis, M. et al. *Ann. Intern. Med.* 1991, 114, 424-426. Chen, D. K. et al. *N. Engl. J. Med.* 1999, 34, 233-239).

Bacterial DNA gyrase inhibitors that complement the activity of the quinolones by inhibiting the GyrB subunit have also been identified. The coumarins, exemplified by novobiocin and coumermycin A1, and the cyclothialidines are representative GyrB inhibitors that bind to the ATP recognition site of the subunit. Unfortunately, novobiocin has limited therapeutic value due to the observation of rapid resistance development during treatment and other limitations (Kim, O. K. et al. *Exp. Opin. Ther. Patents* 1998, 8, 959-969. Maxwell, A. *Trends in Microbiology*, 1997, 5, 102-109. Maxwell, A. *Mol. Microbiol.* 1993, 9, 681-686). The cyclothialidines suffer from drug metabolism issues (Boehm, H.-J. et al. *J. Med. Chem.* 2000, 43, 2664-2674).

SUMMARY OF THE INVENTION

In general, the invention features structurally novel tetrahydroquinolines and related compounds or pharmaceutically acceptable salts thereof, methods of their production, and their use as antibacterial agents.

In one aspect, the invention features A compound of formula I, including enantiomeric, diastereomeric, or tautomeric isomers thereof, or any pharmaceutically acceptable salt thereof;

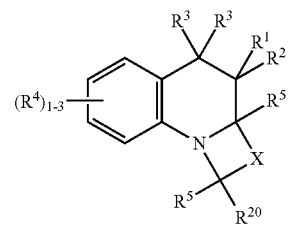

I wherein,
$R^1$ is
  (a) $R^{12}$,
  (b) $C(=O)R^6$, or
  (c) CN;
$R^2$ is
  (a) $R^{12}$,
  (b) $C(=O)R^7$,
  (c) CN,
  (d) —$CH_2$—$R^7$,
  (e) —$NR^{17}R^7$,
  (f) —$CH_2COR^7$,
  (g) —$CH_2CH_2COR^7$;
Each $R^3$ is independently
  (a) H,
  (b) $R^{12}$,
  (c) Oxo,
  (d) $C_{1-7}$ alkyl which is optionally partially unsaturated and is optionally substituted by one or more $R^{11}$,
  (e) $C_{3-8}$ cycloalkyl which is optionally partially unsaturated and is optionally substituted by one or more $R^{11}$,
  (f) aryl optionally substituted by one or more $R^8$,
  (g) heteroaryl optionally substituted by one or more $R^8$, or
  (h) halo;
Each $R^4$ is independently
  (a) H,
  (b) halo,
  (c) $OR^{12}$,
  (d) $OC(=O)NR^9R^{10}$,
  (e) $SR^{12}$,
  (f) $S(O)_mR^{13}$,
  (g) $NR^9R^{10}$,
  (h) $NR^9S(O)_mR^{13}$,
  (i) $NR^9C(=O)OR^{13}$,
  (j) phenyl optionally substituted by one or more $R^8$,
  (k) heteroaryl optionally substituted by one or more $R^8$,
  (l) cyano, (m) nitro,
(n) CONR$^9$R$^{10}$,
(o) CO$_2$R$^{12}$,
(p) C(=O)R$^{13}$,
(q) C(=NOR$^{12}$)R$^{13}$,
(r) S(O)$_m$NR$^9$R$^{10}$,
(s) NR$^9$C(=O)—R$^{12}$,
(t) C$_{1-7}$alkyl which is optionally partially unsaturated and is optionally substituted by one or more R$^{11}$,
(u) C$_{3-8}$cycloalkyl which is optionally partially unsaturated and is optionally substituted by one or more R$^{11}$,
(v) N$_3$,
(w) het$^1$ optionally substituted by one or more R$^8$, or
(x) C(O)O—C$_{1-4}$alkyl-R$^{12}$;

Each R$^5$ is independently,
(a) H,
(b) C$_{1-7}$alkyl which is optionally partially unsaturated and is optionally substituted by one or more R$^{11}$,
(c) C$_{3-8}$cycloalkyl which is optionally partially unsaturated and is optionally substituted by one or more R$^{11}$,
(d) aryl optionally substituted by one or more R$^8$, or
(e) heteroaryl optionally substituted by one or more R$^8$;

R$^6$ and R$^7$ are independently;
(a) OR$^{12}$,
(b) NR$^9$R$^{10}$,
(c) R$^{13}$, or
(e) R$^6$ and R$^7$ together with the 2 carbons to which they are attached form cyclohexane-1,3-dione optionally substituted by one or more R$^{13}$, cyclopentane-1,3-dione optionally substituted by one or more R$^{13}$, R$^6$ and R$^7$ together form —N(R$^{17}$)—S(O)$_m$—N(R$^{17}$)—, —N(R$^{17}$)—C(O)—N(R$^{17}$)—, —N(R$^{17}$)—C(S)—N(R$^{17}$)—, —N(R$^{17}$)—N(R$^{17}$)—, —N(R$^{17}$)—C(O)—, or —N(R$^{17}$)—, or R$^6$ and R$^7$ together form a phenyl ring;

R$^8$ is
(a) H,
(b) halo,
(c) OR$^{12}$,
(d) OCF$_3$,
(e) SR$^{12}$,
(f) S(O)$_m$R$^{13}$,
(g) NR$^9$R$^{10}$,
(h) NR$^9$S(O)$_m$R'3,
(i) NR$^9$C(=O)OR$^{13}$,
(j) phenyl optionally substituted by halo, cyano, C$_{1-7}$alkyl, or C$_{1-7}$alkoxy, in the alkyl portion of the C$_{1-7}$alkyl and C$_{1-7}$alkoxy is optionally substituted by one or more R$^{11}$;
(k) heteroaryl optionally substituted by halo, C$_{1-7}$alkyl, or C$_{1-7}$alkoxy,
(l) cyano,
(m) nitro,
(n) CONR$^9$R$^{10}$,
(o) CO$_2$R$^{12}$,
(p) C(=O)R$^{13}$,
(q) C(=NOR$^{12}$)R$^{13}$,
(r) S(O)$_m$NR$^9$R$^{10}$,
(s) NR$^9$C(=O)—R$^{12}$,
(t) C$_{1-7}$alkyl which is optionally partially unsaturated and is optionally substituted by one or more R$^{11}$,
(u) C$_{3-8}$cycloalkyl which is optionally partially unsaturated and is optionally substituted by one or more R$^{11}$,
(v) —C(O)H, or
(w) -het$^1$;

R$^9$ and R$^{10}$ are independently
(a) H,
(b) OR$^{12}$,
(c) aryl optionally substituted by one or more R$^{14}$,
(d) heteroaryl optionally substituted by one or more R$^{14}$,
(e) C$_{1-7}$alkyl which is optionally substituted by one or more R$^{11}$,
(f) C$_{3-8}$cycloalkyl which is optionally substituted by one or more R$^{11}$,
(g) (C=O)R$^{13}$, or
(h) R$^9$ and R$^{10}$ together with the nitrogen to which they are attached form morpholine, pyrrolidine, piperidine, thiazine, piperazine, each of the morpholine, pyrrolidine, piperidine, thiazine, piperazine being optionally substituted with R$^{11}$;

R$^{11}$ is
(a) oxo,
(b) phenyl optionally substituted by one or more R$^{14}$,
(c) OR$^{12}$,
(d) SR$^{12}$,
(e) NR$^{12}$R$^{12}$,
(f) halo,
(g) CO$_2$R$^{12}$,
(h) CONR$^{12}$R$^{12}$,
(i) C$_{1-7}$alkyl which is optionally substituted oxo, halo, OR$^{12}$, SR$^{12}$, C$_{1-7}$alkyl, or NR$^{12}$R$^{12}$ substituents, or
(j) C$_{3-8}$cycloalkyl which is optionally partially unsaturated and is optionally substituted by one or more oxo, halo, OR$^{12}$, SR$^{12}$, C$_{1-7}$alkyl, or NR$^{12}$R$^{12}$ substituents;

R$^{12}$ is
(a) H,
(b) C$_{1-7}$alkyl which is optionally partially unsaturated and is optionally substituted by oxo, halo, C$_{1-7}$alkyl, or C$_{1-7}$alkoxy substituents,
(c) C$_{3-8}$cycloalkyl which is optionally partially unsaturated and is optionally substituted by one or more oxo, halo, C$_{1-7}$alkyl, or C$_{1-7}$alkoxy substituents,
(d) aryl optionally substituted by one or more halo, C$_{1-7}$alkyl, or C$_{1-7}$alkoxy substituents, or
(e) heteroaryl optionally substituted by one or more halo, C$_{1-7}$alkyl, or C$_{1-7}$alkoxy substituents;

R$^{13}$ is
(a) C$_{1-7}$ alkyl which is optionally substituted by one or more by oxo, halo, carboxyl, C$_{1-7}$alkyl, or C$_{1-7}$alkoxy substituents,
(b) C$_{3-8}$cycloalkyl which, is optionally partially unsaturated and is optionally substituted by one or more by oxo, halo, C$_{1-7}$alkyl, or C$_{1-7}$alkoxy substituents,
(c) aryl optionally substituted by one or more halo, C$_{1-7}$alkyl, or C$_{1-7}$alkoxy substituents;
(d) heteroaryl optionally substituted by one or more halo, C$_{1-7}$alkyl, or C$_{1-7}$alkoxy substituents,
(e) —C(O)OH R$^{14}$ is
(a) H,
(b) halo,
(c) C$_{1-7}$alkyl,
(d) OR$^{12}$,
(e) OCF$_3$,
(f) SR$^{12}$,
(g) S(O)$_m$R$^{13}$,
(h) NR$^{12}$R$^{12}$,
(i) NR$^{12}$S(O)$_m$R$^{13}$,
(j) NR$^{12}$C(=O)OR$^{13}$,
(k) phenyl optionally substituted by halo, C$_{1-7}$alkyl, or C$_{1-7}$alkoxy,
(l) heteroaryl optionally substituted by halo, C$_{1-7}$alkyl, or C$_{1-7}$alkoxy,
(m) cyano,
(n) nitro,
(o) CONR$^{12}$R$^{12}$, (p) $CO_2R^{12}$,
(q) $C(=O)R^{13}$,
(r) $C(=NOR^{12})R^{13}$,
(s) $S(O)_m NR^{12}R^{12}$,
(t) $NR^9 C(=O)—R^{12}$,
(u) $C_{1-7}$alkyl which is optionally partially unsaturated and is optionally substituted by oxo, halo, $OR^{12}$, $SR^{12}$, $C_{1-7}$alkyl, or $NR^{12}R^{12}$ substituents, or
(v) $C_{3-8}$cycloalkyl which is optionally partially unsaturated and is optionally substituted by oxo, halo, $OR^{12}$, $SR^{12}$, $C_{1-7}$alkyl, or $NR^{12}R^{12}$ substituents;

X is
(a) $—(C(R^{15})_2)_n—$,
(b) $—(C(R^{15})_2)_m—O—(C(R^{15})_2)_k—$
(c) $—(C(R^{15})_2)_m—S(O)_m—(C(R^{15})_2)_k—$, or
(d) $—(C(R^{15})_2)_m—NR^{16}—(C(R^{15})_2)_k—$;

Each $R^{15}$ is independently
(a) H,
(b) $OR^{11}$,
(c) Oxo,
(d) $C_{1-7}$ alkyl which is optionally substituted by one or more by one or more $R^{11}$ substituents,
(e) $C_{3-8}$cycloalkyl which is optionally partially unsaturated and is optionally substituted by one or more by one or more $R^{11}$ substituents,
(f) aryl optionally substituted by one or more $R^8$, or
(g) heteroaryl optionally substituted by one or more $R^8$;

$R^{16}$ is
(a) H
(b) $OR^{12}$,
(c) $(C=O)R^{13}$,
(d) $(C=O)OR^{13}$,
(e) $(C=O)NR^9R^{10}$,
(f) $S(O)_m R^{13}$,
(g) $S(O)_m NR^9R^{10}$,
(h) $C_{1-7}$ alkyl which is optionally substituted by one or more $R^{11}$ substituents,
(i) $C_{3-8}$cycloalkyl which is optionally partially unsaturated and is optionally substituted by one or more $R^{11}$ substituents,
(j) aryl optionally substituted by one or more $R^8$, or
(k) heteroaryl optionally substituted by one or more $R^8$;

$R^{17}$ is
(a) H,
(b) —OH, and
(c) $C_{1-4}$alkyl;

$R^{19}$ is
(a) H,
(b) $OR^{11}$,
(c) Oxo,
(d) $C_{1-7}$ alkyl which is optionally substituted by one or more by one or more $R^{11}$ substituents,
(e) $C_{3-8}$cycloalkyl which is optionally partially unsaturated and is optionally substituted by one or more by one or more $R^{11}$ substituents,
(f) aryl optionally substituted by one or more $R^8$, or
(g) heteroaryl optionally substituted by one or more $R^8$;

$R^{20}$ is
(a) H,
(b) $C_{1-7}$alkyl which is optionally partially unsaturated and is optionally substituted by one or more $R^H$,
(c) $C_{3-8}$cycloalkyl which is optionally partially unsaturated and is optionally substituted by one or more $R^H$,
(d) aryl optionally substituted by one or more $R^8$,
(e) heteroaryl optionally substituted by one or more $R^8$, or
(f) $R^{20}$ and $R^{19}$, taken together, form $—CH_2—$;

wherein, "aryl" denotes a phenyl radical or an ortho-fused bicyclic carbocyclic radical having about nine to ten ring atoms in which at least one ring is aromatic;

wherein, "heteroaryl" encompasses a radical attached via a ring carbon or ring nitrogen of a monocyclic aromatic ring containing five or six ring atoms consisting of carbon and 1, 2, 3, or 4 heteroatoms, selected from oxygen (—O—), sulfur (—S—), oxygenated sulfur such as sulfinyl (S=O) and sulfonyl (S(=O)_2), or nitrogen N(Z) wherein Z is absent or is H, O, $C_{1-4}$alkyl, phenyl or benzyl, or a radical of an ortho-fused bicyclic heterocycle of about eight to ten ring atoms derived therefrom;

$het^1$ is a C- or N-linked five- (5), six- (6), seven- (7), or eight- (8) membered mono- or bicyclic ring, each mono- or bicyclic ring being fully saturated or partially unsaturated, and having 1-4 heteroatoms selected from the group consisting of oxygen, sulfur, and nitrogen; $het^1$ being optionally substituted by 1-2 substituents selected from $C_1$-$C_4$alkyl, amino, $C_1$-$C_4$alkylamino, $C_1$-$C_4$alkyloxy, halogen —CN, =O, =S;

each k is independently 0, 1, or 2;
each m is independently 0, 1, or 2;
each n is independently 1, 2, or 3; and
provided that
when each $R_4$ is H, that $R_1$ and $R_2$ are not simultaneously H, CN, or —C(O)—$OCH_3$ or that $R_1$ is not CN and $R_2$ is not —C(O)—$OC_{1-4}$alkyl;

when the compound is 1,2,4,4a-Tetrahydro-cis-2,4-dimethyl-8-nitrospiro[[1,4]oxazino[4,3-a]quinoline-5(6H), 5'(2'H)-pyrimidine]-2',4',6'(1'H,3'H)-trione that the compound is enantiomerically enriched (−) form of (2R,4S,4aS)-2,4-dimethyl-8-nitro-1,2,4,4a-tetrahydro-2'H,6H-spiro[1,4-oxazino[4,3-a]quinoline-5,5'-pyrimidine]-2',4',6'(1'H,3'H)-trione; and the compound is not 2,3,4,4a-tetrahydro-1',3'-dimethyl-spiro[1H 1-methyl pyrazino[1,2-a]quinoline-5(6H), 5'(2'H)-pyrimidine]-2'4'6'(1'H, 3'H)-trione.

In another aspect, the invention includes methods of synthesizing compounds of formula I. The method includes reacting an amine of the formula III with an aldehyde or ketone substituted on an aromatic ring substituted in the ortho position with a halogen, such as fluorine (and in some cases, chlorine) (formula II) of the formula II in a polar, aprotic solvent, followed by methylenation with a compound of the formula N, and; heating the reaction in a wide variety of solvents.

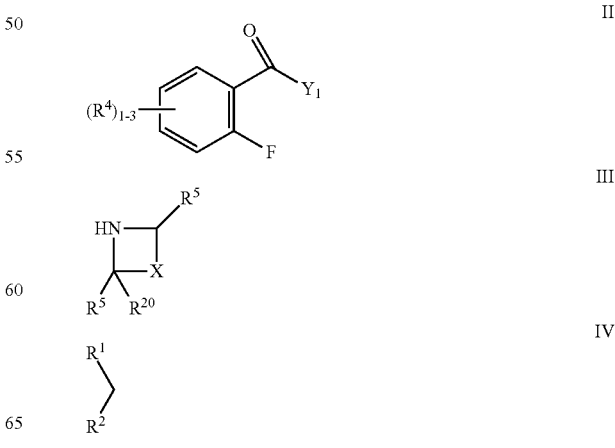

wherein, X, $R^1$, $R^2$, $R^3$, $R^4$, and $R^5$ are as defined above and $Y^1$ is H or alkyl.

Embodiments of the invention may include one or more of the following. $R^4$ is independently
(a) H,
(b) halo,
(e) $SR^{12}$,
(f) $S(O)_m R^{13}$,
(g) $NR^9 R^{10}$,
(h) $NR^9 S(O)_m R^{13}$,
(i) $NR^9 C(=O)OR^{13}$,
(j) phenyl optionally substituted by one or more $R^8$,
(k) heteroaryl optionally substituted by one or more $R^8$,
(l) cyano,
(m) nitro,
(n) $CONR^9 R^{10}$,
(o) $CO_2 R^{12}$,
(p) $C(=O)R^{13}$,
(q) $C(=NOR^{12})R^{13}$,
(s) $NR^9 C(=O)$—$R^{12}$,
(t) $C_{1-7}$alkyl which is optionally partially unsaturated and is optionally substituted by one or more $R^{11}$, or
(u) $het^1$ optionally substituted by one or more $R^8$.

For instance, $R^4$ is independently selected from $NO_2$, H, Br, F, $CF_3$, CN, $NH_2$, —C(O)—$OCH_3$, —S—$CH_3$, —S(O)$_2$—$CH_3$, —N($OCH_3$)—$CH_3$, —NH—C(O)—O-tbutyl, —NH—C(O)—$CH_3$, heteroaryl optionally substituted by one or more $R^8$, $het^1$ optionally substituted by one or more $R^8$, —S(O)$_2$—$CH_3$, or phenyl optionally substituted by one or more of $NO_2$, Cl, F, —$OCH_3$, and —$OCF_3$. $R^3$ is H. $R^1$ is —C(O)$R^6$. $R^2$ is —C(O)$R^7$. $R^6$ and $R^7$ form —$N(R^{17})$—C(O)—$N(R^{17})$— or —$N(R^{17})$—C(S)—$N(R^{17})$—. X is —$(C(R^{15})_2)_m$—O—$(C(R^{15})_2)_k$— or —$(C(R^{15})_2)_m$—$NR^{16}$—$(C(R^{15})_2)_k$—. X is —$C(R^{15})_2$—O—$C(R^{15})_2$— or —$C(R^{15})_2$—$NR^{16}$—$C(R^{15})_2$—. $R^{15}$ is independently H, $C_{1-7}$ alkyl optionally substituted by one or more $R^{11}$ substituents. X is —C(H)($C_{1-4}$alkyl)-O—C(H)($C_{1-4}$alkyl)- or —C(H)($C_{1-4}$ alkyl)-$NR^{16}$—C(H)($C_{1-4}$ alkyl)-. The compound of the formula

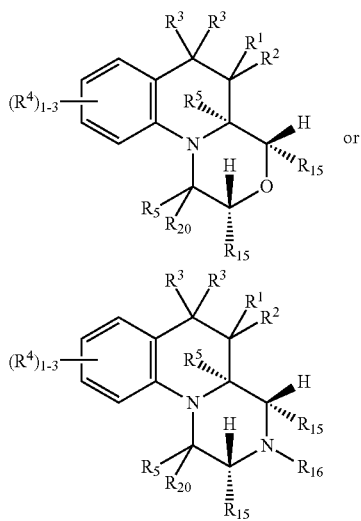

and each $R_{15}$ is independently (b), (c), (d), (e), (f), or (g). The compound of formula I may be, but is not limited to:

1,2,4,4a-Tetrahydro-2,4-dimethyl-8-nitrospiro[[1,4]oxazino[4,3-a]quinoline-5(6H), 5'(2'H)-pyrimidine]-2',4',6'(1'H,3'H)-trione;

1,2,4,4a-Tetrahydro-2,4-dimethylspiro[[1,4]oxazino[4,3-a]quinoline-5(6H), 5'(2'H)-pyrimidine]-2',4',6'(1'H,3'H)-trione;

8-Bromo-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

8-Fluoro-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

1,2,4,4a-Tetrahydro-2,4-dimethyl-8-trifluoromethylspiro[[1,4]oxazino]4,3-a]quinoline-5(6H), 5'(2'H)-pyrimidine]-2',4',6'(1'H,3'H)-trione;

1,1',2,3'4,4',4a, 6'-Octrahydro-2,4',6'-trioxospiro[[1,4]oxazino[4,3-a]quinoline-5(6H), 5'(2'H)-pyrimidine]-8-carbonitrile;

1,2,4,4a-Tetrahydro-2,4-dimethyl-8-carboxamidespiro[[1,4]oxazino[4,3-a]quinoline-5(6H), 5'(2'H)-pyrimidine]-2',4',6'(1'H,3'H)-trione;

1,2,4,4a-Tetrahydro-8-nitrospiro[[1,4]oxazino[4,3-a]quinoline-5(6H), 5'(2'H)-pyrimidine]-2',4',6'(1'H,3'H)-trione;

1,2,4,4a-Tetrahydro-2,4-dimethylspiro[[1,4]oxazino[4,3-a]quinoline-5(6H), 5'(2'H)-pyrimidine]-2',4',6'(1'H,3'H)-trione;

8-Bromo-1,2,4,4a-tetrahydro-2,4-dimethylspiro[[1,4]piperazino[4,3-a]quinoline-5(6H), 5'(2'H)-pyrimidine]-2',4',6'(1'H,3'H)-trione;

1,2,4,4a-Tetrahydro-1,4a-dimethyl-8-nitrospiro[[1,4]oxazino[4,3-a]quinoline-5(6H), 5'(2'H)-pyrimidine]-2',4',6'(1'H,3'H)-trione;

8-Bromo-1,2,4,4a-tetrahydro-cis-2,4-dimethylspiro[[1,4]oxazino[4,3-a]quinoline-5(6H), 5'(2'H)-pyrimidine]-4'-thioxo-2',6'(1'H,3'H)-dione;

8-Bromo-1,2,4,4a-tetrahydro-cis-2,4-dimethylspiro[[1,4]oxazino[4,3-a]quinoline-5(6H), 5'(2'H)pyrimidine]-2',4',6'(1'methyl, 3'methyl)-trione;

N-[1,1',2,3',4,4',4a,6'-Octahydro-2,4-dimethyl-2',4',6'-trioxospiro[[1,4]oxazino[4,3-a]quinolone-5(6H),5'(2'H)-pyrimidin]-8-yl]acetamide;

tert-butyl 1,1',2,3',4,4',4a,6'-Octahydro-2,4-dimethyl-2',4',6'-trioxospiro[[1,4]oxazino[4,3-a]quinolone-5(6H), 5'(2'H)-pyrimidin]-8-ylcarbamate;

8-Amino-1,2,4,4a-tetrahydro-2,4-dimethylspiro[[1,4]oxazino[4,3-a]quinolone-5(6145'(2'H)-pyrimidine]-2',4',6'(1'H,3'H)-trione monohydrochloride;

9-Bromo-1,2,4,4a-tetrahydro-2,4-dimethyl-8-nitrospiro[[1,4]oxazino[4,3-a]quinoline-5(6H), 5'(2'H)-pyrimidine]-2',4',6'(1'H,3'H)-trione;

8-Acetyl-1,2,4,4a-tetrahydro-2,4-dimethylspiro[[1,4]oxazino[4,3-a]quinoline-5(6H), 5'(2H)-pyrimidine)-2',4',6'(1'H,3'H)-trione;

8-Ethanone-O-methyloxime-1-1,2,4,4a-tetrahydro-2,4-dimethylspiro[[1,4]oxazino[4,3-a]quinoline-5(6H), 5'(2'H)-pyrimidine)-2',4',6'(1'H,3'H)-trione;

1,2,4,4a-Tetrahydro-2,4-dimethyl-8-(methylsulfonyl)spiro[[1,4]oxazino[4,3-a]quinoline-5(6H), 5'(2'H)-pyrimidine]-2',4',6'(1'H,3'H)-trione;

1,2,4,4a-Tetrahydro-2,4-dimethyl-8-(methylsulfinyl)spiro[[1,4]oxazino[4,3-a]quinoline-5(6H), 5'(2H)-pyrimidine]-2',4',6'(1'H,3'H)-trione;

1,2,4,4a-Tetrahydro-2,4-dimethyl-8-(methylthio)spiro[[1,4]oxazino[4,3-a]quinoline-5(6H), 5'(2'H)-pyrimidine]-2',4',6'(1'H,3'H)-trione;

1,2,4,4a-Tetrahydro-2,4-dimethyl-9-nitrospiro[[1,4]oxazino[4,3-a]quinoline-5(6H), 5'(2'H)-pyrimidine]-2',4',6'(1'H,3'H)-trione;

1,2,4,4a-Tetrahydro-2,4-dimethyl-8-nitrospiro[[1,4]oxazino[4,3-a]quinoline-5(6H),5'(2'H)-pyrimidine]-2',4',6'(1'methyl,3'methyl)-trione;

1,2,4,4a-Tetrahydro-2,4-dimethyl-8-nitrospiro[[1,4]oxazino[4,3-a]quinoline-5(6H), 5'(2'H)-pyrimidine]-2',4',6'(1'H, 3'methyl)-trione;

1,2,4,4a-Tetrahydro-4-methyl-8-nitrospiro[[1,4]oxazino[4,3-a]quinoline-5(6H),5'(2'H)-pyrimidine]-2',4',6'(1'H, 3'H)-trione;

1,2,4,4a-Tetrahydro-2-methyl-8-nitrospiro[[1,4]oxazino[4,3-a]quinoline-5(6H), 5'(2'H)-pyrimidine]-2',4',6'(1'H,3's)-trione;

2,3,4,4a-Tetrahydro-1',3,3'-trimethylspiro[1H-pyrazino[1,2-a]quinolinie-5(6H), 5'(2'H)-pyrimidine]-2'4',6'(1'H,3'H)-trione;

2,3,4,4a-Tetrahydro-3-methylspiro[1H-pyrazino[1,2-a]quinoline-5(6H), 5'(2'H)-pyrimidine]-2',4'6'(1'H,3'H)-trione;

1,1-Dimethylethyl 1,1'2,3',4',4a,6'-octahydro-8-nitro-2',4',6'-trioxospiro[3H-pyrazino[1,2-a]quinoline-5(6H), 5'(2'H)-pyrimidine]-3-carboxylate;

1,1-Dimethylethyl-8-cyano-1,1',2,3',4,4',4a,6'-octahydro-2',4',6'-trioxospiro[3H-pyrazino[1,2-a]quinoline-5(6H), 5'(2'H)-pyrimidine]-3-carboxylate;

1,1',2'3'4'4'a-Hexahydro-2',4'-dimethyl-1,3-dioxospiro[2H-indene-2,5'(6'H)-[1,4]oxazino[4,3-a]quinoline]-8'-carbonitrile;

1,2,4,4a-Tetrahydro-2,4-dimethyl[1,4]oxazino[4,3-a]quinoline-5,5,8(6H)-tricarbonitrile;

8-Bromo-1,2,4-4a-tetrahydro-2,4-dimethyl[1,4]oxazino[4,3-a]quinoline-5,5(6H)-dicarbonitrile;

2,3,4,4a-Tetrhydro-3-methyl-8-nitro-2'-thioxospiro[1H-pyrazino[1,2-a]quinoline-5(6H), 5'(2'H)-pyrimidine]-4',6'(1'H,3'H)-dione);

9-(4-Chlorophenyl)-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

1,2,4,4a-Tetrhydro-2,4-dimethyl-9-[4-(trifluoromethyoxy)phenyl]spiro[[1,4]oxazino[4,3-a]quinoline-5(6H), 5'(2'H)pyrimidine]-2'4'6'(1'H,3'H)-trione;

1,2,4,4a-Tetrahydro-9-(methoxyphenyl)-2,4-dimethylspiro[[1,4]oxazino[4,3-a]quinoline-5(6H), 5'(2'H)-pyrimidine]-2',4',6'(1'H,3'H)-trione;

9-(3-Chloro-4-fluorophenyl)-1,2,4,4a-tetrahydro-2,4-dimethylsprio[[1,4]oxazino[4,3-a]quinoline-5(6H), 5'(2'H)-pyrimidine]-2',4',6'(1'H,3'H)-trione;

1,2,4,4a-Tetrahydro-2,4-dimethyl-9-(3-nitrophenyl)spiro[[1,4]oxazino[4,3-a]quinoline-5(6H), 5'(2'H)-pyrimidine]-2',4',6'(1'H,3'H)trione;

1,1',2,3',4,4',4a,6'-Octahydro-2-4-dimethyl-2',4',6'-trioxospiro[[1,4]oxazino[4,3-a]quinoline-5(6H), 5(2'H)-pyrimidin]-9-yl]benzonitrile;

1,2,4,4a-Tetrahydro-2,4-dimethyl-9-[4-(methylsulfonyl)phenyl]spiro[[1,4]oxazino[4,3-a]quinoline-5(6H), 5'(2'H)-pyrimidine]-2',4',6'(1'H,3'H)-trione;

1,2,4,4a-Tetrahydro-2,4-dimethyl-9-(4-pyridinyl)spiro[[1,4]oxazino[4,3-a]quinoline-5(6H), 5'(2'H)-pyrimidine]-2',4',6'('H,3'H)-trione;

Methyl-1,1'-2,3',4,4a,6'-Octahydro-2,4-dimethyl-2',4',6'-trioxospiro[[1,4]oxazino[4,3-a]quinoline-5(6H), 5'(2'H)-pyrimidine]-9-carboxylate;

Methyl-1,1'-2,3',4,4a,6'-Octahydro-2,4-dimethyl-2',4',6'-trioxospiro[[1,4]oxazino[4,3-a]quinoline-5(6H), 5'(2'H)-pyrimidine]-8-carboxylate;

1,2,3,3',4,4',4a,6'-Octahydro-2',4',6'-trioxospiro[1H-pyrazino[1,2-a]quinoline-5(6H), 5'(2'H)-pyrimidine-8-carbonitrile monohydrochloride; and 2,3,4,4a-Tetrahydro-8-nitrospiro[1H-pyrazino[1,2-a]quinoline-5(6H), 5'(2'H)-pyrimidine]-2',4',6'(1'H,3'H)-trione monohydrochloride.

Other compounds of the invention include (2S,4R,4aR)-4-isopropyl-2-methyl-8-nitro-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-2,4-diethyl-8-nitro-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-2,4-dimethyl-8-nitro-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-8-acetyl-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'1)-trione;

(2R,4S,4aS)-10-fluoro-2,4-dimethyl-8-nitro-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-2,4-dimethyl-8-[5-(trifluoromethyl)-1,2,4-oxadiazol-3-yl]-1,2,4,4a-tetrahydro-2'H,6H-spiro[1,4-oxazino[4,3-a]quinoline-5,5'-pyrimidine]-2',4',6'(1'H,3'H)-trione;

1,2,4,4a-Tetrahydro-2,4-dimethyl-8-nitrospiro[[1,4]oxazino[4,3-a]quinoline-5(6H), 5'(2'H)-pyrimidine]-2',4',6'(1'H, 3'H)-trione;

(2S,4R,4aR)-2-isopropyl-4-methyl-8-nitro-1,2,4,4a-tetrahydro-2'H,6H-spiro[1,4-oxazino[4,3-a]quinoline-5,5'-pyrimidine]-2',4',6'(1'H,3'H)-trione;

(2S,4R,4aR)-2-isopropyl-4-methyl-8-nitro-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-2,4-diisopropyl-8-nitro-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-2,4-dimethyl-8-(3-methyl-1,2,4-oxadiazol-5-yl)-1,2,4,4a-tetrahydro-2'H,6H-spiro[1,4-oxazino[4,3-a]quinoline-5,5'-pyrimidine]-2',4',6'(1'H,3'H)-trione;

(2S,4R,4aR)-8-acetyl-10-fluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione;

(2'R,4'S,4a'S)-2',4'-dimethyl-8'-nitro-1',2',4',4a'-tetrahydro-2H,6'-spiro[pyrimidine-5,5'-[1,4]thiazino[4,3-a]quinoline]-2,4,6(1H,3H)-trione;

8-bromo-2,4-dimethyl-10-nitro-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-2,4-dimethyl-8-(5-methyl-1,2,4-oxadiazol-3-yl)-1,2,4,4a-tetrahydro-2'H,6H-spiro[1,4-oxazino[4,3-a]quinoline-5,5'-pyrimidine]-2',4',6'(1'H,3'H)-trione;

(2S,4S,4aS)-4-methyl-8-nitro-2-(trifluoromethyl)-1,2,4,4a-tetrahydro-2'H,6H-spiro[1,4-oxazino[4,3-a]quinoline-5,5'-pyrimidine]-2',4',6'(1'H,3'H)-trione;

4-azido-3-iodobenzyl (2R,4S,4aS)-2,4-dimethyl-2',4',6'-trioxo-1,1',2,3',4,4',4a,6'-octahydro-2'H,6H-spiro[1,4-oxazino[4,3-a]quinoline-5,5'-pyrimidine]-8-carboxylate;

(2S,4S,4aS)-2,4-dimethyl-8-nitro-1,2,4,4a-tetrahydro-2'H,6H-spiro[1,4-oxazino[4,3-a]quinoline-5,5'-pyrimidine]-2',4',6'(1'H,3'H)-trione. Other specific compounds of formula I include rel-(2R,4S,4aS)-1,2,4,4a-Tetrahydro-2-methyl-4-(1-methylethyl)-8-nitrospiro[[1,4]oxazino[4,3-a]quinoline-5(6H), 5'(2'H)-pyrimidine]-2',4',6'(1'H,3'H)-trione;

rel-(2R,4R,4aR)-1,2,4,4a-Tetrahydro-4-(1-methylethyl)-8-nitro-2-(trifluoromethyl) spiro[[1,4]oxazino[4,3-c]quinoline-5(6H), 5'(2'H)-pyrimidine]-2',4',6'(1'H,3'H)-trione;

rel-(2R,4S,4aS)-4-Ethyl-1,2,4,4a-tetrahydro-2-methyl-8-nitrospiro[[1,4]oxazino[4,3-a]quinoline-5(6H), 5'(2'H)-pyrimidine]-2',4',6'(1'H,3'H)-trione;

rel-(2R,4S,4aS)-2,4-Diethyl-1,2,4,4a-tetrahydro-8-nitrospiro[[1,4]oxazino[4,3-a]quinoline-5(6H), 5'(2'H)-pyrimidine]-2',4',6'(1'H,3'H)-trione;

(2R,4S,4aS)-1,2,4,4a-Tetrahydro-2,4-dimethyl-8-nitrospiro[[1,4]oxazino[4,3-a]quinoline-5(6H),5'(2'H)-pyrimidine]-2',4',6'(1'H,3'H)-trione;

(2S,4S,4aS)-4-Ethyl-1,2,4,4a-tetrahydro-8-nitro-2-(trifluoromethyl) spiro[[1,4]oxazino[4,3-a]quinoline-5(6H),5'(2'H)-pyrimidine]-2',4',6'(1'H,3'H)-trione;

rel-(2R,4S,4aS)-8-Acetyl-9,10-difluoro-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

rel-(2R,4S,4aS)-10-Fluoro-1,2,4,4a-tetrahydro-2,4-dimethyl-8-nitrospiro[[1,4]oxazino[4,3-a]quinoline-5(6H), 5'(2'H)-pyrimidine]-2',4',6'(1'H,3'H)-trione;

rel-(2R,4S,4aS)-1,2,4,4a-Tetrahydro-2,4-dimethyl-8-[5-(trifluoromethyl)-1,2,4-oxadiazol-3-yl]spiro[[1,4]oxazino[4,3-a]quinoline-5(6H), 5'(2'H)-pyrimidine]-2',4',6'(1'H,3'H)-trione;

rel-(2R,4S,4aS)-1,2,4,4a-Tetrahydro-2,4-dimethyl-8-nitrospiro[[1,4]oxazino[4,3-a]quinoline-5(6H), 5'(2'H)-pyrimidine]-2',4',6'(1'H,3'H)-trione;

rel-(2R,4S,4aS)-1,2,4,4a-Tetrahydro-4-methyl-2-(1-methylethyl)-8-nitrospiro[[1,4]oxazino[4,3-a]quinoline-5(6H), 5'(2'H)-pyrimidine]-2',4',6'(1'H,3'H)-trione;

rel-(2R,4R,4aR)-4-Ethyl-1,2,4,4a-tetrahydro-8-nitro-2-(trifluoromethyl) spiro[[1,4]oxazino[4,3-a]quinoline-5(6H), 5'(2'H)-pyrimidine]-2',4',6'(1'H,3'H)-trione;

rel-(2R,4S,4aS)-2,3,4,4a-Tetrahydro-2,4-dimethyl-8-nitrospiro[1H-benzo[c]quinolizine-5(6H), 5'(2'H)-pyrimidine]-2',4',6'(1'H,3'H)-trione;

rel-(2R,4S,4aS)-1,2,4,4a-Tetrahydro-2,4-bis(1-methylethyl)-8-nitrospiro[[1,4]oxazino[4,3-a]quinoline-5(6H),5'(2'H)-pyrimidine]-2',4',6'(1'H,3'H)-trione;

rel-(2R,4S,4aS)-8-[5-(Difluoromethyl)-1,2,4-oxadiazol-3-yl]-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

rel-(2R,4S,4aS)-1,2,4,4a-Tetrahydro-2,4-dimethyl-8-(3-methyl-1.2.4-oxadiazol-5-yl) spiro[[1,4]oxazino[4,3-a]quinoline-5(6H), 5'(2'H)-pyrimidine]-2',4',6'(1'H,3'H)-trione;

rel-(2R,4S,4aS)-8-Acetyl-10-fluoro-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

rel-(2R,4S,4aS)-2-Ethyl-1,2,4,4a-tetrahydro-4-methyl-8-nitrospiro[[1,4]oxazino[4,3-a]quinoline-5(6H), 5'(2'H)-pyrimidine]-2',4',6'(1'H,3'H)-trione;

rel-(2'R,4'S,4'aS)-1',2',4',4'a-Tetrahydro-2',4'-dimethyl-8'-nitrospiro[pyrimidine-5(2H), 5'(6'H)-[1,4]thiazino[4,3-a]quinoline]-2,4,6(1H,3H)-trione;

(2R,4S,4aS)-8-Bromo-1,2,4,4a-tetrahydro-2,4-dimethyl-10-nitrospiro[[1,4]oxazino[4,3-a]quinoline-5(6H),5'(2'H)-pyrimidine]-2',4',6'(1'H,3'H)-trione;

(2R,4S,4aS)-9,10-Difluoro-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

rel-(2R,4S,4aS)-1,2,4,4a-Tetrahydro-2,4-dimethyl-8-(1,2,4-oxadiazol-3-yl) spiro[[1,4]oxazino[4,3-a]quinoline-5(6H), 5'(2'H)-pyrimidine]-2',4',6'(1'H,3'H)-trione;

rel-(2R,4S,4aS)-8-(5-Cyclopropyl-1,2,4-oxadiazol-3-yl)-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione;

rel-(2R,4S,4aS)-2-Ethenyl-1,2,4,4a-tetrahydro-4-methyl-8-nitrospiro[[1,4]oxazino[4,3-a]quinoline-5(6H), 5'(2'H)-pyrimidine]-2',4',6'(1'H,3'H)-trione;

rel-4-[3-[(2R,4S,4aS)-1,1',2,3',4,4',4a,6'-Octahydro-2,4-dimethyl-2',4',6'-trioxospiro[[1,4]oxazino[4,3-c]quinoline-5(6H), 5'(2'H)-pyrimidin]-8-yl]-1,2,4-oxadiazol-5-yl]benzonitrile;

rel-(2R,4S,4aS)-1,2,4,4a-Tetrahydro-2,4-dimethyl-8-(5-methyl-1,2,4-oxadiazol-3-yl) spiro[[1,4]oxazino[4,3-a]quinoline-5(6H), 5'(2'H)-pyrimidine]-2',4',6'(1'H,3'H)-trione;

rel-(2R,4S,4aS)-1,2,4,4a-Tetrahydro-4-methyl-8-nitro-2-propylspiro[[1,4]oxazino[4,3-a]quinoline-5(6H), 5'(2'H)-pyrimidine]-2',4',6'(1'H,3'H)-trione;

rel-(2R,4S,4aS)-2-Cyclopropyl-1,2,4,4a-tetrahydro-4-methyl-8-nitrospiro[[1,4]oxazino[4,3-a]quinoline-5(6H), 5'(2'H)-pyrimidine]-2',4',6'(1'H,3'H)-trione;

(2S,4S,4aS)-1,2,4,4a-Tetrahydro-2,4-dimethyl-8-nitrospiro[[1,4]oxazino[4,3-a]quinoline-5(6H), 5'(2'H)-pyrimidine]-2',4',6'(1'H,3'H)-trione;

rel-(2R,4S,4aS)-1,2,4,4a-Tetrahydro-2,4-dimethyl-8-[5-(methylthio)-1,3,4-thiadiazol-2-yl]spiro[[1,4]oxazino[4,3-a]quinoline-5(6H), 5'(2'H)-pyrimidine]-2',4',6'(1'H,3'H)-trione;

rel-(2R,4R,4aR)-1,2,4,4a-Tetrahydro-4-methyl-8-nitro-2-(trifluoromethyl) spiro[[1,4]oxazino[4,3-a]quinoline-5(6H), 5'(2'H)-pyrimidine]-2',4',6'(1'H,3'H)-trione; and rel-(4-Azido-3-iodophenyl)methyl (2R,4S,4aS)-1,1',2,3',4,4',4a,6'-octahydro-2,4-dimethyl-2',4',6'-trioxospiro[[1,4]oxazino[4,3-a]quinoline-5(6H), 5'(2'H)-pyrimidine]-8-carboxylate The aforementioned embodiments encompass all stereoisomeric forms, e.g., enantiomeric, diastereomeric, and tautomeric, of the named compounds.

The compounds of Formula I include at least one chiral center. Formula I covers both racemic and enantiomerically enriched forms of the compound of this invention. The racemic mixture is useful in the same way and for the same purpose as the more active enantiomer; the difference is that more of the racemic material must be used to produce the same antibacterial effect. It will be apparent to one skilled in the art that some of the claimed compounds have multiple chiral centers present. In these cases, diastereomers are possible. All of these diastereomers, in racemic and enantiomerically enriched forms, are also within the scope of the compounds of Formula I.

In another aspect, the invention features a pharmaceutical composition which includes one or more compounds of formula I. The composition may include an enantiomerically enriched form of the compound of formula I. For instance, the composition may include at least 50% (more typically at least 80% or 90%, or more) of one enantiomer of a compound of formula I relative to the other enantiomer of the compound.

Advantageously and surprisingly, the compounds of this invention inhibit bacterial DNA gyrase, an ATP-dependent type II topoisomerase, in a manner distinct from that of other known DNA gyrase inhibitors such as quinolines, coumarins, and cyclothialidines.

The term alkyl refers to branched and straight chained substituents.

DESCRIPTION OF THE INVENTION

The subject invention discloses tricyclic tetrahydroquinoline topoisomerase inhibitors. Compounds of this invention inhibit bacterial DNA gyrase, a topoisomerase II. These compounds have useful activity against aerobic and anaerobic bacteria, being effective against a number of human and veterinary pathogens. Representative organisms include, but are not limited to, *Staphylococcus aureus, Staphylococcus epidermidis, Enterococcus faecalis, Enterococcus faecium, Streptococcus pneumoniae, Streptococcus pyogenes, Chlamydophila pneumoniae, Haemophilus influenzae, Moraxella catarrhalis, Escherichia coli, Klebsiella pneumoniae, Pseudomonas aeruginosa, Clostridium* spp., *Peptostreptococcus* spp. and *Bacteroides* spp. It will be apparent to one skilled in the art that the described organisms are merely representative and that other bacteria are included within the spectrum of activity of the claimed compounds.

The compound of formula I may be in the form of pharmaceutically acceptable salts. The term "pharmaceutically acceptable salts" refers to salts prepared from pharmaceutically acceptable, non-toxic bases and acids. Pharmaceutically acceptable, non-toxic bases and acids include inorganic bases, inorganic acids, organic acids, and inorganic bases. Salts derived from inorganic bases include aluminum, ammonium, calcium, ferric, ferrous, lithium, magnesium, potassium, sodium, zinc, and the like. Salts derived from pharmaceutically acceptable, organic, non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, mineral acids, sulfonic acids, phosphoric acid, phosphorous acid, and the like. Salts derived from pharmaceutically acceptable, organic, non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid. Other salts may be derived from aryl and alkyl sulfonic acids such as toluene sulfonic acids and the like.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation. The therapeutically effective amount of the compound of formula I that is administered and the dosage regimen for treating a disease condition with the compound of formula I and/or compositions containing the compound of formula I depends on a variety of factors, including the age, weight, sex and medical condition of the subject, the severity of the disease, the route and frequency of administration, and the particular compound(s) employed, and thus may vary widely. The dosage of the compound of formula I as administered to a mammal can be between about 0.001 to about 100 mg/kg of body weight/day. In general, the compound of formula I is a component of a pharmaceutical composition. Pharmaceutical compositions contain well-known carriers and excipients in addition to the compound of formula I. The pharmaceutical compositions may contain the compound of formula I in an amount in the range between about 1 to about 1000 mg, such as in the range of between about 50 to about 800 mg. Generally, the pharmaceutical composition includes between about 0.5% to about 90% by weight of the compound of formula I. A total daily dose of about 1 to 1000 mg of the compound of formula I may be appropriate for an adult. The daily dose can be administered in one to four doses per day. The desired dose may conveniently be presented in a single dose or as divided into multiple doses administered at appropriate intervals, for example, as two, three, four or more sub-doses per day. The sub-dose itself may be further divided, e.g., into a number of discrete loosely spaced administrations.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation.

Pharmaceutical compositions of the compound of formula I either individually or in combination with other antimicrobial agents, may be prepared by methods well known in the art, e.g., by means of conventional mixing, dissolving, granulation, dragee-making, levigating, emulsifying, encapsulating, entrapping, lyophilizing processes or spray drying. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

The compounds of formula I may be administered parenterally, orally, topically, transdermally, and rectally (e.g., as a suppository).

Formulations for systemic administration may be in the form of aqueous solutions and suspensions, in addition to solid tablet and capsule formulations. The aqueous solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants are well and widely known in the pharmaceutical art. For instance, the suspensions or solutions for systemic administration may include β-cyclodextrins, such as Captisol®, as a solubilizing agent. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions.

Pharmaceutical compositions for parenteral administration will generally contain a pharmaceutically acceptable amount of the compound or a soluble salt (acid addition salt or base salt) dissolved in a pharmaceutically acceptable liquid carrier such as, for example, water-for-injection and a buffer to provide a suitably buffered isotonic solution, for example, having a pH of about 3.5-6. Suitable buffering agents include, for example, trisodium orthophosphate, sodium bicarbonate, sodium citrate, N-methylglucamine, L(+)-lysine and L(+)-arginine to name but a few representative buffering agents. The compound of this invention generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage.

For systemic administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions, and the like for oral ingestion by a patient.

In addition to the compound of formula I, the pharmaceutical composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutical acceptable materials. The components pharmaceutical composition can be encapsulated or tableted for convenient administration.

For oral administration, the pharmaceutical composition may be in the form of, for example, a tablet, capsule, suspension, or liquid. If desired, other active ingredients may be included in the composition. The suspension or liquid may include other additives such as β-cyclodextrins, such as Captisol®, which may act as a solubilizing agent.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Alternatively, the compound of formula I may be in a powder form for constitution with a suitable vehicle, e.g., sterile, pyrogen-free water, before use.

For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

As a topical treatment an effective amount of Formula I is admixed in a pharmaceutically acceptable gel or cream vehicle that can be applied to the patient's skin at the area of treatment. Preparation of such creams and gels is well known in the art and can include penetration enhancers, such as oils or alcohols, which increase or permit the compounds of formula I to penetrate the dermis to transdermal tissue.

In some embodiments, the compound of formula I can be administrated by inhalation provided that the compounds pass into the blood stream. For example, pharmaceutical compositions containing the compound of formula I can be conveniently delivered through an aerosol spray in the form of solution, dry powder, or cream. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

Additionally, the compound of formula I may be delivered using a sustained-release system. Various sustained-release materials have been established and are well known by those skilled in the art. Sustained-release capsules may, depending on their chemical nature, release the compounds for 24 hours up to several days. Depending on the chemical nature and the biological stability of the therapeutic reagent, additional strategies for protein stabilization may be employed.

The compound of formula I may also be delivered by controlled-release formulation as may be provided in a dispersion of active compound in hydroxypropyl-methyl cellulose, or other methods known to those skilled in the art.

The pharmaceutical compositions also may be part of a combination therapy. In a combination therapy, the compound of formula I and other medicaments, such as other antimicrobial, anti-inflammatory, and pain relief agents, can be administered simultaneously or at separate intervals. When administered simultaneously the compound of formula I and other medicaments can be incorporated into a single pharmaceutical composition or into separate compositions, e.g., the compound of formula I, in one composition and the other medicaments in another composition. Each of these compositions may be formulated with common excipients, diluents or carriers, and compressed into tablets, or formulated elixirs or solutions. The compounds can be formulated as sustained relief dosage forms and the like.

When separately administered, therapeutically effective amounts of the compound of formula I and the other medicaments are administered on a different schedule. One may be administered before the other as long as the time between the two administrations falls within a therapeutically effective interval. A therapeutically effective interval is a period of time beginning when one of either (a) the compound of formula I or (b) the other medicaments is administered to a mammal and ending at the limit of the beneficial effect in the treatment of the combination of (a) and (b). Mixture of different compounds of formula I may also be administered simultaneously or together.

In some embodiments, the antibacterial compounds are prodrugs of the compounds of formula I. The expression "prodrug" denotes a derivative of a known direct acting drug, which is transformed into the active drug by an enzymatic or chemical process. Prodrugs of the compounds of formula I are prepared by modifying functional groups present on the compound in such a way that the modifications are cleaved, either in routine manipulation or in vivo, to the parent compound. Prodrugs include, but are not limited to, compounds of structure (I) wherein hydroxy, amine or sulfhydryl groups are bonded to any group that, when administered to the animal, cleaves to form the free hydroxyl, amino or sulihydryl group, respectively. Representative examples of prodrugs include, but are not limited to, acetate, formate and benzoate derivatives of alcohol and amine functional groups. See Notari, R. E., "Theory and Practice of Prodrug Kinetics," Methods in Enzymology, 112:309-323 (1985); Bodor, N., "Novel Approaches in Prodrug Design," Drugs of the Future, 6(3): 165-182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985).

The compounds of this invention may be synthesized by various methods known to those skilled in the art. Non-limiting examples of synthetic schemes for producing the antibacterial agents are described below.

Chart 1 shows a method of preparation of the compounds of Formula I, which are the subject of this invention. Benzaldehydes of structure 1, which are discussed below in charts 3-9, are reacted with a cyclic amine reagent 2 under a variety of reaction conditions to provide the intermediate 3. Preferred conditions include reacting 1 with 2 in a suitable solvent such as N,N-dimethylformamide (DMF), dimethyl sulfoxide (DMSO) or acetonitrile in the presence of a suitable base such as potassium carbonate, dipotassium hydrogen phosphate, N,N-diisopropylethylamine and the like and at a suitable temperature (typically 50° C. to reflux temperature) until the reaction achieves a high conversion to the desired product 3. Compound 3 can be purified by column chromatography over silica gel or by recrystallization. Alternatively, the crude material can often be used directly in the next step. To this end, compound 3 is reacted with an active methylene reagent 4 ($R^1$ and $R^2$ are both electron-withdrawing groups) in a suitable solvent, such as methanol, butanol and the like and at a suitable temperature such as ambient temperature to generate the intermediates 5. Compounds 4 are commercially available or known in the open and patent literature. For example, 1,2,6-thiadiazine-3,5(2H,6H)-dione 1,1-dioxide is described in Goya, P.; et al. *Heterocycles* 1981, 16, 5-7 and Ochoa, C.; et al. *J. Heterocycl. Chem.* 1978, 15, 221-224. N,N-dihydroxy derivatives of barbituric acid are also known: Cowden, W.; et al. *Aust. J. Chem.* 1982, 35, 795-797. Barbituric acid and thiobarbituric acid are commercially available starting materials.

Compound 5 can, in some cases, be isolated and purified. However, it is often preferable to simply continue the reaction for longer periods of time and/or at higher temperature (typically 50° C. to reflux temperature) to drive the reaction further and/or to completion to give the targeted and claimed compounds 6, which are compounds of Formula I. It will be apparent to one skilled in the art that the above synthetic description is merely representative and that additional non-essential variations known to one skilled in the art are possible, some of which are encompassed in the examples of this invention.

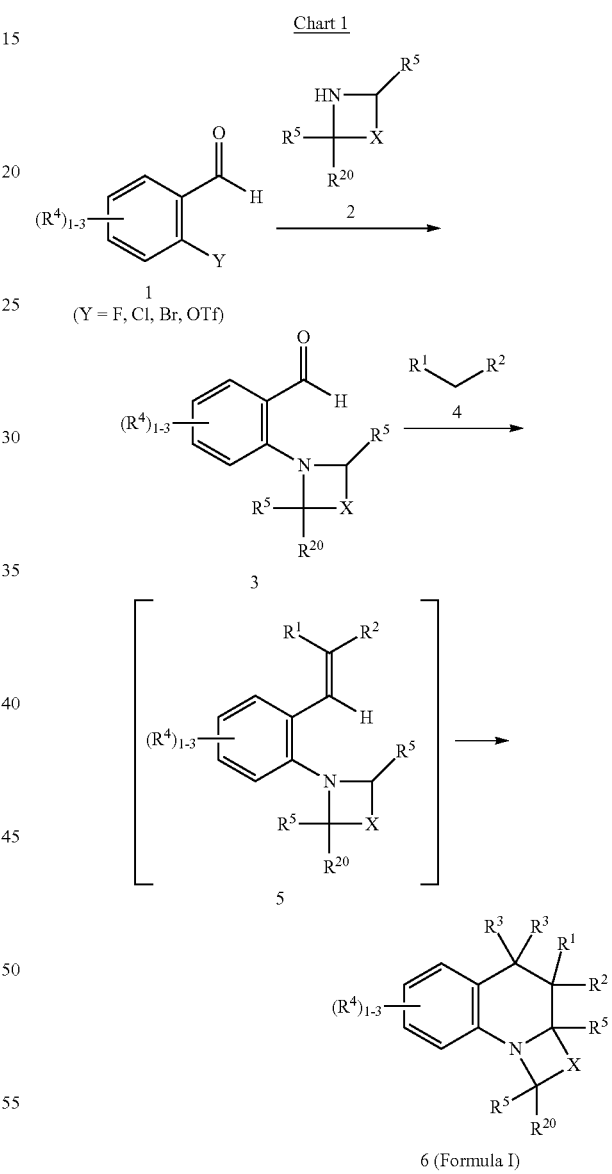

Chart 1

In the case of spirocyclic hydantoin derivatives of compounds of Formula I ($R^1$ and $R^2$ taken together to form a hydantoin ring), the desired compounds can be prepared as shown in Chart 2. The ketones 7 (see references noted below for illustrative examples) are reacted with potassium cyanide and ammonium carbonate or other synthetic equivalents described in the references below to provide the hydantoin products 8, which are compounds of Formula I, which are the subject of this invention. It will be apparent to one skilled in the art that the above synthetic description is merely representative and that additional non-essential variations known to one skilled in the art are possible, some of which are encompassed in the examples of this invention. References to this chemistry can be found in: Obrecht, D.; et al. *Helvetica Chimica Acta* 1992, 75, 1666-96, Horn, E.; et al. *Chem. Ind.* 1986, 615-16, Grunewald, G. L.; et al. *J. Med. Chem.* 1980, 23, 754-8, Denyer, C. V.; et al. *Bioorg. Med. Chem. Lett.* 1992, 2, 1039-42, and references cited within these citations.

Chart 2

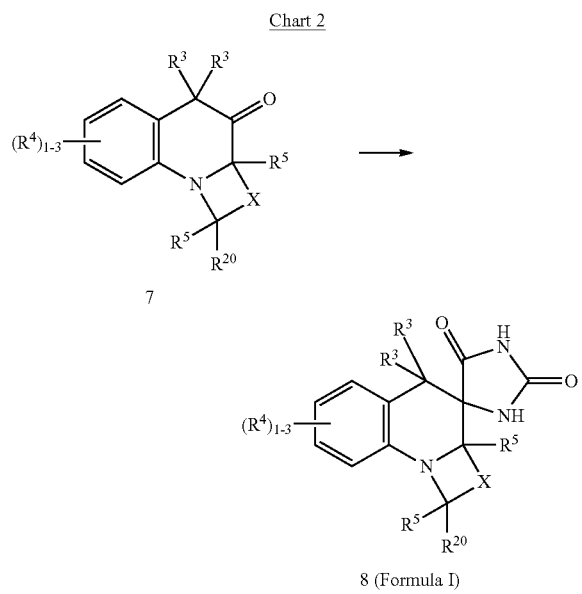

8 (Formula I)

Charts 3-9 illustrate general schemes for the synthesis of 2-halobenzaldehydes. In addition to the large number of 2-halobenzaldehydes that are available commercially, several additional 2-halobenzaldehydes may be produced by one skilled in the art by one or both of the methods shown below.

Referring to Chart 3, a 2-halotoluene may be oxidized to the 2-halobenzaldehyde with chromium trioxide, or similar oxidant, in the presence of acetic anhydride, or other acylating agent. See for example *Org. Syn., Coll. Vol.* 2, 1941, 441. The intermediate diacetate may be isolated and purified, or it may be hydrolyzed under acidic or basic conditions to the desired aldehyde. In addition to the many commercially available 2-halotoluenes that may be employed, many more may be readily prepared by electrophilic aromatic substitution reactions (Friedel Crafts acylation, nitration, chlorosulfonation, etc) starting from 2-fluorotoluene. All four regioisomers of the products may be formed, in varying amounts, from these electrophilic aromatic substitution reactions.

CHART 3: Synthesis of 2-halobenzaldehydes via oxidation

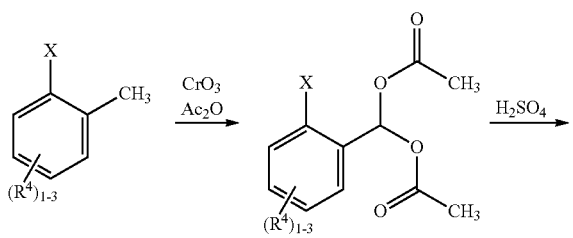

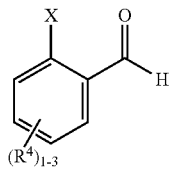

Referring to chart 4, a fluorobenzene may be lithiated with lithium diisopropylamide, or another appropriate base, and the lithium salt may be trapped with dimethylformamide, or another appropriate electrophile, to yield the desired aldehyde.

CHART 4: Synthesis of 2-fluorobenzaldehydes via lithiation

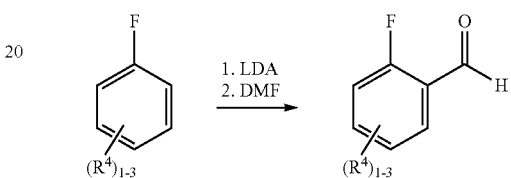

In many cases where the above methods are not appropriate for the synthesis of the requisite aldehydes, they may be made from the corresponding bromofluorobenzaldehydes as shown in Chart 5. The aldehyde is first protected by acetalization with an appropriate 1,2-diol in the presence of an appropriate acid. The resulting compound is then treated with an appropriate metal reagent such as n-BuLi or Mg. The resulting anion is quenched with the appropriate electrophile, and the aldehyde is deprotected with aqueous acid. A range of electrophiles including Weinreb amides, aldehydes, ketones, and disulfides may be used.

CHART 5: Bromofluorobenzaldehydes

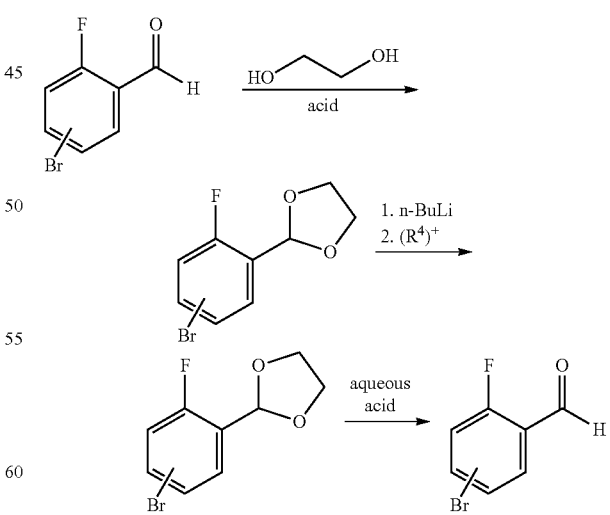

The requisite 4-Bromo-2-fluorobenzaldehyde and 5-bromo-2-fluorobenzaldehyde are commercially available from Aldrich Chemical Company as well as other suppliers. 2-Bromo-6-fluorobenzaldehyde may be made according to Chart 3 starting from commercial 2-bromo-6-fluorotoluene. 3-Bromo-2-fluorobenzaldehyde may be made according to Chart 4 starting from 2-fluorobromobenzene.

In some cases, it may be advisable to introduce the amino substituent before introducing the electrophile-derived substituent, as shown in Chart 6. The appropriate bromo-2-fluorobenzaldehyde is treated with the desired amine in the presence of an appropriate base such as potassium carbonate. The 2-amino-bromo-benzaldehyde is then protected by acetalization with an appropriate 1,2-diol in the presence of an appropriate acid. The resulting compound is then treated with an appropriate metal reagent such as n-BuLi or Mg. The resulting anion is quenched with the appropriate electrophile, and the aldehyde is deprotected with aqueous acid. A range of electrophiles including Weinreb amides, aldehydes, ketones, and disulfides may be used.

CHART 6:

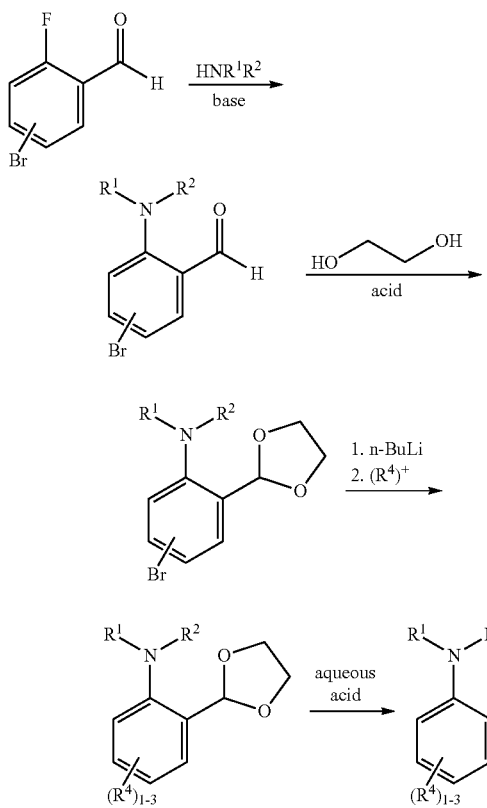

Chart 7: Reduction Reactions

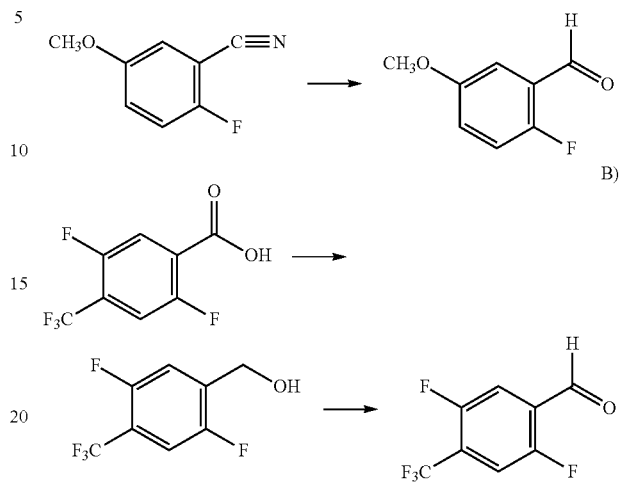

Formylation of fluoroarenes is shown in Chart 8. Formylation of fluoroarenes can be accomplished by either (a) direct metallation of the ortho position followed by trapping with DMF, see *Tetrahedron Lett.* 1992, 33, 7499, and similar routes in *Bioorganic & Medicinal Chemistry*, 1993, 6, 403, and *J. Org. Chem.* 1988, 53, 3145-7; (b) metal-halogen exchange followed by trapping with DMF, such as described in *Perkin* 1, 2000, 24, 4234; (c) Lewis acid catalyzed formylation, see *J. Med. Chem.*, 1988, 31, 1972-7 and *J. Org. Chem.*, 1986, 51 4073-5; or by (d) Vilsmer-type formylation, see *J. Med. Chem.*, 1986, 29, 2250.

Chart 8: Formylation of fluoroarenes

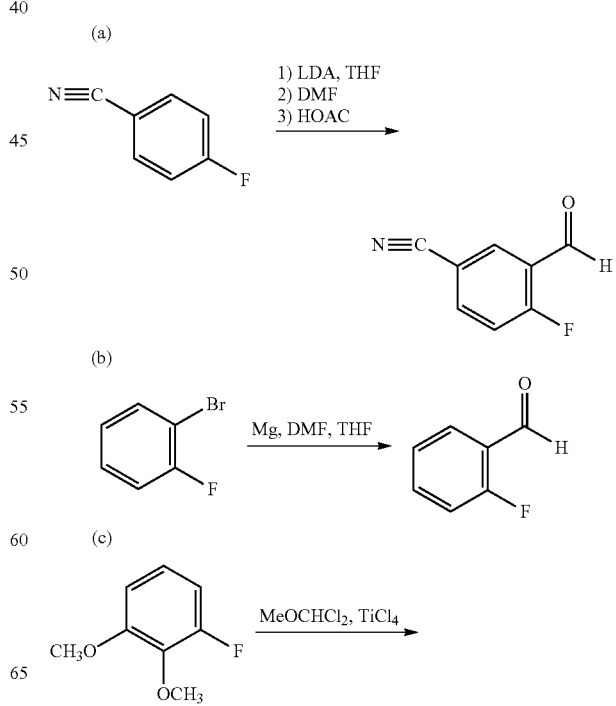

In Chart 7, the desired benzaldehyde is formed by reduction and oxidation reactions. For instance, o-fluoroaryl nitriles are reduced to the desired aldehydes (See A) by the methods described in Milos Hudlicky, "Reduction in organic chemistry, ACS Monograph 188," $2^{nd}$ ed. 1996, p 239. Alternatively, o-fluorocarboxylic acid or the ester moiety is reduced to the corresponding alcohol as described (Hudlicky, 1996), and then oxidation to the desired aldehyde (See B) by one of many methods described in Milos Hudlicky, "Oxidation in organic chemistry, ACS Monograph 186." 1990, 115-118, 123-126.

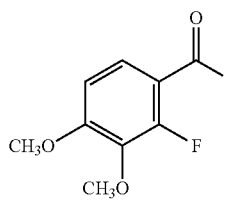

(d)

Chart 9, refers to methods for preparing Aryl, vinyl and amino substituted o-fluorobenzaldehydes, such as 1) aryl-aryl palladium couplings described by N. Miyaura and A. Suzuki in "Palladium-catalyzed cross coupling reactions of organoboron compounds." *Chem. Rev.,* 1995, 95, 2457-83; 2) aryl-amino couplings described by Buchwald, et. al. in *J. Am. Chem. Soc.,* 1994, 116, 7901, *J. Am. Chem. Soc.,* 1996, 118, 7215, or *Acc. Chem. Res.* 1998, 805, or by Hartwig, et. al in *J. Am. Chem. Soc.,* 1994, 116, 5969; 3) aryl-vinyl couplings (Heck reaction) described in *Angew. Chem., Int. Ed. Eng.* 1995, 34, 1844, 1848 or *Tetrahedron Lett.* 1996, 37, 6535; or 4) aryl-CO bond formation described in *Tetrahedron. Lett.* 1986, 27, 3931.

Chart 9: Aryl, vinyl and amino substituted o-fluorobenzaldehydes 1) aryl-aryl palladium couplings

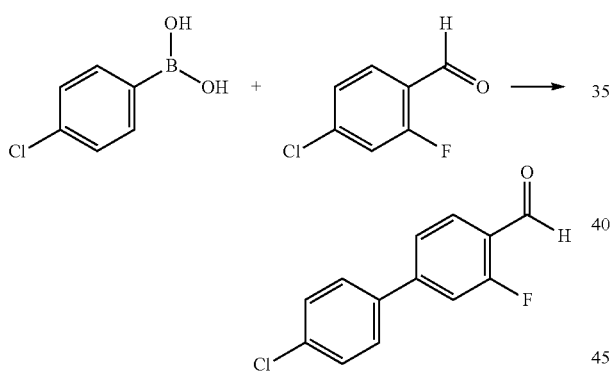

2) aryl-aryl couplings:

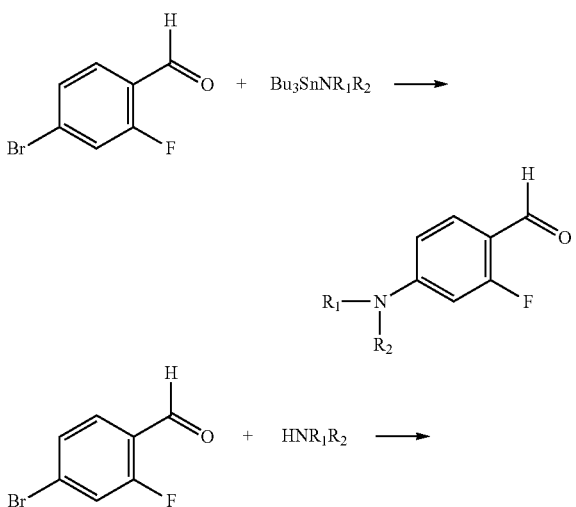

3) aryl-vinyl couplings (Heck reaction):

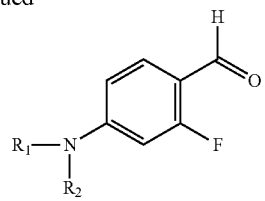

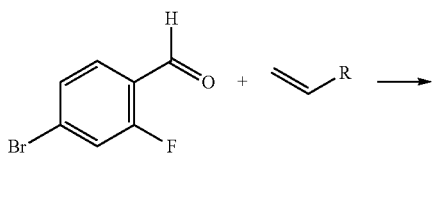

4) aryl-CO bond formation:

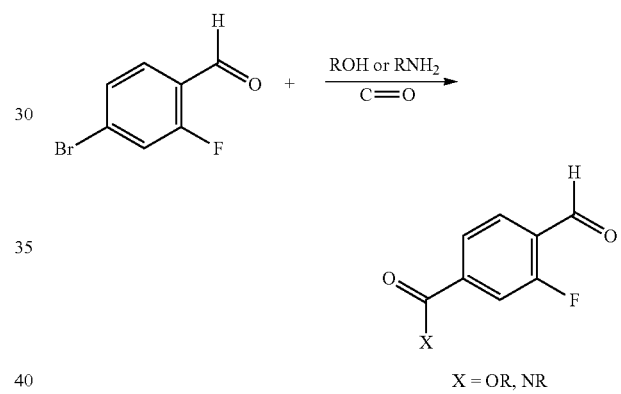

X = OR, NR

The compounds of Formula I include at least one chiral center. Formula I covers both racemic and enantiomerically enriched forms of the compound of this invention. The racemic mixture is useful in the same way and for the same purpose as the more active enantiomer; the difference is that more of the racemic material must be used to produce the same antibacterial effect. It will be apparent to one skilled in the art that some of the claimed compounds have multiple chiral centers present. In these cases, diastereomers are possible. All of these diastereomers, in racemic and enantiomerically enriched forms, are also within the scope of the claimed compounds of Formula I.

The term "enantiomerically enriched" means that one enantiomer of a specific compound is present in a mixture of the enantiomers for that compound at a greater amount relative to the other enantiomer. For instance, an enantiomerically enriched form may include a mixture of enantiomers of a specific compound in which the concentration of a single enantiomer of that compound is greater than 50%, more typically greater than 60%, 70%, 80%, or 90%, or higher, relative to the other enantiomer of that compound.

Racemic examples of compounds of Formula I can be separated into individual enantiomers or enantiomerically enriched isomers by high-pressure liquid chromatography (HPLC) over various chiral stationary phases. For example, chromatography of racemic material over a ChiralPack AD column with ethanol (0.1% DEA) or ethanol/isopropanol (0.1% DEA) affords enantiomerically enriched material. Alternatively, racemic compounds can be separated into enantiomerically enriched isomers by preparative HPLC using a Chirose C3 column and ethanol/isopropanol (0.1% DEA). It should be noted that these are merely representative conditions and that other mobile and stationary phases are useful for providing enantiomerically enriched compounds of Formula I.

Alternatively, enantiomerically enriched compounds of Formula I can be prepared by starting with enantiomerically enriched cyclic amines 2 (see Chart 1).

Also, enantiomerically enriched compounds of Formula I can be prepared by crystallization of racemic mixtures in the presence of an enantiomerically enriched acid or base to make a diastereomeric salt.

Without further elaboration, it is believed that one skilled in the art can, using the preceding description, practice the present invention to its fullest extent. The foregoing detailed description is given for clearness of understanding only, and no unnecessary limitations should be understood therefrom, as modifications within the scope of the invention may become apparent to those skilled in the art.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

1,2,4,4a-Tetrahydro-cis-2,4-dimethyl-8-nitrospiro[[1,4]oxazino[4,3-a]quinoline-5(6H), 5'(2'H)-pyrimidine]-2',4',6'(1'H,3'H)-trione (12) and 1,2,4,4a-Tetrahydro-trans-2,4-dimethyl-8-nitrospiro[[1,4]oxazino[4,3-a]quinoline-5(6H), 5'(2'H)-pyrimidine]-2',4',6' (1'H,3'H)-trione

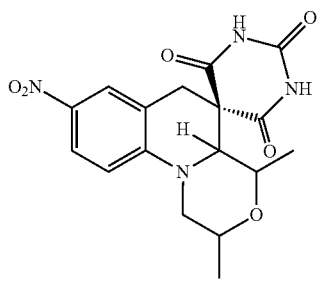

Step 1: Preparation of Cis- and trans-2-(2,6-dimethylmorpholin-4-yl)-5-nitrobenzaldehyde

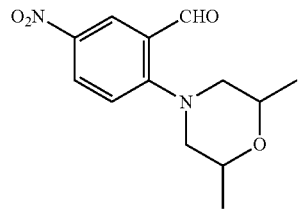 [SMILES: CC1CN(c2ccc([N+](=O)[O-])cc2C=O)CC(C)O1]

A flask is charged with 2-fluoro-5-nitrobenzaldehyde (1.00 g, 5.92 mmol), 2,6-dimethylmorpholine (0.796 g, 6.92 mmol) anhydrous powdered potassium carbonate (0.955 g, 6.92 mmol) and dimethylformamide (5 mL). The mixture is heated to reflux for 1 h, cooled to room temperature and is poured into of 50% saturated brine solution (50 mL). The aqueous layer is extracted with ether (2×). The combined organic extracts are dried ($Na_2SO_4$) and concentrated. The resulting residue is purified by silica gel chromatography using acetone-methylene chloride-heptane (0.5:3:6.5) as the eluent give the major cis isomer (1.18 g, 76%) as a yellow solid and the minor trans isomer (0.257 g, 16%) as a yellow oil. Cis: $^1$H NMR (400 MHz, $CDCl_3$) δ 10.09, 8.63, 8.32, 7.08, 3.93, 3.33, 2.84, 1.27. Trans: $^1$H NMR (400 MHz, $CDCl_3$) δ 10.10, 8.57, 8.27, 7.06, 4.26, 3.32, 3.10, 3.07, 1.31.

Step 2: Preparation of 5-[2-(cis-2,6-dimethylmorpholin-4-yl)-5-nitrobenzylidene]pyrimidine-2,4,6 (1H,3H,5H)-trione (9) and trans-5-[2-(2,6-dimethylmorpholin-4-yl)-5-nitrobenzylidene]pyrimidine-2,4, 6(1H,3H,5H)-trione (10)

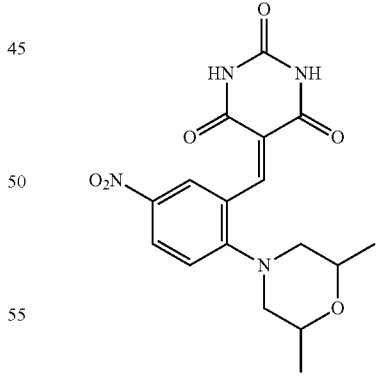

A mixture of cis-2-(2,6-dimethylmorpholin-4-yl)-5-nitrobenzaldehyde (from Step 1) (0.528 g, 2.00 mmol) and barbituric acid (0.256 g, 2.00 mmol) in methanol (20 mL) are stirred at room temperature for 24 h. The reaction mixture is adsorbed onto silica gel (10 g) on rotary evaporator keeping the water bath <30 degrees and then is purified on silica gel using a gradient solvent system acetone-chloroform-acetic acid (1:9:0.5%) initially, then acetone-chloroform-methanolacetic acid (1:8.5:0.5:0.5%) as the eluent to obtain 421 mg (56%) 5-[2-(cis-2,6-dimethylmorpholin-4-yl)-5-nitrobenzylidene]pyrimidine-2,4,6(1H,3H,5H)-trione as an orange solid. ¹H NMR (400 MHz, DMSO-d₆) δ 11.38, 11.27, 8.75, 8.23, 8.01, 7.21, 3.74, 3.29, 2.69, 1.11.

In a similar manner, the minor trans isomer, trans-2-(2,6-dimethylmorpholin-4-yl)-5-nitrobenzaldehyde (from Step 1) is converted to trans-5-[2-(2,6-dimethylmorpholin-4-yl)-5-nitrobenzylidene]pyrimidine-2,4,6(1H,3H,5H)-trione in 50% yield. ¹H NMR (400 MHz, DMSO-d₆) δ 11.38, 11.27, 8.65, 8.23, 8.08, 7.21, 4.06, 3.18, 2.95, 2.92, 1.22.

Step 3: Preparation of 1,2,4,4a-Tetrahydro-cis-2,4-dimethyl-8-nitrospiro[[1,4]oxazino[4,3-a]quinoline-5(6H), 5'(2'H)-pyrimidine]-2',4',6'(1'H,3'H)-trione (12) and 1,2,4,4a-Tetrahydro-trans-2,4-dimethyl-8-nitrospiro[[1,4]oxazino[4,3-a]quinoline-5(6H), 5'(2'H)-pyrimidine]-2',4',6'(1'H,3'H)-trione 5-[2-(cis-2,6-Dimethylmorpholin-4-yl)-5-nitrobenzylidene]pyrimidine-2,4,6(1H,3H,5H)-trione (from Step 2) (2.57 g, 6.87 mmol) is refluxed methanol (230 mL) for 6.25 h. then the reaction mixture is stirred at RT overnight. The bright yellow precipitated solid is isolated by filtration and is dried under high vacuum at 120° C. for 3 days to afford 1,2,4,4a-tetrahydro-cis-2,4-dimethyl-8-nitrospiro[[1,4]oxazino[4,3-a]quinoline-5(6H), 5'(2'H)-pyrimidine]-2',4',6'(1'H,3'H)-trione in nearly quantitative yield. ¹H NMR (400 MHz, DMSO-d₆) δ 11.88, 11.57, 7.97, 7.04, 4.30, 3.92, 3.54, 2.99, 2.87, 1.16, 0.94.

In a similar manner, trans-5-[2-(2,6-dimethylmorpholin-4-yl)-5-nitrobenzylidene]pyrimidine-2,4,6(1H,3H,5H)-trione (from Step 2) is converted to 1,2,4,4a-tetrahydro-trans-2,4-dimethyl-8-nitrospiro[[1,4]oxazino[4,3-a]quinoline-5(6H), 5'(2'H)-pyrimidine]-2',4',6'(1'H,3'H)-trione in 43% yield. ¹H NMR (400 MHz, DMSO-d₆) δ 11.88, 11.60, 7.98, 7.83, 6.85, 6.85, 4.19, 4.07, 3.95, 3.89, 3.63, 3.56, 2.91, 1.24, 0.91.

Example 2

1,2,4,4a-Tetrahydro-cis-2,4-dimethylspiro[[1,4]oxazino[4,3-a]quinoline-5(6H), 5'(2'H)-pyrimidine]-2',4',6'(1'H,3'H)-trione

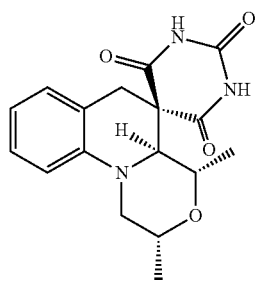

Step 1: Preparation of Cis-2-(2,6-dimethylmorpholin-4-yl)benzaldehyde

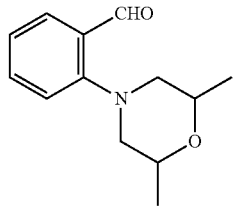 [SMILES: CC1CN(c2ccccc2C=O)CC(C)O1]

In a manner similar to that described in Example 1 (Step 1), cis-2-(2,6-dimethylmorpholin-4-yl)benzaldehyde is obtained in 42% yield as a yellow solid. ¹H NMR (400 MHz, CDCl₃) δ 10.33, 7.83, 7.55, 7.13, 3.94, 3.10, 2.67, 1.25.

Step 2: Preparation of 1,2,4,4a-Tetrahydro-cis-2,4-dimethylspiro[[1,4]oxazino[4,3-a]quinoline-5(6H), 5'(2'H)-pyrimidine]-2',4',6'(1'H,3'H)-trione In a manner similar to that described in Example 1, (Steps 2 and 3) 1,2,4,4a-tetrahydro-cis-2,4-dimethylspiro[[1,4]oxazino[4,3-a]quinoline-5(6H), 5'(2'H)-pyrimidine]-2',4',6'(1'H,3'H)-trione is obtained by allowing a one pot reaction (Steps 2 and 3 in Example 1), to directly form the spirocyclic final product at room temperature in 53% yield as a white solid. ¹H NMR (300 MHz, DMSO-d₆) δ 11.69, 11.43, 7.06, 6.85, 6.54, 4.02, 3.65, 3.59-3.48, 3.23, 2.90, 2.78, 1.14, 0.91.

Example 3

8-Bromo-1,2,4,4a-tetrahydro-cis-2,4-dimethylspiro[[1,4]oxazino[4,3-a]quinoline-5(6H), 5'(2'H)-pyrimidine]-2',4',6'(1'H,3'H)-trione

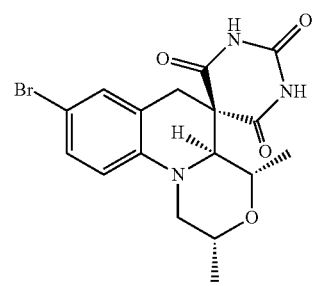

Step 1: Preparation of Cis- and trans-5-bromo-2-(2,6-dimethylmorpholin-4-yl)benzaldehyde

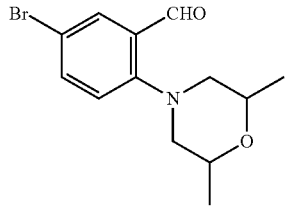 [SMILES: CC1CN(c2ccc(Br)cc2C=O)CC(C)O1]

In a manner similar to that described in Example 1 (Step 1) cis-5-bromo-2-(2,6-dimethylmorpholin-4-yl)benzaldehyde and trans-5-bromo-2-(2,6-dimethylmorpholin-4-yl)benzaldehyde are obtained in 63% and 16% yields as a yellow solid and a yellow oil respectively. Cis-isomer: $^1$H NMR (400 MHz, CDCl$_3$) δ 10.25, 7.91, 7.62, 6.99, 3.96-3.86, 3.04, 2.65, 1.24; Trans-isomer: $^1$H NMR (400 MHz, CDCl$_3$) δ 10.33, 7.91, 7.63, 7.00, 4.28-4.18, 3.11, 2.80, 2.77, 1.34.

Step 2: Preparation of 8-Bromo-1,2,4,4a-tetrahydro-cis-2,4-dimethylspiro[[1,4]oxazino[4,3-a]quinoline-5(6H), 5'(2'H)-pyrimidine]-2',4',6'(1'H,3'H)-trione In a manner similar to that described in Example 1, (Steps 2 and 3) 8-bromo-1,2,4,4a-tetrahydro-cis-2,4-dimethylspiro[[1,4]oxazino[4,3-a]quinoline-5(6H), 5'(2'H)-pyrimidine]-2',4',6'(1'H,3'H)-trione is prepared in 88% yield as a orange solid. $^1$H NMR (400 MHz, DMSO-d$_6$) δ 11.78, 11.48, 7.18, 7.05, 6.81, 4.00, 3.67, 3.64-3.56, 3.56-3.46, 3.30, 2.86, 2.80, 1.13, 0.91.

Example 4

8-Fluoro-1,2,4,4a-tetrahydro-cis-2,4-dimethylspiro[[1,4]oxazino[4,3-a]quinoline-5(6H), 5'(2'H)-pyrimidine]-2',4',6'(1'H,3'H)-trione

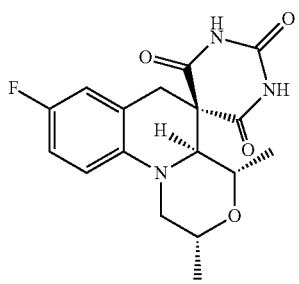

Step 1: Preparation of 2-(2,6-dimethylmorpholin-4-yl)-5-fluorobenzaldehyde

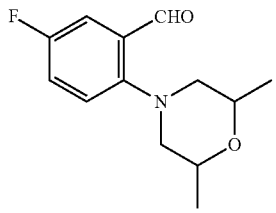 [SMILES: CC1CN(c2ccc(F)cc2C=O)CC(C)O1]

In a manner similar to that described in Example 1 (Step 1) cis-2-(2,6-dimethylmorpholin-4-yl)-5-fluorobenzaldehyde and trans-2-(2,6-dimethylmorpholin-4-yl)-5-fluorobenzaldehyde are obtained in 24% and 6% yields as a yellow solid and a yellow oil, respectively. Cis-isomer: $^1$H NMR (400 MHz, CDCl$_3$) δ 10.37, 7.50, 7.31-7.24, 7.14, 7.12, 3.97-3.86, 3.00, 2.64, 1.24; and trans-isomer: $^1$H NMR (400 MHz, CDCl$_3$) δ 10.45, 7.50, 7.14, 7.12, 4.27-4.17, 3.07, 2.76, 2.74, 1.35.

Step 2: Preparation of 8-Fluoro-1,2,4,4a-tetrahydro-cis-2,4-dimethylspiro[[1,4]oxazino[4,3-a]quinoline-5(6H), 5'(2'H)-pyrimidine]-2',4',6'(1'H,3'H)-trione In a manner similar to that described Example 1, (Steps 2 and 3), 8-fluoro-1,2,4,4a-tetrahydro-cis-2,4-dimethylspiro[[1,4]oxazino[4,3-a]quinoline-5(6H), 5'(2'H)-pyrimidine]-2',4',6'(1'H,3'H)-trione is prepared in 86% yield as a white solid. $^1$H NMR (400 MHz, DMSO-d$_6$) δ 11.74, 11.48, 6.94-6.86, 6.86-6.75, 3.94, 3.66-3.49, 3.26, 2.92, 2.77, 1.13, 0.91.

Example 5

1,2,4,4a-Tetrahydro-cis-2,4-dimethyl-8-trifluoromethylspiro[[1,4]oxazino]-4,3-a]quinoline-5(6H), 5'(2'H)-pyrimidine]-2',4',6'(1'H,3'H)-trione

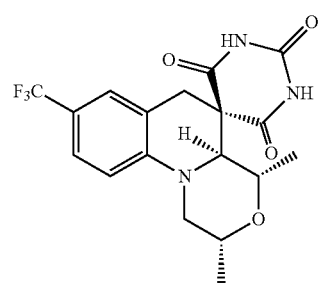

Step 1: Preparation of Cis- and trans-2-(2,6-dimethylmorpholin-4-yl)-5-(trifluoromethyl)benzaldehyde

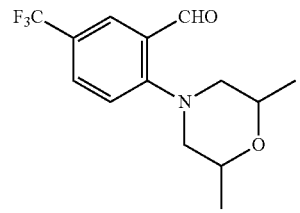 [SMILES: CC1CN(c2ccc(C(F)(F)F)cc2C=O)CC(C)O1]

In a manner similar to that described in Example 1 (Step 1) cis-2-(2,6-dimethylmorpholin-4-yl)-5-(trifluoromethyl)benzaldehyde and trans-2-(2,6-dimethylmorpholin-4-yl)-5-(trifluoromethyl)benzaldehyde are obtained in 74% and 21% yields as yellow oils. Cis-isomer: $^1$H NMR (400 MHz, CDCl$_3$) δ 10.17, 7.98, 7.66, 7.07, 3.90-3.80, 3.09, 2.65, 1.17. Trans-isomer: $^1$H NMR (400 MHz, CDCl$_3$) δ 10.32, 8.08, 7.76, 7.17, 4.32-4.22, 3.22, 2.93, 2.90, 1.37.

Step 2: Preparation of 1,2,4,4a-Tetrahydro-cis-2,4-dimethyl-8-trifluoromethylspiro[[1,4]oxazino[4,3-a]quinoline-5(6H), 5'(2'H)-pyrimidine]-2',4',6'(1'H,3'H)-trione In a manner similar to that described Example 1, (Steps 2 and 3), except after stirring at RT for 24 h, the reaction mixture is heated at reflux for an additional 3 h, 1,2,4,4a-tetrahydro-cis-2,4-dimethyl-8-trifluoromethylspiro[[1,4]oxazino[4,3-a]quinoline-5(6H), 5'(2'H)-pyrimidine]-2',4',6'(1'H,3'H)-trione is prepared in 53% yield as a white solid. $^1$H NMR (400 MHz, DMSO-$d_6$) δ 11.80, 11.51, 7.36, 7.21, 6.99, 4.16, 3.79, 3:65-3.55, 3.55-3.49, 3.45, 2.90, 1.15, 0.93.

Example 6

1,1',2,3'4,4',4a, 6'-Octrahydro-2,4',6'-trioxospiro[[1,4]oxazino[4,3-a]quinoline-5(6H), 5'(2'H)-pyrimidine]-8-carbonitrile

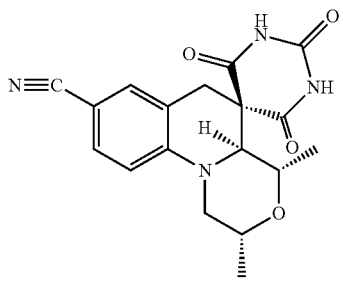

Step 1: Preparation of 4-(cis-2,6-dimethylmorpholin-4-yl)-3-formylbenzonitrile

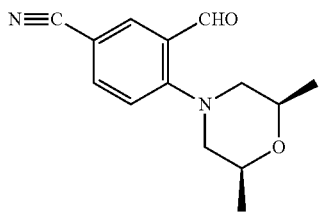 [SMILES: C[C@@H]1CN(c2ccc(C#N)cc2C=O)C[C@H](C)O1]

A mixture of 5-bromo-2-(2,6-dimethylmorpholin-4-yl)benzaldehyde (0.298 g, 1.00 mmol), 1,1'-bis(dimethylphosphino)ferrocene [dppf] (0.022 g, 0.040 mmol), tris(dibenzylideneacetone)dipalladium [$Pd_2(dba)_3$] (0.018 g, 0.020 mmol), zinc dust (0.008 g, 0.12 mmol) and zinc cyanide (0.070 g, 0.60 mmol) in dimethylacetamide (2 mL) is heated 120° C. for 4 h. The reaction mixture is cooled and partitioned between dilute ammonium hydroxide and ethyl acetate. The phases are separated. The organic layer is extracted with an additional portion of ethyl acetate. The combined organic layers are dried ($NaSO_4$) and then concentrated. The resulting residue is purified by silica gel chromatography using ethyl acetate-methylene chloride-heptane (0.5:4.0:5.5) as the eluent to afford, 172 mg (70%) of the cyano aldehyde. $^1$H NMR (400 MHz, $CDCl_3$) δ 10.05, 7.97, 7.64, 7.01, 3.92-3.79, 3.14, 2.70, 1.17.

Step 2: Preparation of 1,1',2,3'4,4',4a, 6'-Octrahydro-2,4',6'-trioxospiro[[1,4]oxazino[4,3-a]quinoline-5(6H), 5'(2'H)-pyrimidine]-8-carbonitrile In a manner similar to that described Example 1 (Steps 2 and 3), except after stirring at RT for 36 h, the reaction mixture is heated at reflux for an additional 24 h to give 1,1',2,3'4,4',4a, 6'-octrahydro-2,4',6'-trioxospiro[[1,4]oxazino[4,3-a]quinoline-5(6H), 5'(2'H)-pyrimidine]-8-carbonitrilein 88% yield as a white solid. $^1$H NMR (400 MHz, DMSO-$d_6$) δ 11.90, 11.60, 7.53, 7.32, 7.06, 4.26, 3.88, 3.68-3.59, 3.59-3.51, 3.46, 2.97, 2.90, 1.20, 0.98.

Example 7

1,2,4,4a-Tetrahydro-cis-2,4-dimethyl-8-carboxamidespiro[[1,4]oxazino[4,3-a]quinoline-5(6H), 5'(2'H)-pyrimidine]-2',4',6'(1'H,3'H)-trione

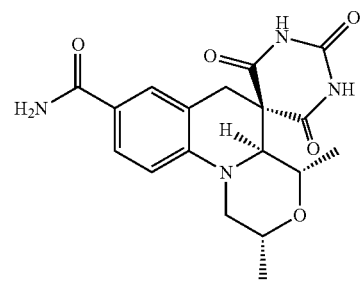

Step 1: Preparation of 4-(cis-2,6-dimethylmorpholin-4-yl)-3-formylbenzamide

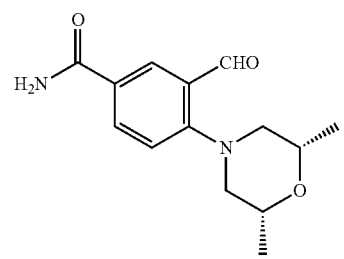 [SMILES: C[C@@H]1CN(c2ccc(C(N)=O)cc2C=O)C[C@H](C)O1]

A solution of 4-(cis-2,6-dimethylmorpholin-4-yl)-3-formylbenzonitrile (Example 6, Step 1) (0.244 g, 1.00 mmol) in acetone (4 mL) is treated with anhydrous powdered potassium carbonate (0.028 g, 0.20 mmol) followed by 30% hydrogen peroxide (0.204 g, 6.00 mmol). The reaction mixture is stirred at room temperature. After 24 h, additional 30% hydrogen peroxide (6.0 mmol) and acetone (2 mL) is added. After stirring at RT for 5 days, an additional potassium carbonate (0.96 g) and DMSO (4 mL) is added and stirred at RT for 24 h. The reaction mixture is poured into 50% saturated brine (40 mL), extracted with ether (3×), dried ($NaSO_4$) and concentrated. The resulting residue is purified by silica gel chromatography using acetone-methylene chloride (1:4) as the eluent, to afford 28 mg (11%) of the desired amide as a yellow foam. $^1$H NMR (400 MHz, $CDCl_3$) δ 10.20, 8.20, 8.09, 7.12, 6.47-5.88, 4.00-3.86, 3.20, 2.74, 1.25.

Step 2: Preparation of 1,2,4,4a-Tetrahydro-cis-2,4-dimethyl-8-carboxamidespiro[[1,4]oxazino[4,3-a]quinoline-5(6H), 5'(2'H)-pyrimidine]-2',4',6'(1'H,3'H)-trione

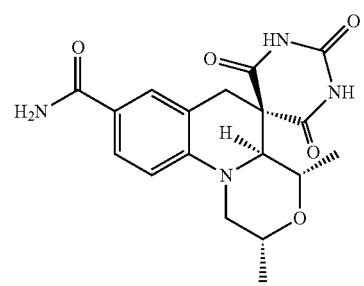

In a manner similar to that described in Example 1 (Steps 2 and 3) 1,2,4,4a-tetrahydro-cis-2,4-dimethyl-8-carboxamide-spiro[[1,4]oxazino[4,3-a]quinoline-5(6H), 5'(2'H)-pyrimidine]-2',4',6'(1'H,3'H)-trione is obtained as a white solid in 90% yield after stirring at RT for 9 days. $^1$H NMR (400 MHz, DMSO-$d_6$) δ 11.78, 11.47, 7.64, 7.60, 7.43, 6.90, 6.87, 4.15, 3.75, 3.62-3.42, 3.28, 2.93-2.81, 1.15, 0.93.

Example 8

1,2,4,4a-Tetrahydro-8-nitrospiro[[1,4]oxazino[4,3-a]quinoline-5(6H), 5'(2'H)-pyrimidine]-2',4',6'(1'H,3'H)-trione

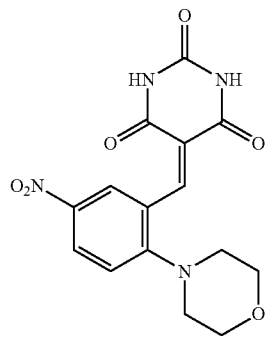

Step 1: Preparation of 2-morpholin-4-yl-5-nitrobenzaldehyde

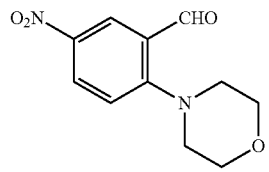

In a manner similar to that described in Example 1 (Step 1), 2-morpholin-4-yl-5-nitrobenzaldehyde is obtained in 89% yield as a yellow solid. $^1$H NMR (400 MHz, CDCl$_3$) δ 10.05, 8.57, 8.26, 7.03, 3.87, 3.23.

Step 2: Preparation of 5-(2-morpholin-4-yl-5-nitrobenzylidene)pyrimidine-2,4,6(1H,3H,5H)-trione

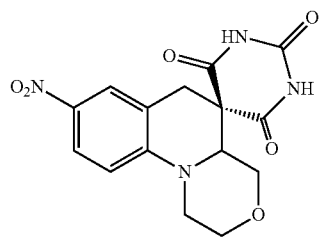

In a manner similar to that described in Example 1 (Step 2) 5-(2-morpholin-4-yl-5-nitrobenzylidene)pyrimidine-2,4,6 (1H,3H,5H)-trione is obtained in a 15% yield as a yellow solid. $^1$H NMR (300 MHz, DMSO-$d_6$) δ 11.40, 11.28, 8.71, 8.25, 8.04, 7.22, 3.74, 3.17.

Step 3: Preparation of 1,2,4,4a-Tetrahydro-8-nitro-spiro[[1,4]oxazino[4,3-a]quinoline-5(6H), 5'(2'H)-pyrimidine]-2',4',6'(1'H,3'H)-trione In a manner similar to that described in Example 1 (Step 3), 1,2,4,4a-tetrahydro-8-nitrospiro[[1,4]oxazino[4,3-a]quinoline-5(6H), 5'(2'H)-pyrimidine]-2',4',6'(1'H,3'H)-trione is obtained in 73% yield. $^1$H NMR (400 MHz, DMSO-$d_6$) δ 11.63, 11.41, 7.96, 7.86, 7.04, 4.13, 3.91, 3.85, 3.76, 3.51-3.38, 3.30-3.11.

Example 9

1,2,4,4a-Tetrahydro-2,4-dimethylspiro[[1,4]oxazino[4,3-a]quinoline-5(6H), 5'(2'H)-pyrimidine]-2',4',6' (1'H,3'H)-trione

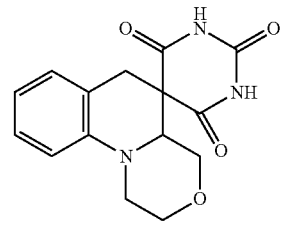 [SMILES: O=C1NC(=O)C2(Cc3ccccc3N3CCOCC32)C(=O)N1]

Step 1: Preparation of 5-(2-morpholin-4-ylbenzylidene)pyrimidine-2,4,6(1H,3H,5H)-trione

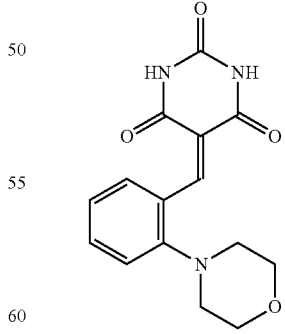

In a manner similar to that described in Example 1 (Step 2) 5-(2-morpholin-4-ylbenzylidene)pyrimidine-2,4,6(1H,3H, 5H)-trione is obtained in 35% yield as an orange solid. $^1$H NMR (400 MHz, DMSO-$d_6$) δ 11.31, 11.12, 8.36, 7.88, 7.48, 7.10, 7.04, 3.72, 2.94.

Step 2: Preparation of 1,2,4,4a-Tetrahydro-2,4-dimethylspiro[[1,4]oxazino[4,3-a]quinoline-5(6H), 5'(2'H)-pyrimidine]-2',4',6'(1'H,3'H)-trione In a manner similar to that described in Example 1 (Step 3) 1,2,4,4a-tetrahydro-2,4-dimethylspiro[[1,4]oxazino[4,3-a]quinoline-5(6H), 5'(2'H)-pyrimidine]-2',4',6'(1'H,3'H)-trione is obtained in 93% yield after refluxing for 2 hours in methanol. $^1$H NMR (400 MHz, DMSO-d$_6$) δ 11.48, 11.35, 7.06, 6.97, 6.90, 6.69, 3.86, 3.70, 3.50, 3.41-3.08, 2.88.

Example 10

8-Bromo-1,2,4,4a-tetrahydro-2,4-dimethylspiro[[1,4]piperazino[4,3-a]quinoline-5(6H), 5'(2'H)-pyrimidine]-2',4',6'(1'H,3'H)-trione

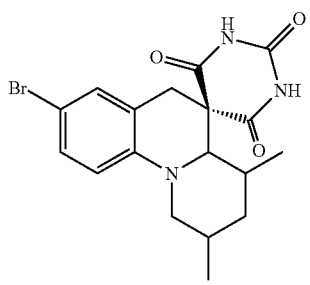

Step 1: Preparation of 5-bromo-2-(3,5-dimethylpiperidin-1-yl)benzaldehyde

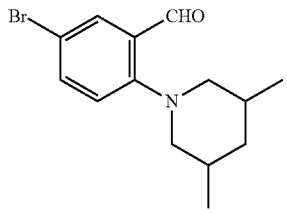 [SMILES: CC1CC(C)CN(c2ccc(Br)cc2C=O)C1]

In a manner similar to that described in Example 1 (Step 1) 5-bromo-2-(3,5-dimethylpiperidin-1-yl)benzaldehyde is obtained as a diastereomeric mixture in 85% yield. $^1$H NMR (400 MHz, CDCl$_3$) δ 10.30, 10.20, 7.90, 7.58, 7.00, 3.17, 3.06, 2.73, 2.70, 2.41, 2.19-2.09, 2.01-1.84, 1.62, 1.46, 1.06, 0.92.

Step 2: Preparation of 8-Bromo-1,2,4,4a-tetrahydro-2,4-dimethylspiro[[1,4]piperazino[4,3-a]quinoline-5(6H), 5'(2'H)-pyrimidine]-2',4',6'(1'H,3'H)-trione In a manner similar to that described in Example 1 (Steps 2 and 3) 8-bromo-1,2,4,4a-tetrahydro-2,4-dimethylspiro[[1,4]piperazino[4,3-a]quinoline-5(6H), 5'(2'H)-pyrimidine]-2',4', 6'(1'H,3'H)-trione is obtained in 89% yield as a white solid. $^1$H NMR (400 MHz, DMSO-d$_6$) δ 11.63, 11.49, 7.15, 7.03, 6.69, 3.87, 3.61, 3.25, 2.78, 2.66, 1.78-1.55, 0.88, 0.65.

Example 11

1,2,4,4a-Tetrahydro-1,4a-dimethyl-8-nitrospiro[[1,4]oxazino[4,3-a]quinoline-5(6H), 5'(2'H)-pyrimidine]-2',4',6'(1'H,3'H)-trione

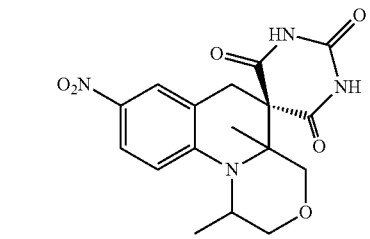

Step 1: Preparation of 3,5-dimethylmorpholine

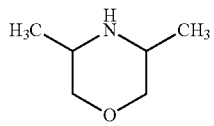

Acetol (10.9 g, 0.133 mmol, 1.17 eq) and dl-2-amino-1-propanol (8.5 g, 0.113, 1.0 eq) are combined in 200 mL of ethanol. The atmosphere above the solvent is purged with nitrogen, platinum oxide (50 mg, 85%, Englehart) is added and the mixture is hydrogenated at room temperature at 38.5 psi overnight. An additional 50 mg of platinum oxide catalyst is added and the reaction mixture is hydrogenated for an additional 18 h. The reaction mixture is filtered through a pad of solka-floc, rinsed thoroughly with ethanol and the filtrate is concentrated. The residue is purified by silica gel chromatography using chloroform-methanol-ammonium hydroxide (29%) (85:15:1) as the eluent to give 10.67 g (71%) of the aminodiol.

Subsequent dehydration of the aminodiol (10.1 g, 0.0759 mol) is carried out in a flask having ample void volume to accommodate the frothing generated by heating with concentrated sulfuric acid (14.14 g, 0.144 mol, 1.90 eq) at 180° C. for 8 h. The black mixture is cooled in an ice bath while potassium hydroxide (17.1 g, 0.304 mol, 4.0 eq) in 85 mL of water is added dropwise over a period of 25 min. The basic suspension is stirred at room temperature overnight, is filtered through a pad of celite and the pad is rinsed two times with water. The aqueous filtrate is extracted five times with chloroform-methanol (85:15), dried (NaSO$_4$) and is concentrated on a rotary evaporator, keeping the water bath temperature 25° C. to minimize loss of volatile product 7.19 g (82%) as a colorless liquid: $^1$H NMR (400 MHz, CDCl$_3$) δ 3.62, 3.23, 3.20, 3.07, 2.89, 1.03, 0.88 3.

Step 2: Preparation of 2-(3,5-dimethylmorpholin-4-yl)-5-nitrobenzaldehyde

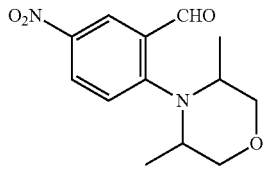

In a manner similar to that described in Example 1 (Step 1), 2-(3,5-dimethylmorpholin-4-yl)-5-nitrobenzaldehyde is obtained in 26% yield as a mixture of cis and trans isomers, which is used immediately in the next reaction without further purification.

Step 3: Preparation of 1,2,4,4a-Tetrahydro-1,4a-dimethyl-8-nitrospiro[[1,4]oxazino[4,3-a]quinoline-5(6H), 5'(2'H)-pyrimidine]-2',4',6'(1'H,3'H)-trione In a manner similar to that described in Example 1 (Steps 2 and 3), 36 mg of 1,2,4,4a-tetrahydro-1,4a-dimethyl-8-nitrospiro[[1,4]oxazino[4,3-a]quinoline-5(6H), 5'(2'H)-pyrimidine]-2',4',6'(1'H,3'H)-trione is obtained as a yellow oil (mixture of cis and trans isomers), after stirring at room temperature for 6 days followed by purification on silca gel using acetate-chloroform-acetic acid (1:2:7:0.5%) as the eluent. $^1$H NMR (400 MHz, DMSO-d$_6$) δ 11.50, 11.36, 7.98, 7.94, 6.85, 3.97, 3.87-3.69, 3.67-3.47, 3.12, 1.29, 1.26.

Example 12

8-Bromo-1,2,4,4a-tetrahydro-cis-2,4-dimethylspiro[[1,4]oxazino[4,3-a]quinoline-5(6H), 5'(2'H)-pyrimidine]-4'-thioxo-2',6'(1'H,3'H)-dione

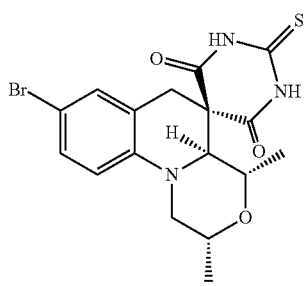

In a manner similar to that described in Example 1 (Steps 2 and 3), except substituting thiobarbituric acid for barbituric acid, 8-bromo-1,2,4,4a-tetrahydro-cis-2,4-dimethylspiro[[1,4]oxazino[4,3-a]quinoline-5(6H), 5'(2'H)-pyrimidine]-4'-thioxo-2',6'(1'H,3'H)-dione is obtained in 82% yield as a yellow solid, after stirring at RT for 24 h and then heating at reflux for 5.5 h. $^1$H NMR (400 MHz, DMSO-d$_6$) δ 12.86, 12.61, 7.19, 7.09, 6.83, 4.01, 3.64, 3.65-3.53, 3.53-3.42, 3.30, 2.91, 2.81, 1.13, 0.90.

Example 13

8-Bromo-1,2,4,4a-tetrahydro-cis-2,4-dimethylspiro[[1,4]oxazino[4,3-a]quinoline-5(6H), 5'(2'H)pyrimidine]-2',4',6'(1'methyl, 3'methyl)-trione

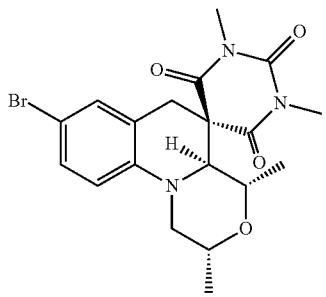

In a manner similar to that described in Example 1 (Steps 2 and 3), except substituting 1,3-dimethylbarbituric acid for barbituric acid, 1,2,4,4a-tetrahydro-cis-2,4-dimethyl-8-bromospiro[[1,4]oxazino[4,3-a]quinoline-5(6H), 5'(2'H)pyrimidine]-2',4',6'(1'methyl, 3'methyl)-trione is obtained in 40% yield as a white solid after stirring at RT for 24 h, then heating at reflux temperature for 5.5 h. $^1$H NMR (400 MHz, DMSO-d$_6$) δ 7.19, 6.98, 6.84, 4.00, 3.68, 3.63-3.52, 3.50-3.39, 3.32, 3.23, 3.09, 2.92, 2.80, 1.12, 0.87.

Example 14

N-[1,1α,2,3',4,4',4a,6'-Octahydro-2,4-dimethyl-2',4', 6% trioxospiro[[1,4]oxazino[4,3-a]quinolone-5(6H), 5'(2'H)-pyrimidin]-8-yl]acetamide

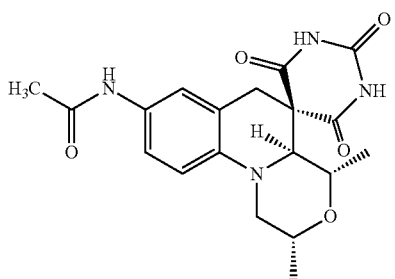

A Parr bottle is charged with 1,2,4,4a-tetrahydro-cis-2,4-dimethyl-8-nitrospiro[[1,4]oxazino[4,3-a]quinoline-5(6H), 5'(2'H)-pyrimidine]-2',4',6'(1'H,3'H)-trione (Example 1, Step 3) (203 mg, 0.542 mmol), acetic anhydride (0.4 mL, 4.24 mmol) and 10-weight % Pd/C (28 mg). Methanol (35 mL) is added and the resulting mixture is shaken at room temperature under 40 psi of H$_2$ for 18 hours. The mixture is filtered through a pad of Celite, and the pad is washed with methanol, 5% methanol in ethyl acetate and then 5% methanol in CH$_2$Cl$_2$. The combined filtrates are concentrated pressure and dried under high vacuum at room temperature for 18 hours. The crude product is purified by silica gel chromatography using 5% methanol in CH$_2$Cl$_2$ as the eluent to give 168.4 mg (80%) of the desired product. ¹H NMR (DMSO-d₆): δ 11.69, 11.40, 9.59, 7.21, 7.15, 6.76, 3.93, 3.61, 3.54, 3.20, 2.90, 2.72, 1.95, 1.12, 0.91.

Example 15 tert-butyl 1,1',2, 3',4,4',4a,6'-Octahydro-2,4-dimethyl-2',4',6'-trioxospiro[[1,4]oxazino[4,3-a]quinolone-5(6H), 5'(2'H)-pyrimidin]-8-ylcarbamate

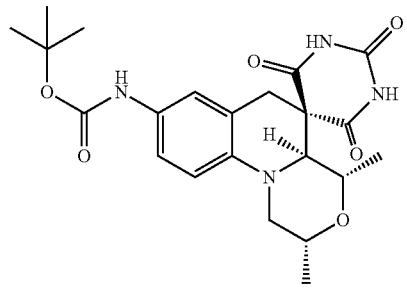

A 200 mL Parr bottle is charged with 1,2,4,4a-tetrahydro-cis-2,4-dimethyl-8-nitrospiro[[1,4]oxazino[4,3-a]quinoline-5(6H), 5'(2'H)-pyrimidine]-2',4',6'(1'H,3'H)-trione (Example 1, Step 3) (6.81 g, 18.2 mmoles), di-tert-butyl dicarbonate (8.62 g, 37.5 mmoles) and 10-weight Pd/C (694 mg). Methanol (750 mL) is carefully added, and the resulting slurry is shake at RT under 30 psi of H₂ for 22 h. The reaction is filtered through a pad of Celite. The pad is washed with methanol, 5% methanol in EtOAc and 5% methanol in CH₂Cl₂ (100 mL each). The filtrate is concentrated. The crude product is dissolved in hot EtOAc and a small amount of methanol and is recrystallized from heptane. After cooling to room temperature and then stirring at 0° C. for 2 hours, the solid is collected by filtration and dried (20 ton, 60° C., 16 hours) to afford 5.67 g (70%) tert-butyl 1,1',2,3',4,4',4a,6'-octahydro-2,4-dimethyl-2',4',6'-trioxospiro[[1,4]oxazino[4,3-a]quinolone-5 (6H),5'(2'H)-pyrimidin]-8-ylcarbamate as a white solid that decomposes at 244° C. The mother liquors from this crystallization are concentrated and the residue is purified by silica gel chromatography using 5% methanol in CH₂Cl₂ as the eluent to give an additional 1.8 g (22%) of the title compound. ¹H NMR (DMSO-d₆): δ 11.68, 11.42, 8.92, 7.05, 6.72, 3.90, 3.61, 3.52, 3.17, 2.88, 2.69, 1.44, 1.12, 0.90.

Example 16

8-Amino-1,2,4,4a-tetrahydro-2,4-dimethylspiro[[1,4]oxazino[4,3-a]quinolone-5(6H), 5'(2'H)-pyrimidine]-2',4',6'(1'H,3'H)-trione monohydrochloride

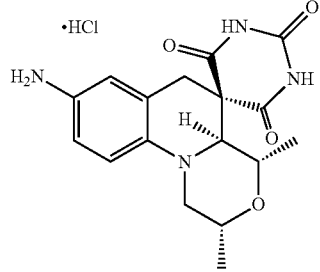

A suspension of tert-butyl 1,1',2,3',4,4',4a,6'-octahydro-2,4-dimethyl-2',4',6'-trioxospiro[[1,4]oxazino[4,3-a]quinolone-5(6H), 5'(2'H)-pyrimidin]-8-ylcarbamate (from Example 15) (7.4 g, 16.65 mmoles) in 250 mL of CH₂Cl₂ at room temperature is treated via pipette with a solution of 4.0 N HCl in dioxane (20 mL, 80 mmoles). The resulting slurry is stirred at room temperature for 2 days and then concentrated. The residue is dissolved in hot 1:1 EtOAc/methanol (~300 mL) and recrystallized from heptane. After cooling to room temperature and then stirring at 0° C. for 30 minutes, the solid is isolated by filtration and dried (20 torr, 60° C., for 18 h) to give 6.31 g (99%) of the title compound as a beige solid. ¹H NMR (DMSO-d₆): δ 11.78, 11.47, 9.83, 7.06, 6.92, 6.87, 4.03, 3.67, 3.60, 3.50, 3.41, 2.90-2.82, 1.13, 0.91.

Example 17

9-Bromo-1,2,4,4a-tetrahydro-2,4-dimethyl-8-nitrospiro[[1,4]oxazino[4,3-a]quinoline-5(6H), 5'(2'H)-pyrimidine]-2',4',6'(1'H,3'H)-trione

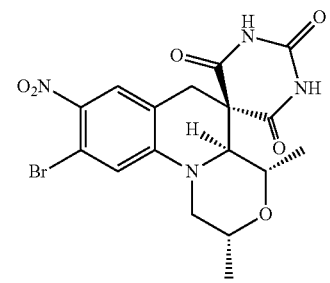

Step 1: Preparation of 4-Bromo-2-fluoro-5-nitrobenzaldehyde

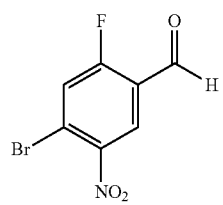 [SMILES: O=Cc1cc([N+](=O)[O-])c(Br)cc1F]

Nitric acid (25 mL) is added dropwise to a solution of 4-bromo-2-fluorobenzaldehyde (5.12 g, 25.2 mmol) in sulfuric acid (25 mL). The mixture is stirred for 2 hours and then is poured over ice. Product is extracted into MTBE (100 mL). The organic layer is washed with saturated aqueous NaHCO₃ (100 mL), dried (Na₂SO₄), and evaporated yielding 5.98 g of yellow solid. ¹H NMR (DMSO-d₆) δ 10.13, 8.49, 8.22.

Step 2: Preparation of 4-Bromo-2-(2,6-dimethylmorpholin-4-yl)-5-nitrobenzaldehyde

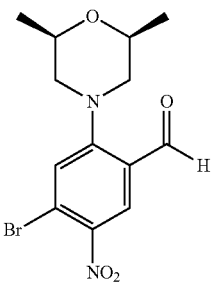

A solution of cis-2,6-dimethylmorpholine (1.06 g, 9.20 mmol) in acetonitrile (40 mL) is added to a flask containing 4-bromo-2-fluoro-5-nitrobenzaldehyde (from Step 1) (2.0 g, 8.06 mmol) and potassium carbonate (3.92 g, 28.4 mmol). The resulting slurry is stirred at room temperature for 63 hours. The mixture is poured into MTBE (100 mL) and is washed with water (100 mL) followed by brine (100 mL). The organics are filtered through silica gel and concentrated to give 1.76 g of bright yellow solid. $^1$H NMR (DMSO-d$_6$) δ 9.93, 8.44, 7.53, 3.74-3.81, 3.48, 2.78, 1.12.

Step 3: Preparation of 9-Bromo-1,2,4,4a-tetrahydro-2,4-dimethyl-8-nitrospiro[[1,4]oxazino[4,3-a]quinoline-5(6H), 5'(2'H)-pyrimidine]-2',4',6'(1'H,3'H)-trione A mixture of 4-bromo-2-(2,6-dimethylmorpholin-4-yl)-5-nitrobenzaldehyde (from Step 2) (989 mg, 2.88 mmol) and barbituric acid (369 mg, 2.88 mmol) in isopropanol (15 mL) is sealed in a 20 mL scintillation vial and shaken at 85° C. for 2.5 hours. The product is adsorbed onto silica gel and purified by silica gel chromatography using a gradient from 20% EtOAc in CH$_2$Cl$_2$ to 25% EtOAc in CH$_2$Cl$_2$ as eluent. Product is isolated and dried (20 Torr, 100° C.) to give 512 mg of yellow solid. $^1$H NMR (DMSO-d$_6$) δ 11.90, 11.62, 7.79, 7.36, 4.32, 3.87, 3.47-3.63, 2.94, 2.81, 1.15, 0.94.

Example 18

8-Acetyl-1,2,4,4a-tetrahydro-2,4-dimethylspiro[[1,4]oxazino[4,3-a]quinoline-5(6H),5'(2H)-pyrimidine)-2',4',6'(1'H,3'H)-trione

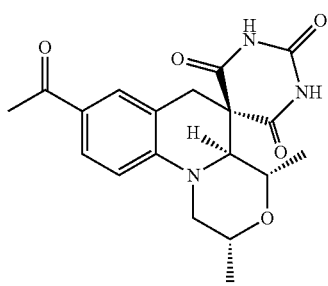

Step 1: Preparation of 5-Bromo-2-(2,6-dimethylmorpholin-4-yl)benzaldehyde

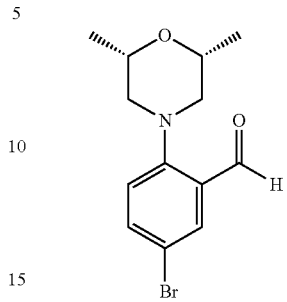

A mixture of 5-bromo-2-fluorobenzaldehyde (16.0 g, 78.6 mmol), cis-2,6-dimethylmorpholine (9.32 g, 80.9 mmol), and potassium carbonate (15.0 g, 108 mmol) in DMF (75 mL) is heated in a 120° C. oil bath for 14 hours. The mixture is diluted with MTBE (250 mL) and washed with water (4×200 mL). (Ethyl acetate is added as needed to maintain the homogeneity of the organic layer). The organics are filtered through a 1" plug of silica gel and evaporated to give 21.5 g of brown solid. This material is approximately 90% pure as judged by HPLC and is used without further purification. $^1$H NMR (DMSO-d$_6$) δ 10.11, 7.78, 7.75, 7.17, 3.77-3.86, 3.12, 2.56, 1.11.

Step 2: Preparation of 4-[4-Bromo-2-(1,3-dioxolan-2-yl)phenyl]-2,6-dimethylmorpholine

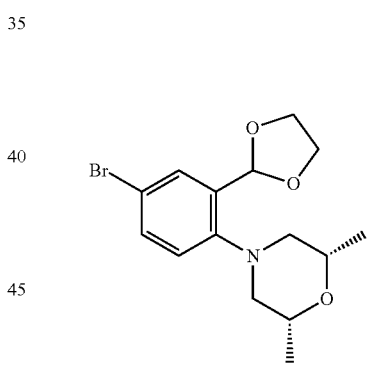

5-Bromo-2-(2,6-dimethylmorpholin-4-yl)benzaldehyde (from Step 1) (10.0 g, 33.5 mmol) is dissolved in toluene (50 ml), and toluenesulfonic acid monohydrate (0.64 g, 3.4 mmol) and ethylene glycol (3.7 ml, 66.3 mmol) are added. The reaction is refluxed for 2.5 hours with a Dean-Stark trap in place. The reaction is neutralized with saturated NaHCO$_3$ solution and extracted with EtOAc (2×). The combined organic layers are washed with brine, dried (Na$_2$SO$_4$) and concentrated give a crude oil (13.09 g). The oil is purified by vacuum flash chromatography using an 85 mm diameter medium glass-sintered fit packed up to 50 mm with 15-40 micron SiO$_2$. The product is eluted using a gradient from 99% heptane, 1% Et$_3$N to 90% ethylene chloride, 9% heptane, 1% Et$_3$N to give 10.89 (95%) of a golden oil. $^1$H NMR (400 MHz, CDCl$_3$) δ 7.66, 7.42, 6.94, 6.13, 4.18, 4.02, 3.83, 3.03, 2.46, 1.19.

Step 3: Preparation of 5-Acetyl-2-(2,6-dimethylmorpholin-4-yl)benzaldehyde

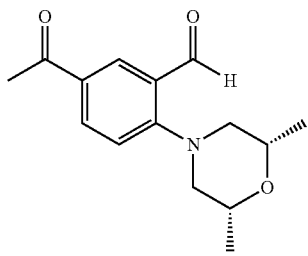 [SMILES: CC(=O)c1ccc(N2C[C@@H](C)O[C@@H](C)C2)c(C=O)c1]

t-Butyl lithium in hexanes (3.8 ml of a 1.7 M solution, 14.5 mmol) is added to THF at −78° C. in a flame dried round-bottomed flask. 4-[4-Bromo-2-(1,3-dioxolan-2-yl)phenyl]-2,6-dimethylmorpholine (from Step 2) (1.0 g, 2.9 mmol) is dissolved in THF (5 mL) and is slowly added to the t-BuLi solution over 7 minutes keeping the temperature below −70° C. The mixture is stirred for 30 minutes and N-methoxy-N-methyl-acetamide (0.34 mL, 3.2 mmol) is slowly added dropwise. The reaction is stirred at −78° C. for 30 minutes and then stored at 0° C. overnight. The reaction is quenched with 1 M HCl (22.5 mL) and then heated at 65° C. for 1 hour. The mixture is basified with 1 M aqueous $Na_2CO_3$ and extracted with EtOAc (2×). The combined organic layers are washed with brine, dried ($Na_2SO_4$) and concentrated. The resulting residue is adsorbed onto silica gel and purified by silica gel chromatography using 15-20% EtOAc in heptane as the eluent to afford 0.35 g (45%) a clear oil. $^1$H NMR (400 MHz, $CDCl_3$) δ 10.1, 8.35, 8.12, 7.08, 3.93, 3.25, 2.76, 2.60, 1.25.

Step 4: Preparation of 8-Acetyl-1,2,4,4a-tetrahydro-2,4-dimethylspiro[[1,4]oxazino[4,3-a]quinoline-5(6H),5'(2H)-pyrimidine)-2',4',6'(1'H,3'H)-trione 5-Acetyl-2-(2,6-dimethylmorpholin-4-yl)benzaldehyde (from Step 3, 0.34 g, 1.3 mmol) and barbituric acid (0.175 g, 1.36 mmol) are dissolved in isopropanol (6 ml) and heated at reflux for 1 hour. The cooled reaction mixture is stored at 0° C. overnight. The light yellow solid is isolated by filtration, washed with cold isopropanol and dried in a vacuum oven (20 Torr, 90° C.) for 2 days to afford 0.48 g (100%) of the title compound. $^1$H NMR (400 MHz, DMSO-$d_6$) δ 11.8, 11.45, 7.70, 7.52, 6.92, 4.36, 4.21, 3.82, 3.76, 3.60, 3.53, 3.43, 2.90, 2.40, 1.15, 0.92.

Example 19

8-Ethanone-O-methyloxime-1-1,2,4,4a-tetrahydro-2,4-dimethylspiro[[1,4]oxazino[4,3-a]quinoline-5(6H),5'(2H)-pyrimidine)-2',4',6'(1'H,3'H)-trione

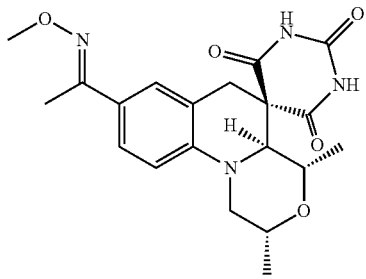

8-Acetyl-1,2,4,4a-tetrahydro-2,4-dimethylspiro[[1,4]oxazino[4,3-a]quinoline-5(6H), 5'(2H)-pyrimidine)-2',4',6' (1'H,3'H)-trione as prepared in Example 18 (0.15 g, 0.40 mmol) and methoxyamine hydrochloride (0.17 g, 2.02 mmol) are dissolved in pyridine (5 mL) and stirred at room temperature overnight. The reaction mixture is diluted with $CH_2Cl_2$ and the solution is washed with saturated $NaHCO_3$ and brine. The organic layer is dried ($Na_2SO_4$) and concentrated. The resulting crude solid is purified by silica gel chromatography using 5% IPA in $CH_2Cl_2$ (150 mL) and 5% MeOH in $CH_2Cl_2$ (100 mL) as the eluent to give 120 mg (74%) of the title compound as a white solid. $^1$H NMR (400 MHz, DMSO-$d_6$) δ 11.75, 11.45, 7.36, 6.84, 4.08, 3.84, 3.60, 3.53, 2.84, 2.07, 1.14, 0.91.

Example 20

1,2,4,4a-Tetrahydro-2,4-dimethyl-8-(methylsulfonyl)spiro[[1,4]oxazino[4,3-a]quinoline-5(6H), 5'(2'H)-pyrimidine]-2',4',6'(1'H,3'H)-trione

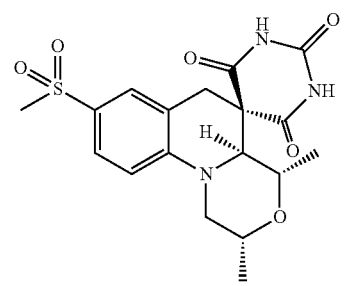

Step 1: Preparation of 4-[2-(1,3-ioxolan-2-yl)-4-(methylthio)phenyl]-2,6-dimethylmorpholine

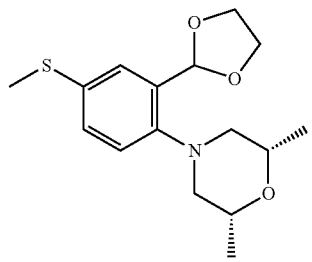

To a stirred solution of 1.7 M t-butyl lithium in hexane (11.4 mL, 19.0 mmol) in THF (35 mL), cooled to −78° C., is added via addition funnel over 15 min, a solution of 4-[4-bromo-2-(1,3-dioxolan-2-yl)phenyl]-2,6-dimethylmorpholine (Example 18, Step 2, (3.0 g, 8.8 mmol)) in THF (15 mL) After stirring for 15 minutes, methyl methanethiol sulfonate (1.0 ml, 9.6 mmol) is added, and the reaction is allowed to warm to 0° C. The reaction is stored at 0° C. overnight. The reaction is poured into saturated aqueous $Na_2CO_3$ and extracted with EtOAc (2×). The combined organic layers are washed with brine, dried (Na$_2$SO$_4$) and concentrated to afford 2.85 g (95%) of a golden oil which is used without further purification.

Step 2: Preparation of 2-(2,6-Dimethylmorpholin-4-yl)-5-(methylsulfonyl)benzaldehyde

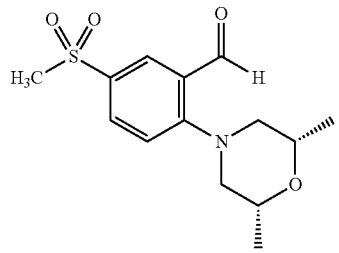

4-[2-(1,3-Ioxolan-2-yl)-4-(methylthio)phenyl]-2,6-dimethylmorpholine (from Step 1) (0.5 g, 1.62 mmol) is dissolved in a mixture of acetone (3 mL) and water (5 mL). Oxone (1.29 g, 2.1 mmol) is dissolved in 0.4 mM EDTA solution (5.3 mL) and is slowly added to the reaction mixture. The resulting suspension is vigorously stirred for one hour. The reaction is treated with a solution of NaHSO$_3$ (82 mg) in water (0.2 ml), followed by 1 M HCl (15 mL). The resulting mixture is heated at 65° C. for 1 hour. The reaction is neutralized with saturated aqueous Na$_2$CO$_3$ and extracted with EtOAc (2×). The combined organic layers are washed with brine, dried (Na$_2$SO$_4$) and concentrated. The resulting residue is adsorbed onto silica gel and purified by silica gel chromatography using 45-50% EtOAc in heptane as the eluent to give 0.24 g (50%) of 2-(2,6-dimethylmorpholin-4-yl)-5-(methylsulfonyl)benzaldehyde as a yellow oil. $^1$H NMR (400 MHz, CDCl$_3$) δ 10.1, 8.31, 8.01, 7.15, 3.93, 3.25, 3.07, 2.79, 1.25.

Step 3: Preparation of 1,2,4,4a-Tetrahydro-2,4-dimethyl-8-(methylsulfonyl)spiro[[1,4]oxazino[4,3-a]quinoline-5(6H), 5'(2'H)-pyrimidine]-2',4',6'(1'H,3'H)-trione In a similar manner as described in Example 18 (Step 4), 0.18 g (57%) of 1,2,4,4a-tetrahydro-2,4-dimethyl-8-(methylsulfonyl)spiro[[1,4]oxazino[4,3-a]quinoline-5(6H), 5'(2'H)-pyrimidine]-2',4',6'(1'H,3'H)-trione is obtained. $^1$H NMR (400 MHz, DMSO-d$_6$) δ 11.7, 7.55, 7.39, 4.21, 3.82, 3.60, 3.52, 3.04, 2.90, 1.15, 0.93.

Example 21

1,2,4,4a-Tetrahydro-2,4-dimethyl-8-(methylsulfinyl)spiro[[1,4]oxazino[4,3-a]quinoline-5(6H), 5'(2'H)-pyrimidine]-2',4',6'(1'H,3'H)-trione

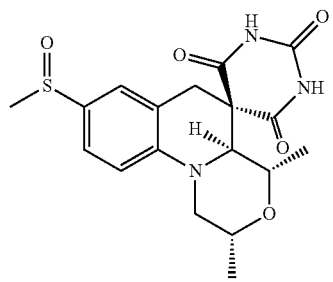

Step 1: Preparation of 2-(2,6-Dimethylmorpholin-4-yl)-5-(methylsulfinyl)benzaldehyde

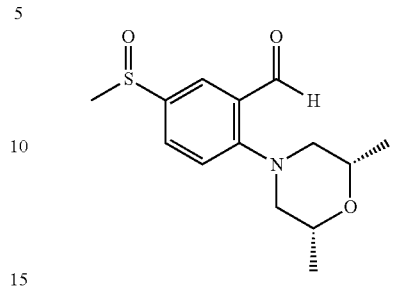

4-[2-(1,3-Ioxolan-2-yl)-4-(methylthio)phenyl]-2,6-dimethylmorpholine from Example 20 (Step 1, (1.6 g, 5.17 mmol)) is dissolved in a mixture of acetone (15 mL) and water (15 mL). The slurry is cooled to 0° C. and solid NaHCO$_3$ (3.79 g) is added. To this stirred slurry is added dropwise a solution of Oxone (2.3 g) in 0.4 mM aqueous EDTA (10 mL) while keeping the temperature below 5° C. The slurry is stirred for 5 minutes and then is treated with a solution of NaHSO$_3$ (1.42 g) in water (2.8 mL) followed dioxane (10 mL) and 6 N HCl (9 mL). The reaction mixture is heated to 65° C. for 1 hour. The reaction mixture is neutralized with saturated aqueous Na$_2$CO$_3$ solution and extracted with EtOAc (2×). The combined organic layers are washed with brine, dried (Na$_2$SO$_4$) and concentrated. The crude oil is purified by silica gel chromatography using EtOAc as the eluent to give 0.80 g (55%) of a yellow oil. $^1$H NMR (400 MHz, CDCl$_3$) δ 10.25, 7.98, 7.89, 7.23, 3.93, 3.16, 2.74, 2.74, 1.25.

Step 3: Preparation of 1,2,4,4a-Tetrahydro-2,4-dimethyl-8-(methylsulfinyl)spiro[[1,4]oxazino[4,3-a]quinoline-5(6H), 5'(2'H)-pyrimidine]-2',4',6'(1'H, 3'H)-trione In a similar manner as described in Example 18 (Step 4), 0.85 g (77%) of 1,2,4,4a-tetrahydro-2,4-dimethyl-8-(methylsulfinyl)spiro[[1,4]oxazino[4,3-a]quinoline-5(6H), 5'(2'H)-pyrimidine]-2',4',6'(1'H,3'H)-trione is obtained as a white solid. $^1$H NMR (400 MHz, DMSO-d$_6$) δ 11.8, 11.5, 7.36, 7.23, 7.01, 4.14, 3.76, 3.60, 3.52, 3.42, 2.87, 2.63, 1.14, 0.92.

Example 22

1,2,4,4a-Tetrahydro-2,4-dimethyl-8-(methylthio)spiro[[1,4]oxazino[4,3-a]quinoline-5(6H), 5'(2'H)-pyrimidine]-2',4',6'(1'H,3'H)-trione

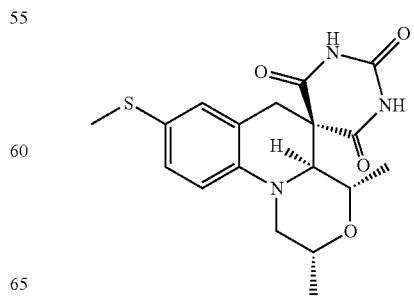

Step 1: Preparation of 2-(2,6-Dimethylmorpholin-4-yl)-5-(methylthio)benzaldehyde

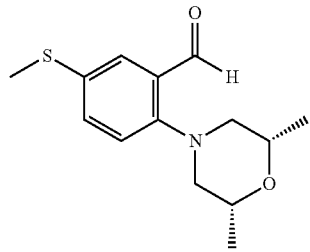

4-[2-(1,3-Ioxolan-2-yl)-4-(methylthio)phenyl]-2,6-dimethylmorpholine (Example 20, Step 1, 0.5 g), is dissolved in dioxane (10 mL) and 1 M HCl (10 mL). The mixture is heated at reflux for 15 minutes. The reaction is quenched into saturated $Na_2CO_3$ and is extracted with EtOAc (2×). The combined organic layers are washed with brine and then concentrated. The crude oil is adsorbed onto silica gel and is purified by silica gel chromatography using 10 to 20% EtOAc in heptane as the eluent to give 270 mg (59%) of 2-(2,6-dimethylmorpholin-4-yl)-5-(methylthio)benzaldehyde as a yellow oil. $^1$H NMR (400 MHz, $CDCl_3$) δ 10.3, 7.69, 7.45, 7.04, 3.90, 3.02, 2.63, 2.49, 1.22.

Step 2: Preparation of 1,2,4,4a-Tetrahydro-2,4-dimethyl-8-(methylthio)spiro[[1,4]oxazino[4,3-a]quinoline-5(6H),5'(2'H)-pyrimidine]-2',4',6'(1'H,3'H)-trione In a similar manner as described in Example 18 (Step 4), 0.31 g (84%) of 1,2,4,4a-tetrahydro-2,4-dimethyl-8-(methylthio)spiro[[1,4]oxazino[4,3-a]quinoline-5(6H), 5'(2'H)-pyrimidine]-2',4',6'(1'H,3'H)-trione is obtained as a white solid. $^1$H NMR (400 MHz, DMSO-$d_6$) δ 11.75, 11.45, 7.05, 6.90, 6.82, 3.99, 3.63, 3.60, 3.53, 3.25, 2.87, 2.77, 2.34, 1.13, 0.91.

Example 23

1,2,4,4a-Tetrahydro-2,4-dimethyl-9-nitrospiro[[1,4]oxazino[4,3-a]quinoline-5(6H), 5'(2'H)-pyrimidine]-2',4',6'(1'H,3'H)-trione

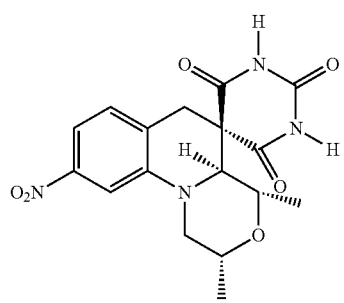

Step 1: Preparation of 2-Fluoro-4-nitrobenzaldehyde-bis-acetate

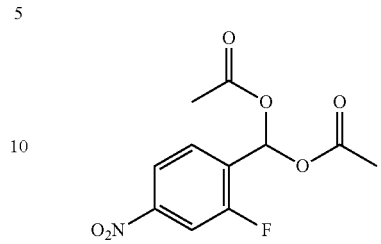

2-Fluoro-2-nitrotoluene (10.0 g, 63.2 mmol), acetic acid (100 mL) and acetic anhydride (100 mL) are added to a 500 ml 3-necked round-bottomed flask and cooled to −14° C. with a salt water ice bath. Concentrated sulfuric acid (14.6 mL) is slowly added over 10 min keeping the temperature below 10° C. Chromium trioxide (17.56 g, 175.6 mmol) is then slowly added over 30 minutes keeping the temperature below −9° C. The reaction is warmed to 0° C. and stirred for 1.5 hours. The reaction is poured into ice water (1000 mL) and is stirred for 15 minutes. The dark green slurry is filtered and the resulting light green solid is washed with cold water. The solid is slurried with cold aqueous $Na_2CO_3$, filtered, rinsed with cold water and cold EtOH to give 6.93 g, (40%) of a white solid. $^1$H NMR (400 MHz, $CDCl_3$) δ 8.09, 7.99, 7.93, 7.75, 2.16.

Step 2: Preparation of 2-Fluoro-4-nitrobenzaldehyde

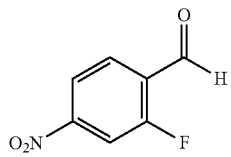 [SMILES: O=Cc1ccc([N+](=O)[O-])cc1F]

2-Fluoro-4-nitrobenzaldehyde-bis-acetate (from Step 1, (6.9 g, 25.4 mmol)), EtOH (15 mL, water (15 mL) and concentrated sulfuric acid (1.4 mL) are mixed together and heated to reflux for 40 minutes. The reaction mixture is filtered through Solka-flok and is cooled to 0° C. The white solid precipitate is isolated by filtration, washed with cold water and dried (20 Torr, 70° C.) to give 3.2 g (49%) of the desired aldehyde: $^1$H NMR (400 MHz, $CDCl_3$) δ 10.5, 8.16, 8.09.

Step 3: Preparation of 2-(2,6-Dimethylmorpholin-4-yl)-4-nitrobenzaldehyde

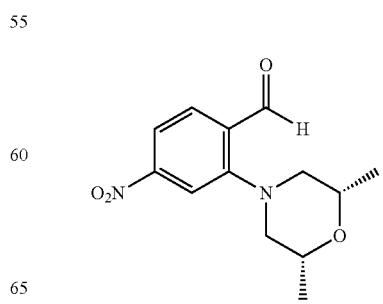

A stirred mixture of 2-fluoro-4-nitrobenzaldehyde (1.0 g, 5.9 mmol), K$_2$CO$_3$ (2.05 g, 14.8 mmol) and cis-dimethylmorpholine (0.75 g, 6.5 mmol) in CH$_3$CN (10 mL) is heated at reflux overnight. The reaction is cooled, diluted with water and extracted with CH$_2$Cl$_2$ (2×). The combined organic layers are washed with brine, dried (Na$_2$SO$_4$) and concentrated. The resulting crude residue is adsorbed onto silica gel and is purified by silica gel chromatography using 50-100% CH$_2$Cl$_2$ in heptane as the eluent to afford 0.48 g (31%) of the desired product as an orange solid. $^1$H NMR (400 MHz, CDCl$_3$) δ 10.3, 7.93, 3.93, 3.14, 2.75, 1.26.

Step 4: Preparation of 1,2,4,4a-Tetrahydro-2,4-dimethyl-9-nitrospiro[[1,4]oxazino[4,3-a]quinoline-5 (6H), 5'(2'H)-pyrimidine]-2',4',6'(1'H,3'H)-trione In a similar manner as described in Example 18 (Step 4), 360 mg (59%) of 1,2,4,4a-tetrahydro-2,4-dimethyl-9-nitrospiro[[1,4]oxazino[4,3-a]quinoline-5(6H), 5'(2'H)-pyrimidine]-2',4',6'(1'H,3'H)-trione is obtained as an orange solid. $^1$H NMR (400 MHz, DMSO-d$_6$) δ 11.8, 11.5, 7.63, 7.39, 7.12, 4.18, 3.74), 3.63, 3.49, 3.17, 2.92, 1.17, 0.94.

Example 24

1,2,4,4a-Tetrahydro-2,4-dimethyl-8-nitrospiro[[1,4]oxazino[4,3-a]quinoline-5(6H), 5'(2'H)-pyrimidine]-2',4',6'(1'methyl,3'methyl)-trione and 1,2,4,4a-Tetrahydro-2,4-dimethyl-8-nitrospiro[[1,4]oxazino[4,3-a]quinoline-5(6H), 5'(2'H)-pyrimidine]-2',4',6'(1'H, 3'methyl)-trione

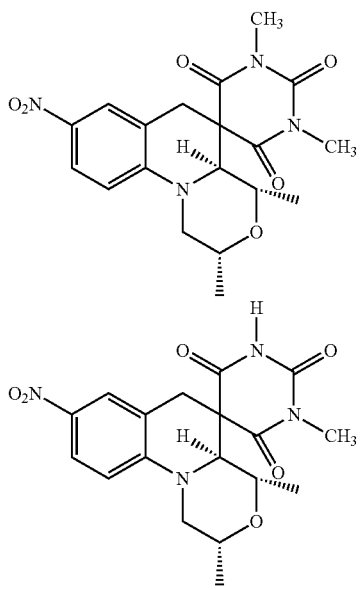

1,2,4,4a-Tetrahydro-cis-2,4-dimethyl-8-nitrospiro[[1,4]oxazino[4,3-a]quinoline-5(6H), 5'(2'H)-pyrimidine]-2',4',6' (1'H,3'H)-trione from Example 1 (0.45 g, 1.16 mmol) is dissolved in DMF (25 mL) and iodomethane (0.15 mL, 2.32 mmol) is added. The reaction is cooled to 0° C., and a solution of 1 M potassium t-butoxide in THF (1.8 mL, 1.8 mmol) is added dropwise over 5 minutes. The reaction is stirred for 90 minutes. The reaction is diluted with water and extracted with CH$_2$Cl$_2$ (2×). The combined organic layers are washed with water (3×), dried (Na$_2$SO$_4$) and concentrated. The resulting crude residue is absorbed on to silica gel and purified by silica gel chromatography using 0.5-2% MeOH in CH$_2$Cl$_2$ as the eluent to afford 0.20 g (33%) of 1,2,4,4a-tetrahydro-2,4-dimethyl-8-nitrospiro[[1,4]oxazino[4,3-a]quinoline-5(6H), 5'(2'H)-pyrimidine]-2',4',6'(1'methyl,3'methyl)-trione as a yellow solid after drying at 55° C. for 3 days ($^1$H NMR (400 MHz, CDCl$_3$) δ 8.10, 7.77, 6.75, 4.08, 3.76, 3.61, 3.42, 3.25, 3.19, 3.11, 2.99, 1.26, 0.98). Further elution yielded 0.21 g, (36%) of 1,2,4,4a-tetrahydro-2,4-dimethyl-8-nitrospiro[[1,4]oxazino[4,3-a]quinoline-5(6H), 5'(2'H)-pyrimidine]-2',4', 6'(1'H, 3'methyl)-trione (mixture of diastereomers) as a yellow solid after drying at 55° C. for 3 days ($^1$H NMR (400 MHz, DMSO-d$_6$) δ 11.8, 7.98, 7.77, 7.05, 4.30, 3.94, 3.53, 3.21, 3.02, 2.98, 2.87, 1.16, 0.92).

Example 25

1,2, 4,4a-Tetrahydro-4-methyl-8-nitrospiro[[1,4]oxazino[4,3-a]quinoline-5(6H), 5'(2'H)-pyrimidine]-2',4',6'(1'H,3'H)-trione and 1,2,4,4a-Tetrahydro-2-methyl-8-nitrospiro[[1,4]oxazino[4,3-a]quinoline-5(6H), 5'(2'H)-pyrimidine]-2',4',6'(1'H,3's)-trione

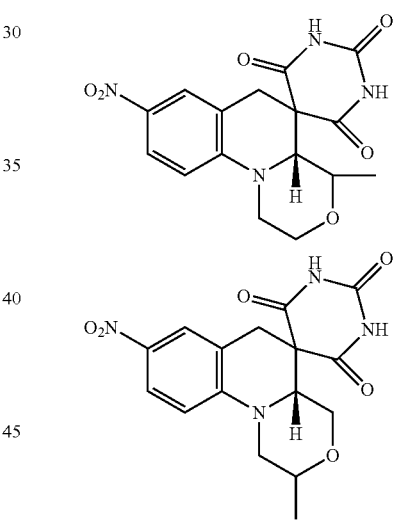

Step 1

To a stirred solution of 2-methylmorpholine hydrochloride in DMF (5 mL) is added diisopropylethylamine (0.25 mL, 1.48 mmol) followed by 2-fluoro-5-nitrobenzaldehyde (210.1 mg, 1.24 mmol) and solid potassium carbonate (198.8 mg, 1.44 mmol). The reaction mixture is heated at 120° C. for 2 h. The reaction mixture is cooled and partitioned between ether and half-saturated brine. The phases are separated. The aqueous layer is extracted with ether (3×). The combined organic phases are dried (MgSO$_4$), filtered and concentrated. The resulting residue is dissolved in CH$_2$Cl$_2$ and is purified by silica gel chromatography using 20% ethyl acetate in hexane as the eluent gave 303.0 mg (1.21 mmol, 98%) of the desired product as a bright yellow solid.

Step 2

In a manner similar to that described in Example 1 (Steps 2 and 3) 255.1 mg (60%) of the desired product as a mixture isomers is obtained. ¹H NMR (400 MHz, DMSO-d₆) δ 11.9, 11.75, 11.6, 11.5, 11.35, 11.3, 7.96, 7.89, 7.83, 7.05, 6.9, 4.28-3.11, 3.16, 2.89, 1.17, 0.95.

Example 26

2,3,4,4a-Tetrahydro-1',3,3'-trimethylspiro[1H-pyrazino[1,2-a]quinolinie-5(6H),5'(2'H)-pyrimidine]-2'4',6'(1'H,3'H)-trione

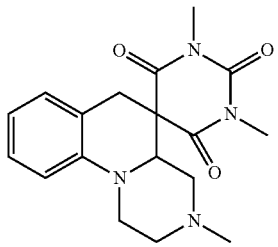 [SMILES: CN1CCN2c3ccccc3CC3(C(=O)N(C)C(=O)N(C)C3=O)C2C1]

In a manner similar to that described in Example 1, except starting with 2-fluorobenzaldehyde, 1-methylpiperazine and 1,3-dimethylbarbituric acid, 190 mg (55%) of the title compound is obtained. ¹H NMR (400 MHz, CDCl₃) δ 7.19, 7.04, 6.95, 6.80, 3.98, 3.62, 3.55, 3.39, 3.32, 3.10, 3.04, 2.82, 2.57, 2.23, 2.21, 1.86.

Example 27

2,3,4,4a-Tetrahydro-3-methylspiro[1H-pyrazino[1,2-a]quinoline-5(6H), 5'(2'H)-pyrimidine]-2',4'6'(1'H,3'H)-trione

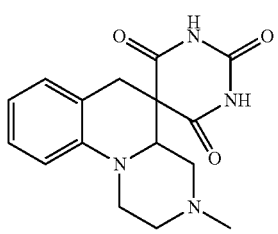 [SMILES: CN1CCN2c3ccccc3CC3(C(=O)NC(=O)NC3=O)C2C1]

In a manner similar to that described in Example 1, except starting with 2-fluorobenzaldehyde and 1-methylpiperazine, 278 mg (89%) of the title compound is obtained. ¹H NMR (400 MHz, DMSO-d₆) δ 11.46, 11.28, 7.03, 6.95, 6.89, 6.66, 3.91, 3.30, 3.17, 3.11, 2.80, 2.75, 2.59, 2.16, 1.98, 1.78.

Example 28

1,1-Dimethylethyl 1,1'2,3',4',4a,6'-octahydro-8-nitro-2',4',6'-trioxospiro[3H-pyrazino[1,2-a]quinoline-5(6H), 5'(2'H)-pyrimidine]-3-carboxylate

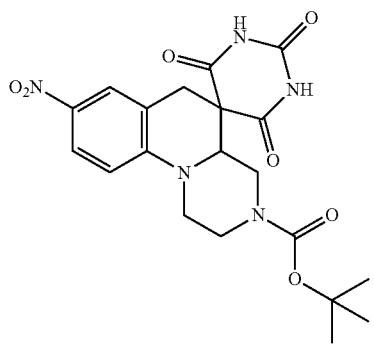 [SMILES: CC(C)(C)OC(=O)N1CCN2c3ccc([N+](=O)[O-])cc3CC3(C(=O)NC(=O)NC3=O)C2C1]

In a manner similar to that described in Example 1, except starting with 1-Boc-piperazine, 1.37 g (63%) of the title compound is obtained. ¹H NMR (400 MHz, DMSO-d₆) δ 11.59, 11.41, 7.95, 7.90, 7.01, 4.12, 3.85, 3.80, 3.41, 3.17, 3.06, 3.01, 2.88, 1.40

Example 29

1,1-Dimethylethyl-8-cyano-1,1',2,3',4,4',4a,6'-octahydro-2',4',6'-trioxospiro[3H-pyrazino[1,2-a]quinoline-5(6H), 5'(2'H)-pyrimidine]-3-carboxylate

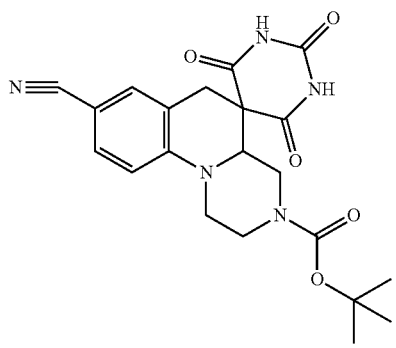 [SMILES: CC(C)(C)OC(=O)N1CCN2c3ccc(C#N)cc3CC3(C(=O)NC(=O)NC3=O)C2C1]

In a manner similar to that described in Example 1, except starting 5-cyano-2-fluorobenzaldehyde and 1-Boc-piperazine, 3.59 g (83%) of 1,1-dimethylethyl-8-cyano-1,1',2,3',4,4',4a,6'-octahydro-2',4',6'-trioxospiro[3H-pyrazino[1,2-a]quinoline-5(6H), 5'(2'H)-pyrimidine]-3-carboxylate is obtained. ¹H NMR (400 MHz, DMSO-d₆) δ 11.45, 11.38, 7.45, 7.40, 6.99, 4.05, 3.80, 3.73, 3.70, 3.27, 3.18, 3.10, 2.95, 2.78, 1.39

Example 30 rel-(2'R,4'S,4'aR)-1,1',2'3'4'4'a-Hexahydro-2',4'-dimethyl-1,3-dioxospiro[2H-indene-2,5'(6'H)-[1,4]oxazino[4,3-a]quinoline]-8'-carbonitrile

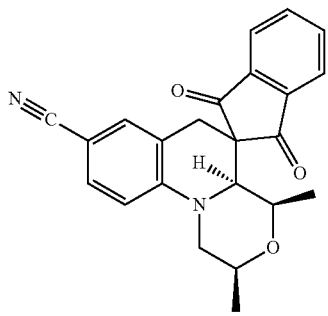

In a manner similar to that described in Example 1, except starting with 5-cyano-2-fluorobenzaldehyde and indanedione, 112 mg (30%) of the title compound is obtained. $^1$H NMR (400 MHz, DMSO-d$_6$) δ 8.03, 7.93, 7.53, 7.34, 6.91, 4.32, 4.26, 3.93, 3.65, 3.30, 3.13, 2.97, 1.09, 0.82

Example 31 rel-(2R,4S,4aR)-1,2,4,4a-Tetrahydro-2,4-dimethyl[1,4]oxazino[4,3-a]quinoline-5,5,8(6H)-tricarbonitrile

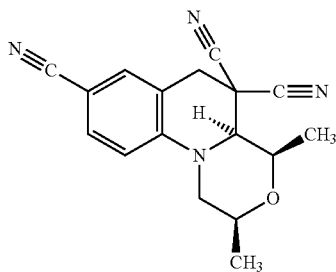

In a manner similar to that described in Example 1, except starting with 5-cyano-2-fluorobenzaldehyde and malononitrile, 93 mg (32%) of the title compound is obtained. $^1$H NMR (400 MHz, CDCl$_3$) δ 7.52, 7.40, 6.97, 4.39, 4.15, 3.69, 3.66, 3.59, 3.53, 3.49, 3.40, 3.37, 1.68, 1.29

Example 32 rel-(2S,4R,4aS)-8-Bromo-1,2,4-4a-tetrahydro-2,4-dimethyl[1,4]oxazino[4,3-a]quinoline-5,5(6H)-dicarbonitrile

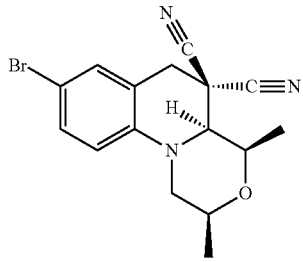

In a manner similar to that described in Example 1, except starting with 5-bromo-2-fluorobenzaldehyde and malononitrile, 1.26 g (54%) of the title compound is obtained. $^1$H NMR (400 MHz, DMSO-d$_6$) δ 7.40, 3.37, 7.11, 4.23, 3.98, 3.86, 3.81, 3.74, 3.55, 3.12, 1.54, 1.13

Example 33

2,3,4,4a-Tetrhydro-3-methyl-8-nitro-2'-thioxospiro[1H-pyrazino[1,2-a]quinoline-5(6H), 5'(2'H)-pyrimidine]-4',6'(1'H,3'H)-dione)

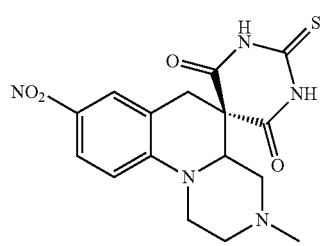

In a manner similar to that described in Example 1, except using 1-methylpiperazine and thiobarbituric acid, 840 mg (81%) of the title compound is obtained. $^1$H NMR (400 MHz, DMSO-d$_6$) δ 12.61, 12.49, 7.94, 7.88, 7.07, 4.18, 3.71, 3.40, 3.17, 3.11, 2.80, 2.65, 1.96, 1.78.

In other embodiments, the compounds of formula I may be synthesized by the scheme in Chart 10.

CHART 10: Alternative Synthetic Scheme:

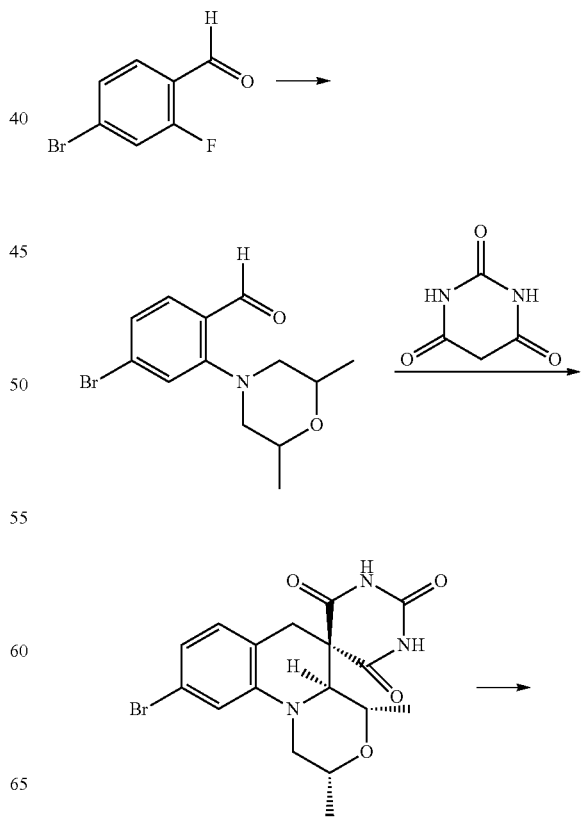

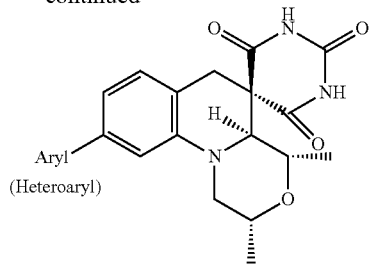

Example 34 rel-(2R,4S,4aS)-9-(4-Chlorophenyl)-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione

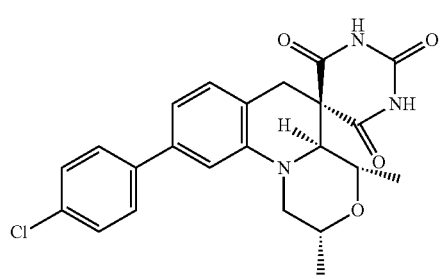

A mixture 9-bromo-1,2,4,4a-tetrahydro-2,4-dimethyspiro[[1,4]piperazino[4,3-a]quinoline-5(6H), 5'(2'H)-pyrimidine]-2',4',6'(1'H,3'H)-trione (0.245 mmol) [as prepared according to Example 10 (Steps 1-3) except using 4-bromo-2-fluorobenzaldehyde as the starting aldehyde], 4-chlorophenylboronic acid (0.27 mmol), sodium carbonate (0.61 mmol), tetrakis(triphenylphosphine) palladium(0) (0.013 mmol) in THF (18 mL) and water (2 mL) is purged with nitrogen and is heated to reflux for 18 h. The mixture is cooled to room temperature and diluted with ethyl acetate (20 mL) and filtered. The filtrate is concentrated and the resulting a semi-solid residue is purified on silica gel using 20% ethyl acetate in dichloromethane as the eluent to afford 15 mg (15%) of the desired coupled product. $^1$H NMR (400 MHz, Acetone-d$_6$) δ 1.10, 1.26, 3.03, 3.1-3.3, 3.7-3.85, 3.9, 4.05, 6.85, 6.96, 7.4, 7.5, 8.8, 9.1.

Example 35 rel-(2R,4S,4aS)-1,2,4,4a-Tetrhydro-2,4-dimethyl-9-[4-(trifluoromethyoxy)phenyl]spiro[[1,4]oxazino[4,3-a]quinoline-5(6H), 5'(2'H)pyrimidine]-2'4'6'(1'H,3'H)-trione

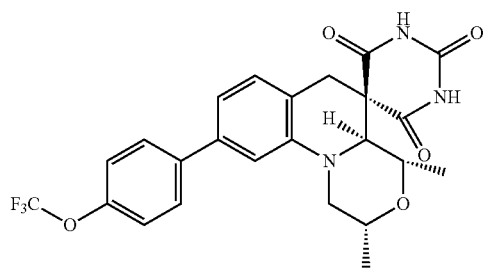

In a manner similar to that described for Example 34, 19 mg (17%) of rel-(2R,4S,4aS)-1,2,4,4a-tetrhydro-2,4-dimethyl-9-[4-(trifluoromethyoxy)phenyl]spiro[[1,4]oxazino[4,3-a]quinoline-5(6H), 5'(2'H)pyrimidine]-2'4'6'(1'H,3'H)-trione is obtained: $^1$H NMR (400 MHz, Acetone-d$_6$) δ 1.07, 1.22, 2.99, 3.15, 3.16, 3.6-3.8, 3.85, 4.29-4.34, 6.86, 6.88, 7.40, 7.76.

Example 36 rel-(2R,4S,4aS)-1,2,4,4a-Tetrahydro-9-(methoxyphenyl)-2,4-dimethylspiro[[1,4]oxazino[4,3-a]quinoline-5(611),5'(27-1)-pyrimidine]-2',4',6'(1'H,3'H)-trione

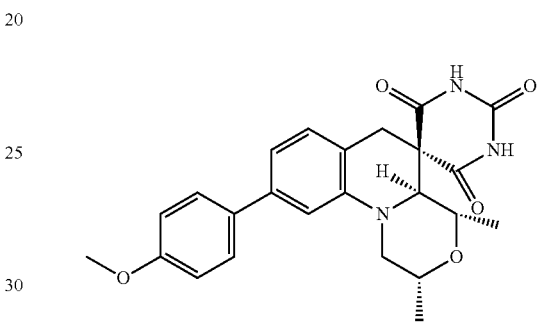

In a manner similar to that described for Example 34, 45 mg (45) of rel-(2R,4S,4aS)-1,2,4,4a-tetrahydro-9-(methoxyphenyl)-2,4-dimethylspiro[[1,4]oxazino[4,3-a]quinoline-5(6H), 5'(2'H)-pyrimidine]-2',4',6'(1'H,3'H)-trione is obtained. $^1$H NMR (400 MHz, CD$_3$OD) δ 0.93, 1.2, 2.9, 3.15, 3.7-3.80, 3.83, 6.8, 6.9, 6.95, 7.53.

Example 37 rel-(2R,4S,4aS)-9-(3-Chloro-4-fluorophenyl)-1,2,4,4a-tetrahydro-2,4-dimethylsprio[[1,4]oxazino[4,3-a]quinoline-5(6H), 5'(TH)-pyrimidine]-2',4',6'(1'H,3'H)-trione

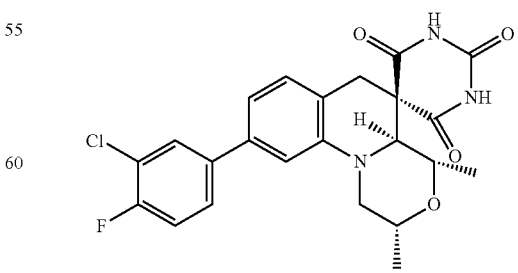

In a manner similar to that described for Example 34, 45 mg (40%) of rel-(2R,4S,4aS)-9-(3-chloro-4-fluorophenyl)-1,2,4,4a-tetrahydro-2,4-dimethylsprio[[1,4]oxazino[4,3-a]quinoline-5(6H), 5'(2'H)-pyrimidine]-2',4',6'(1'H,3'H)-trione is obtained. ¹H NMR (400 MHz, CD₃OD) δ 0.96, 1.26, 2.92, 3.15, 3.7, 3.75-3.82, 4.15, 6.80, 6.97, 7.3, 7.6, 7.7.

Example 38 rel-(2R,4S,4aS)-1,2,4,4a-Tetrahydro-2,4-dimethyl-9-(3-nitrophenyl)spiro[[1,4]oxazino[4,3-a]quinoline-5(6H), 5'(2'H)-pyrimidine]-2',4',6'(1'H,3'H)trione

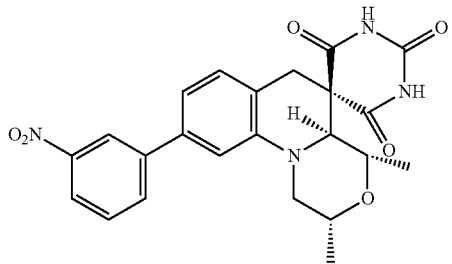

In a manner similar to that described for Example 34, 49 mg (44%) of rel-(2R,4S,4aS)-1,2,4,4a-tetrahydro-2,4-dimethyl-9-(3-nitrophenyl)spiro[[1,4]oxazino[4,3-a]quinoline-5(6H), 5'(2'H)-pyrimidine]-2',4',6'(1'H,3'H)trione is obtained. MS (EI) m/z 450 (M⁺), 451, 450, 365, 364, 335, 319, 277, 225, 204, 165.

Example 39 rel-4-[(2R,4S,4aS)-1,1',2,3',4,4',4a,6'-Octahydro-2-4-dimethyl-2',4',6'-trioxospiro[[1,4]oxazino[4,3-a]quinoline-5(6H), 5(2'H)-pyrimidin]-9-yl]benzonitrile

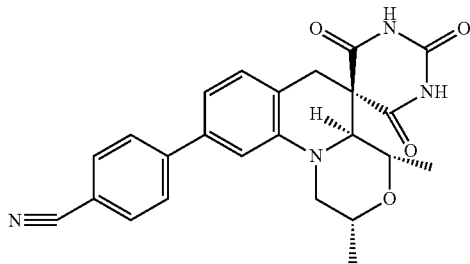

In a manner similar to that described for Example 34, 25 mg (24%) of rel-4-[(2R,4S,4aS)-1,1'-2,3',4,4',4a,6'-octahydro-2-4-dimethyl-2',4',6'-trioxospiro[[1,4]oxazino[4,3-a]quinoline-5(6H), 5(2'H)-pyrimidin]-9-yl]benzonitrile is obtained. ¹H NMR (400 MHz, CD₃OD) δ 1.05, 1.25, 2.90, 3.15, 3.7-3.85, 4.15, 6.91, 7.03, 7.07, 7.80.

Example 40 rel-(2R,4S,4aS)-1,2,4,4a-Tetrahydro-2,4-dimethyl-9-[4-(methylsulfonyl)phenyl]spiro[[1,4]oxazino[4,3-a]quinoline-5(6H), 5'(2'H)-pyrimidine]-2',4',6'(1'H,3'H)-trione

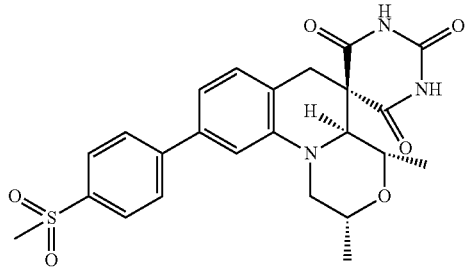

In a manner similar to that described for Example 34, 33 mg (28%) rel-(2R,4S,4aS)-1,2,4,4a-tetrahydro-2,4-dimethyl-9-[4-(methylsulfonyl)phenyl]spiro[[1,4]oxazino[4,3-a]quinoline-5(6H), 5'(2'H)-pyrimidine]-2',4',6'(1'H,3'H)-trione is obtained. MS (EI) m/z 483 (M⁺), 484, 483, 440, 398, 397, 368, 352, 312, 310, 204.

Example 41 rel-(2R,4S,4aS)-1,2,4,4a-Tetrahydro-2,4-dimethyl-9-(4-pyridinyl)spiro[[1,4]oxazino[4,3-a]quinoline-5(6H), 5'(2'H)-pyrimidine]-2',4',6'('H,3'H)-trione

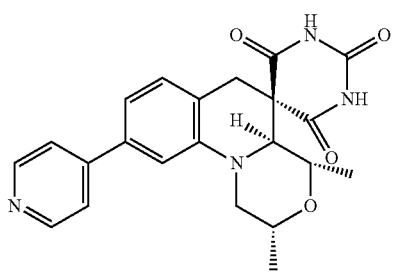

In a manner similar to that described for Example 34, 12 mg (12%) of rel-(2R,4S,4aS)-1,2,4,4a-tetrahydro-2,4-dimethyl-9-(4-pyridinyl)spiro[[1,4]oxazino[4,3-a]quinoline-5(6H), 5'(2'H)-pyrimidine]-2',4',6'('H,3'H)-trione is obtained IR (diffuse reflectance) 2984, 2837, 2705 (b), 2660 (b), 2649 (b), 2626 (b), 2611 (b), 1748, 1722 (s), 1693 (s), 1601, 1408, 1358, 1350, 1214, cm⁻¹.

Example 42 rel-Methyl (2R,4S,4aS)1,1'-2,3',4,4a,6'-Octahydro-2,4-dimethyl-2',4',6'-trioxospiro[[1,4]oxazino[4,3-a]quinoline-5(6H), 5'(2'H)-pyrimidine-9-carboxylate

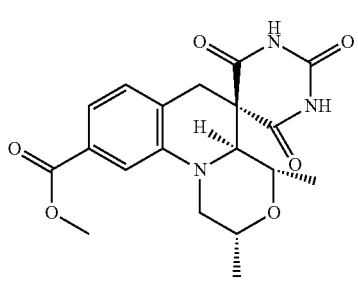

A mixture of 9-bromo-1,2,4,4a-tetrahydro-2,4-dimethyl-spiro[[1,4]piperazino[4,3-a]quinoline-5(6H), 5'(2'H)-pyrimidine]-2',4',6'(1'H,3'H)-trione [as prepared according to Example 10 (Steps 1-3) except using 4-bromo-2-fluorobenzaldehyde as the starting aldehyde] (1.47 mmol), tetrakis(triphenylphosphine) palladium (0.44 mmol), N,N,N-diisopropylethylamine (4.4 mmol), dimethylformamide (8 mL) and methanol (2 mL) is charged with carbon monoxide (600 psi) in a steel bomb and heated to 100° C. for 72 h. The mixture is cooled to room temperature, and the bomb is evacuated. The mixture is diluted with methanol and filtered. The filtrate is concentrated to give a residue, which is purified by silica gel chromatography using 20% ethyl acetate in CH₂Cl₂ as the eluent to give 26 mg (6%) of the desired product. ¹H NMR (400 MHz, Acetone-d₆) δ 1.05, 1.24, 3.0, 3.15, 3.45, 3.6, 3.7, 3.85, 4.15, 7.06, 7.27, 7.44.

Example 43 rel-Methyl (2R,4S,4aS)1,1'-2,3',4,4a,6'-Octahydro-2,
4-dimethyl-2',4',6'-trioxospiro[[1,4]oxazino[4,3-a]
quinoline-5(6H),5'(2'H)-pyrimidine]-8-carboxylate

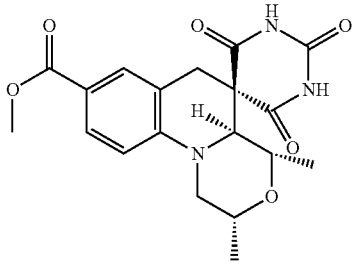

In a manner similar to that described for Example 42, except starting with 8-bromo-1,2,4,4a-tetrahydro-2,4-dimethylspiro[[1,4]piperazino[4,3-a]quinoline-5(6H), 5'(2'H)-pyrimidine]-2',4',6'(1'H,3'H)-trione (from Example 13), 110 mg (16%) of the title compound is obtained: ¹H NMR (400 MHz, CDCl₃) δ 1.05, 1.26, 3.05, 3.1, 3.2, 3.6-3.85, 3.86, 4.05, 6.95, 7.33, 7.7, 8.9, 9.6.

Example 44

1,2,3,3',4,4',4a,6'-Octahydro-2',4',6'-trioxospiro[1H-pyrazino[1,2-a]quinoline-5(6H), 5'(2'H)-pyrimidine-8-carbonitrile monohydrochloride

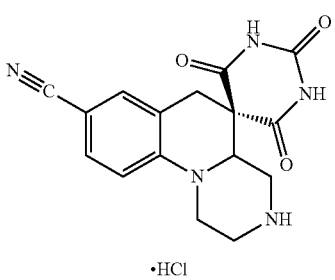

A suspension of 1,1-dimethylethyl 8-cyano-1,1',2,3',4,4', 4a,6'-octahydro-2',4',6'-trioxospiro[3H-pyrazino[1,2-a] quinoline-5(6H), 5'(2'H)-pyrimidine]-3-carboxylate, from Example 29, (2.48 g, 5.83 mmol) is stirred in 4 N HCl in dioxane (23 mL) for 1 h. The system is then purged with N₂, and the resulting solid is isolated by filtration. The white solid is triturated with dioxane and dried (20 Torr, 110° C.) to afford 1.77 g (84%) of the hydrochloride salt. ¹H NMR (400 MHz, DMSO-d₆) δ 11.52, 11.46, 9.31, 9.10, 7.52, 7.47, 7.07, 4.33, 4.14, 3.38, 3.31, 3.27, 3.15, 3.04, 2.94, 2.78.

Example 45

2,3,4,4a-Tetrahydro-8-nitrospiro[1H-pyrazino[1,2-a]
quinoline-5(6H), 5'(2'H)-pyrimidine]-2',4',6'(1'H,
3'H)-trione monohydrochloride

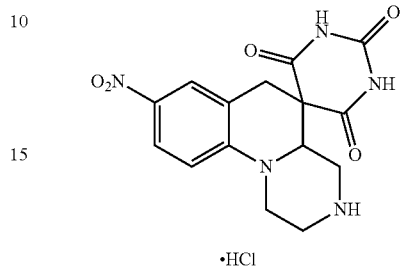

In a similar manner as described in Example 47, 996 mg (95%) of the title compound is obtained. ¹H NMR (400 MHz, DMSO-d₆) δ 11.59, 11.48, 9.20, 9.03, 8.00, 7.95, 7.09, 4.41, 4.25, 3.52, 3.44, 3.29, 3.11, 3.01, 2.86.

Example 46

Protocol for Preparing Various Cyclic Secondary
Amine Analogues Via Parallel Synthesis

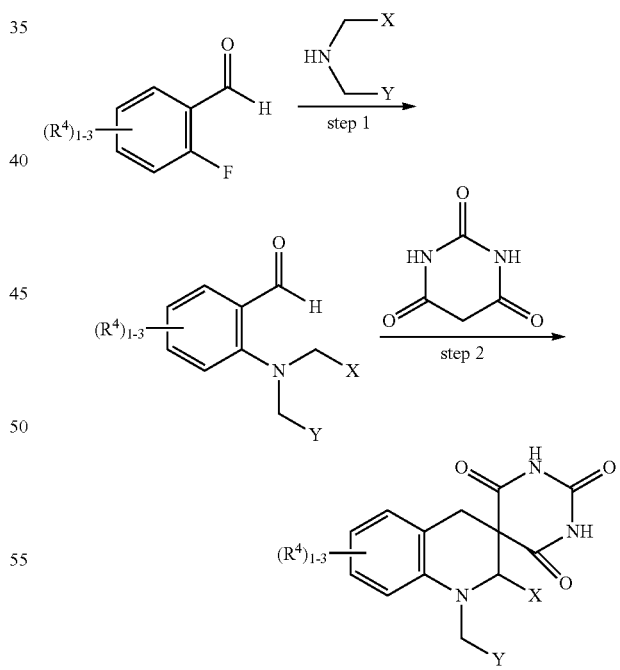

Step 1

An 8 mL screw-cap vial is charged 0.50 mmol of the desired amine followed by 0.7 mL (0.25 mmol) of a 0.35 M stock solution of the appropriate aldehyde in acetonitrile followed by 275 mg (2.0 mmol) of solid potassium carbonate. The vials are tightly capped and then heated at 100° C. in a shaker block for 35 h. The cooled reactions are filtered into 20 mL vials containing 780 mg of Dowex p-SO₃H resin (5.2 meq/g washed and dried). The vials are shaken at RT for 30-45 min, and then filtered into pre-tared 20 mL vials. The resin is washed with 85% CH₃OH in H₂O (4×1.5 mL). The resin is then eluted into pre-tared 20 mL vials using 2N pyridine in methanol. Both the wash and elute vials are concentrated on a Thermo Savant at 50° C. overnight. The vials are weighed and the vials containing the product are carried forward.

Step 2

To the vials containing the product from Step 1, is added one equivalent (as determined by the mmols of the products from Step 1) of a 0.2 M stock suspension of barbituric acid in n-butanol. An additional 1 mL of n-butanol is added to each vial. The vials are tightly capped and heated at 100° C. in a shaker block for 18 h. The cooled reaction mixtures are diluted with approximately 4 mL of a 1:1 acetonitrile/methanol solution. To each vial is added 1.5 g of Dowex SBR strongly basic resin (4.4 meq/g washed). The vials are shaken at RT for 2-3 h at RT and filtered. The resin is washed with a small amount of 1:1 acetonitrile/methanol solution. The resin is the eluted into pre-tared 20 mL vials using 10% TFA in to acetonitrile solution (5×2 mL). The vials are concentrated on the Thermo Savant at RT overnight to give the final products. The weights of the final products are determined. The purity and mass identification of the final products is determined by LC/MS techniques.

Example 47

Protocol for Preparing Various Analogues Using Commercially Available Benzaldehyde Derivatives and Cis-2,6-Dimethylmorpholine

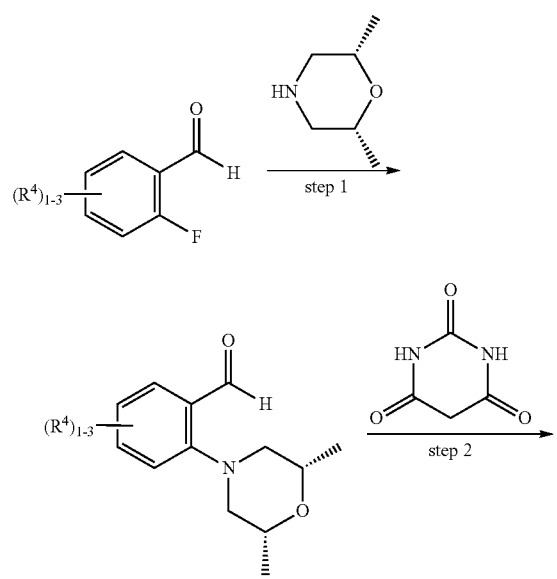

-continued

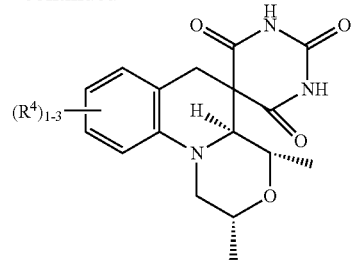

Step 1

An 8 mL screw-cap vial is charged 0.25 mmol of the desired aldehyde followed by 1.4 mL (0.5 mmol) of a 0.35 M stock solution of cis-2,6-dimethylmorpholine in acetonitrile followed by 275 mg (2.0 mmol) of solid potassium carbonate. The vials are tightly capped and then heated at 100° C. in a shaker block for 35 h. The cooled reactions are filtered into 20 mL vials containing 780 mg of Dowex p-SO₃H resin (5.2 meq/g washed and dried). The vials are shaken at RT for 30-45 min, and then filtered into pre-tared 20 mL vials. The resin is washed with 85% CH₃OH in H₂O (4×1.5 mL). The resin is then eluted into pre-tared 20 mL vials using 2N pyridine in methanol. Both the wash and elute vials are concentrated on a Thermo Savant at 50° C. overnight. The vials are weighed and the vials containing the product are carried forward.

Step 2

To the vials containing the product from Step 1, is added one equivalent (as determined by the mmols of the products from Step 1) of a 0.2 M stock suspension of barbituric acid in n-butanol. An additional 1 mL of n-butanol is added to each vial. The vials are tightly capped, and heated at 100° C. in a shaker block for 18 h. The cooled reaction mixtures are diluted with approximately 4 mL of a 1:1 acetonitrile/methanol solution. To each vial is added 1.5 g of Dowex SBR strongly basic resin (4.4 meq/g washed). The vials are shaken at RT for 2-3 h at RT and filtered. The resin is washed with a small amount of 1:1 acetonitrile/methanol solution. The resin is the eluted into pre-tared 20 mL vials using 10% TFA in acetonitrile solution (5×2 mL). The vials are concentrated on the Thermo Savant at RT overnight to give the final products. The weights of the final products are determined. The purity and mass identification of the final products is determined by LC/MS techniques.

Commercially Available Benzaldehyde derivates include, but are not limited to, 2-Fluorobenzaldehyde; 2,3,4,5,6-Pentafluorobenzaldehyde; 2-Chloro-6-fluoro benzaldehyde; 2-Fluoro-6-chlorobenzaldehyde; 2,3-Difluorobenzaldehyde; 2,6-Difluorobenzaldehyde; 2,4-Difluorobenzaldehyde; 2,5-Difluorobenzaldehyde; 2-Fluoro-5-nitrobenzaldehyde; 3-Cyano-4-dimethylamino-2-fluoro-benzaldehyde; 6-(Dimethylamino)-2-fluoro-3-formylbenzonitrile; 2-Fluoro-4,5-dimethoxybenzaldehyde; 3,4-Dimethoxy-6-fluoro-benzaldehyde; 2,3,6-Trifluorobenzaldehyde; 2,4,5-Trifluorobenzaldehyde; 2,4,6-Trifluorobenzaldehyde; 2,3,4-Trifluorobenzaldehyde; 2-Fluoro-3-(trifluoromethyl)benzaldehyde; 2-Fluoro-6-(trifluoromethyl)benzaldehyde; 2-Fluoro-4-(trifluoromethyl)benzaldehyde; 2-Fluoro-5-(trifluoromethyl)benzaldehyde; 2-Fluoro-5-bromobenzaldehyde; 5-Bromo-2-fluorobenzaldehyde; 2-Fluoro-5-methoxybenzaldehyde; 6-Fluoro-m-anisaldehyde; 2,3,5-Trifluorobenzaldehyde; 2-Fluoro-4-bromo-benzaldehyde; 4-Bromo-2-fluoro benzaldehyde; 2-Fluoro-4-chlorobenzaldehyde; 4-Chloro-2-fluoro-benzaldehyde; 2,3,5,6-Tetrafluorobenzaldehyde; 2,3-Difluoro-4-(trifluoromethyl)benzaldehyde; 2-Fluoro-4-methoxy-benzaldehyde; 2-Fluoro-p-anisaldehyde; 4-Methoxy-2-fluorobenzaldehyde; 2-Fluorovanillin; 2-Fluoro-6-hydroxybenzaldehyde; 2-Fluoro-6-methoxybenzaldehyde; 3-Chloro-2,6-difluorobenzaldehyde; 2,6-Difluoro-3-methylbenzaldehyde; 3-Chloro-2-fluoro-6-(trifluoromethyl)benzaldehyde; 2-Chloro-6-fluoro-3-methylbenzaldehyde; 6-Chloro-2-fluoro-3-methylbenzaldehyde; 2-Chloro-3,6-difluorobenzaldehyde; 3-Chloro-2-fluoro-5-(trifluoromethyl)benzaldehyde; 3-Chloro-2-fluorobenzaldehyde; 2,3-Difluoro-4-methylbenzaldehyde; 3-Fluoro-4-formylbenzeneboronic acid; 2-Fluoro-5-methylbenzaldehyde; 2,3-Difluoro-6-methoxybenzaldehyde; 3-Chloro-6-fluoro-2-(trifluoromethyl)benzaldehyde; 3-Fluoro-4-biphenylcarboxaldehyde; 2,3,4,5-Tetrafluorobenzaldehyde; 2-Fluoro-5-iodobenzaldehyde; 2,4-Dibromo-6-fluorobenzaldehyde; 3,5-Dibromo-2-fluorobenzaldehyde; 2-Fluoro-4-methylbenzaldehyde; 4-Bromo-2,6-difluorobenzaldehyde; 4-Chloro-2,6-difluorobenzaldehyde; 4-Bromo-2,3,6-trifluorobenzaldehyde; 4-Chloro-2,3,6-trifluorobenzaldehyde; 5-Chloro-2-fluorobenzaldehyde.

Example 48 rel-(2R,4S,4aS)-2,4-diethyl-1,2,4,4a-tetrahydro-8-nitrospiro[[1,4]oxazino[4,3-a]quinoline-5(6H),5'(2'H)-pyrimidine]-2',4',6'(1'H, 3'H)-trione

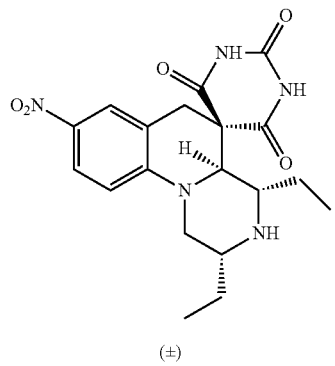

(±)

Step 1: Preparation of
4-Benzyl-cis-2,6-diethylmorpholine

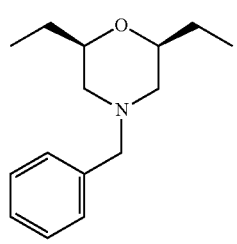 [SMILES: CC[C@@H]1CN(Cc2ccccc2)C[C@H](CC)O1]

(DL+meso)-N-benzyl-1,1'-iminobis-2-butanol (18.8 g, 74.6 mmol), described in *J. Heterocycl. Chem;* 20; 1983; 1681-1685, is cooled to 0° C. and treated with 70% $H_2SO_4$ (5 eq w/w) with stirring. The mixture is sealed in a glass pressure tube and heated to 160° C. for four days. The mixture is basified with 6.0M NaOH until the solution is basic and is extracted with MTBE (200 mL). The ethereal layer is washed with water and brine. The organic layer is dried over $Na_2SO_4$ and filtered, and the solvent is removed by rotary evaporation. The product is purified on a Biotage Flash 75L+ using 7% MTBE in heptane as eluent. The product containing fractions are pooled and the solvent is removed by rotary evaporation. The product is dried under vacuum yielding a golden oil.

Step 2: Preparation of 2-(cis-2,6-Diethylmorpholin-4-yl)-5-nitrobenzaldehyde

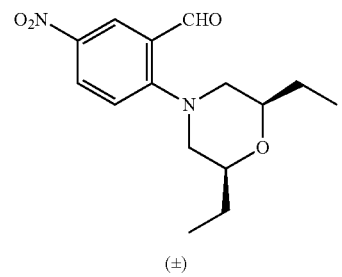 [SMILES: CC[C@@H]1CN(c2ccc([N+](=O)[O-])cc2C=O)C[C@H](CC)O1]

(±)

1-Chloroethyl chloroformate (2.18 mL, 20 mmol, Aldrich) is added to a solution of 4-benzyl-cis-2,6-dimethylmorpholine in $CH_2Cl_2$ (45 mL) with stirring in an ice bath. The solution is allowed to warm to room temperature and stirred for 21 hours. The solvent is removed by rotary evaporation and the residue is dissolved in methanol (25 mL). This solution was heated to reflux for 3 hours and the methanol is removed by rotary evaporation. The product is dissolved in $CH_3CN$ (40 mL) and treated with N,N-diisopropylethylamine (2.0 mL, 11.5 mmol, Aldrich). $K_2CO_3$ (1.5 g, 11 mmol, Mallinkrodt) and 2-fluoro-5-nitrobenzaldehyde (1.9 g, 1.13 mmol, Oakwood) is added and the mixture is heated at 60° C. for 21 hours. N,N,N'-trimethylethylenediamine (0.4 mL) is added and the reaction is stirred an additional 45 minutes @ 60° C. The mixture is filtered and the solvent is removed by rotary evaporation. The residue is taken up in $CH_2Cl_2$ (200 mL) and washed 2× with 1.0 M HCl, 1× with saturated $NaHCO_3$ and 1× with brine (150 mL each). The organic layer is dried over $Na_2SO_4$ and filtered. The solvent is removed by rotary evaporation and the product is purified on a Biotage Flash 40M+ using a 15% EtOAc in heptane as eluent. The product containing fractions are pooled and the solvent is removed by rotary evaporation. The product is dried under vacuum yielding a yellow solid.

Step 3

2-(cis-2,6-Diethylmorpholin-4-yl)-5-nitrobenzaldehyde (1.58 g, 5.39 mmol) is combined with barbituric acid (767 mg, 5.39 mmol, Aldrich) in a flask with MeOH (17 mL). The sealed reaction is stirred with heating at 80° C. overnight. The solvent is removed by rotary evaporation and the product is purified on a Biotage Flash 40M+ using a 10% MTBE in $CH_2Cl_2$ as eluent. The product is dried under vacuum and re-crystallized from $CH_3OH$/heptane. The large crystals are crushed and dried under vacuum @100° C. yielding 1.04 g (48%) of bright yellow crystalline solid. $^1$H NMR (400 MHz, DMSO-d$_6$) δ ppm 0.86, 0.97, 1.08, 1.24, 1.45, 1.58, 2.84, 3.03, 3.34, 3.60, 3.97, 4.26, 7.01, 7.84, 7.98, 11.56, 11.87.

Example 49 rel-(2R,4R,4aR)-1,2,4,4a-tetrahydro-4-methyl-8-nitro-2-(trifluoromethyl)spiro[[1,4]oxazino[4,3-a]quinoline-5(6H), 5'(2'H)-pyrimidine]-2',4',6'(1'H,3'H)-trione

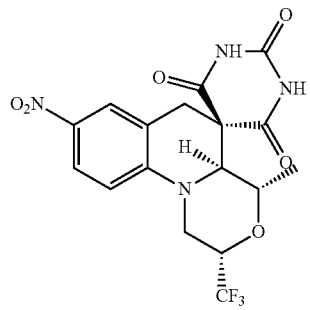

(±)

Step 1: Preparation of 3-(Benzylamino)-1,1,1-trifluoropropan-2-ol

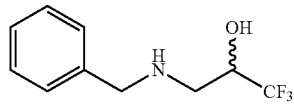

Lithium triflate was suspended in CH$_3$CN (15 mL) and the mixture is cooled to −10° C. 2-(Trifluoromethyl)oxirane is added and the suspension is allowed to warm to RT with stirring. Benzylamine (6.33 mL, 58 mmol, Aldrich) is added all-at-once and the resultant solution is stirred for 25 minutes. The reaction is quenched by pouring into CH$_2$Cl$_2$ (200 mL) and washing 3× with H$_2$O (200 mL). The organic layer is dried over Na$_2$SO$_4$ and filtered. The product is purified on a Biotage Flash 75L using 20:70:10 CH$_2$Cl$_2$: pentane: triethylamine as eluent. The product containing fractions are pooled and the solvent is removed by rotary evaporation. The product is dried under vacuum at 100° C. yielding a white crystalline solid.

Step 2: Preparation of 4-Benzyl-2-methyl-6-(trifluoromethyl)morpholin-3-one

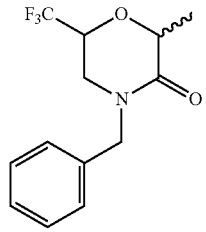 [SMILES: CC1OC(C(F)(F)F)CN(Cc2ccccc2)C1=O]

A solution of 3-(Benzylamino)-1,1,1-trifluoropropan-2-ol (2.68 g, 12.3 mmol) and triethylamine (1.7 mL, 12.2 mmol) in CH$_2$Cl$_2$ is cooled to 0° C. The solution is treated drop wise with 2-bromopropanoyl chloride (1.2 mL, 12 mmol, Aldrich) and stirred for 5 minutes. The solution is diluted to 100 mL with CH$_2$Cl$_2$ and washed sequentially with 1.0M HCl, saturated NaHCO$_3$, and brine (100 mL each). The organic layer is dried over Na$_2$SO$_4$ and filtered. The solvent is removed by rotary evaporation yielding (N-benzyl-2-bromo-N-(3,3,3-trifluoro-2-hydroxypropyl)propanamide as a golden oil. Dry NaH is suspended in dry, inhibitor free THF (25 ml) in a flame dried flask and the mixture is cooled to 0° C. with stirring on an ice bath. The N-benzyl-2-bromo-N-(3,3,3-trifluoro-2-hydroxypropyl)propanamide (4.25 g, 12 mmol) is added as a solution in dry, inhibitor free THF (25 ml) and the resultant suspension is warmed to RT. After stirring for one hour the reaction is quenched with MeOH over an ice bath until no more gas evolved and the mixture is poured into 1.0M HCl (200 mL). The aqueous mixture is extracted into MTBE (200 mL) and the organic layer is washed with saturated NaHCO$_3$ and brine (200 mL each). The organic layer is dried over Na$_2$SO$_4$ and filtered, and the solvent is removed by rotary evaporation yielding an amber oil.

Step 3: Preparation of 4-Benzyl-cis-2-methyl-6-(trifluoromethyl)morpholine

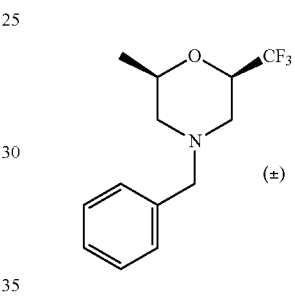

Dry LiAlH$_4$ (797 mg, 21 mmol, Aldrich) is suspended in dry, inhibitor free THF (15 ml) and treated with a solution of 4-benzyl-2-methyl-6-(trifluoromethyl)morpholin-3-one (2.73 g, 10 mmol) in dry, inhibitor free THF (15 ml). The mixture is heated to 60° C. with stirring for 30 minutes. The mixture is diluted with MTBE (25 mL) and quenched sequentially with H$_2$O (0.8 mL), 6.0M NaOH (0.8 mL) and H$_2$O (2.4 mL). The white slurry is filtered and the inorganic salts were washed with MTBE (200 mL). The solvent is removed by rotary evaporation and the product is purified in 3 portions on Biotage Flash 40M+ cartridges using a 10 minute linear gradient of 3%-10% MTBE in heptane. The products are combined and dried under high vacuum yielding a colorless oil.

Step 4: Preparation of 2-[cis-2-Methyl-6-(trifluoromethyl)morpholin-4-yl]-5-nitrobenzaldehyde

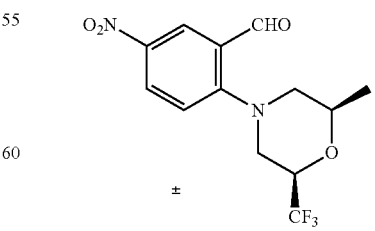

1-Chloroethyl chloroformate (292 μL, 2.68 mmol, Aldrich) is added to a solution of 4-benzyl-cis-2-methyl-6-(trifluoromethyl)morpholine (324 mg, 1.25 mmol) in CH$_2$Cl$_2$ (6 mL) with stirring in an ice bath. The solution is allowed to warm to room temperature and stirred for 16 hours. The solvent is removed by rotary evaporation and the residue is dissolved in methanol (6 mL). This solution is heated to reflux for 4 hours and the methanol is removed by rotary evaporation. The residue is dissolved in CH₃CN (5 mL) and treated with N,N-diisopropylethylamine (0.261 mL, 1.5 mmol, Aldrich). K₂CO₃ (190 mg, 1.37 mmol, Mallinkrodt) and 2-fluoro-5-nitrobenzaldehyde (254 mg, 1.5 mmol, Oakwood) are added and the mixture is heated at 60° C. for 36 hours. N,N,N'-trimethylethylenediamine (2.3 mL) is added and the reaction is stirred an additional 2 hours @60° C. The mixture is filtered and the solvent is removed by rotary evaporation. The residue is taken up in EtOAc (100 mL) and washed 2× with 1.0 M HCl, 1× with saturated NaHCO₃ and 1× with brine (75 mL each). The organic layer is dried over Na₂SO₄ and filtered. The solvent is removed by rotary evaporation and the product is purified on a Biotage Flash 25M+ using 20% EtOAc in heptane as eluent. The product containing fractions are pooled and the solvent is removed by rotary evaporation. The product is dried under vacuum at 100° C. yielding a yellow solid.

Step 5

2-[cis-2-methyl-6-(trifluoromethyl)morpholin-4-yl]-5-nitrobenzaldehyde (212 mg, 0.67 mol) is combined with barbituric acid (95 mg, 0.67 mmol, Aldrich) in a vial with MeOH (3 mL). The sealed reaction is heated to 80° C. on a shaker block for 21 hours and then the solvent is removed by rotary evaporation. The product is purified on a Biotage Flash 25M+ using a 26 minute linear gradient of 2.5%-10% MTBE in CH₂Cl₂ eluent. The product is dried under vacuum yielding a yellow-orange solid. ¹H NMR (400 MHz, DMSO-d₆) δ ppm 1.01, 2.93, 3.46, 3.66, 3.73, 4.04, 4.40, 4.48, 7.10, 7.88, 8.01, 11.63, 11.94.

Example 50 rel-(2R,4S,4aS)-1,2,4,4a-tetrahydro-4-methyl-8-nitro-2-propylspiro[[1,4]oxazino[4,3-a]quinoline-5(6H),5'(2'H)-pyrimidine]-2',4',6'(1'H,3'H)-trione

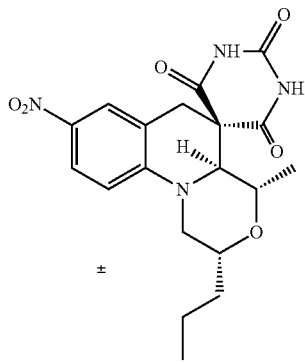

Step 1: Preparation of 2-(cis-2-Methyl-6-propylmorpholin-4-yl)-5-nitrobenzaldehyde

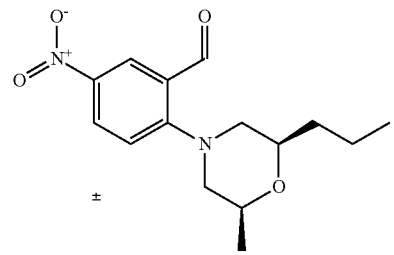 [SMILES: CCC[C@@H]1CN(c2ccc([N+](=O)[O-])cc2C=O)C[C@H](C)O1]

A mixture of cis-2-allyl-4-benzyl-6-methylmorpholine (520 m, 2.25 mmol), trifluoroacetic acid (0.5 mL, Aldrich) and 5% palladium on carbon (54 mg, 10% w/w, Aldrich) is sealed in a Parr bottle under 40 PSI of H₂, and is shaken for 17 hours. The mixture is filtered and the solvent removed by rotary evaporation yielding cis-2-methyl-6-propylmorpholine trifluoroacetate as a light golden oil. The oil is taken up in CH₃CN (8 mL) and treated with N,N-diisopropylethylamine (1.2 mL, 6.9 mmol, Aldrich). 2-Fluoro-5-nitrobenzaldehyde (419 mg, 2.48 mmol, Oakwood) is added and the mixture is shaken at 60° C. for 21 hours. N,N,N'-trimethylethylenediamine (1.0 mL) is added and the reaction is shaken for an additional 30 minutes @60° C. after which the solvent is removed by rotary evaporation. The residue is taken up in EtOAc (100 mL) and washed with 1.0 M HCl, saturated NaHCO₃ and brine (100 mL each). The organic layer is dried over Na₂SO₄ and filtered. The solvent is removed by rotary evaporation and the product is purified on a Biotage Flash 40M+ using 20% EtOAc in heptane as eluent. The product containing fractions are pooled and the solvent is removed by rotary evaporation. The product is dried under vacuum at 60° C. yielding a yellow oil.

Step 2

2-(cis-2-methyl-6-propylmorpholin-4-yl)-5-nitrobenzaldehyde (446 mg, 1.53 mol) is combined with barbituric acid (217 mg, 1.53 mmol, Aldrich) in a vial with MeOH (6 mL). The sealed reaction is heated to 80° C. on a shaker block for 19 hours and then the solvent is removed by rotary evaporation. The product is purified 2× on a Biotage Flash 75M using 10% MTBE in CH₂Cl₂ eluent. The product is dried under vacuum at 100° C. yielding a yellow-orange solid. ¹H NMR (400 MHz, ACETONITRILE-D3) δ ppm 0.95, 1.00, 1.47, 3.04, 3.34, 3.56, 3.95, 4.14, 6.85, 7.77, 8.02, 9.19.

Example 51

(2S,4S,4aS)-1,2,4,4a-tetrahydro-2,4-dimethyl-8-nitrospiro[[1,4]oxazino[4,3-a]quinoline-5(6H),5'(2'H)-pyrimidine]-2',4',6'(1'H,3'H)-trione

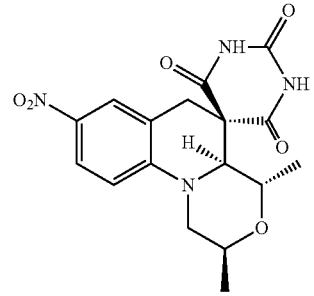

Step 1: Preparation of
(2S,6S)-4-Benzyl-2,6-dimethylmorpholine

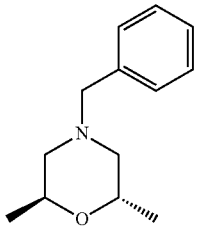

(2S,6S)-4-benzoyl-2,6-dimethylmorpholine (759 mg, 3.46 mmol) is dissolved in anhydrous THF (40 mL) and treated with LiAlH$_4$ (1.0M in THF, 6.9 mL, Aldrich). The mixture is stirred with heating at 55° C. for 18 hours. An additional equivalent of LiAlH$_4$ is added and the mixture is stirred with heating at 55° C. for an additional 6 hours. The reaction is quenched by adding water (0.4 mL) followed by 6.0M NaOH (0.4 mL) followed by water (1.2 mL). The white slurry is diluted with Et$_2$O and filtered. The inorganic salts are washed with and additional portion of Et$_2$O and the combined ethereal washes are dried over Na$_2$SO$_4$. The product is purified on a Biotage Flash 40M+ using a 15% Et$_2$O in pentane as eluent. The product containing fractions are pooled and the solvent is removed by rotary evaporation. The product is dried under vacuum yielding a colorless oil.

Step 2: Preparation of 2-[(2S,6S)-2,6-Dimethylmorpholin-4-yl]-5-nitrobenzaldehyde

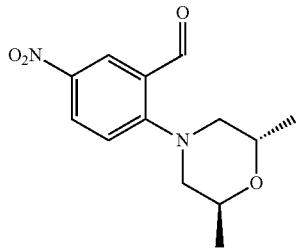 [SMILES: C[C@H]1CN(c2ccc([N+](=O)[O-])cc2C=O)C[C@H](C)O1]

1-Chloroethyl chloroformate (292 μL, 2.68 mmol, Aldrich) is added to a solution of (2S,6S)-4-benzyl-2,6-dimethylmorpholine (in CH$_2$Cl$_2$ (6 mL) with stirring in an ice bath. The solution is allowed to warm to room temperature and stirred for 2.5 hours. The solvent is removed by rotary evaporation and the residue is dissolved in methanol (6 mL). This solution is heated to reflux for 2.5 hours and the methanol is removed by rotary evaporation. The residue is dissolved in CH$_3$CN (5 mL) and treated with N,N-diisopropylethylamine (244 μL, 1.4 mmol, Aldrich). K$_2$CO$_3$ (190 mg, 1.37 mmol, Mallinkrodt) and 2-fluoro-5-nitrobenzaldehyde (230 mg, 1.36 mmol, Oakwood) are added and the mixture is heated at 60° C. for 21 hours. The mixture is filtered and the solvent is removed by rotary evaporation. The residue is dissolved in CH$_2$Cl$_2$ (100 mL) and washed sequentially with water (75 mL) and brine (75 mL). The organic layer is purified on a Biotage Flash 25M+ using a 40% EtOAc in heptane as eluent. The product containing fractions are pooled and the solvent is removed by rotary evaporation. The product is dried under vacuum yielding a yellow syrup.

Step 3

2-[(2S,6S)-2,6-Dimethylmorpholin-4-yl]-5-nitrobenzaldehyde (298 mg, 1.12 mmol) is combined with barbituric acid (159 mg, 1.12 mmol, Aldrich) in a vial with MeOH (2 mL). The sealed reaction is heated to 60° C. on a shaker block for 21 hours and then the solvent is evaporated. The product is purified on a Biotage Flash 40M+ using a 1:1 mixture of EtOAc and toluene as eluent Product is dried under vacuum yielding a yellow-orange solid. $^1$H NMR (400 MHz, DMSO-d$_6$) δ ppm 0.91, 1.24, 2.91, 3.56, 3.63, 3.83-3.91, 3.95, 4.07, 4.14-4.24, 6.85, 7.83, 7.98, 11.59, 11.89.

Example 52 rel-(2R,4S,4aS)-acetyl]-10-fluoro-1,2,4,4a-tetrahydro-2,4-dimethylspiro[[1,4]oxazino[4,3-a]quinoline-5(6H),5'(2'H)-pyrimidine]-2',4',6'(1'H,3'H)-trione

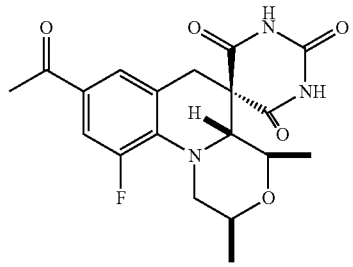

Step 1

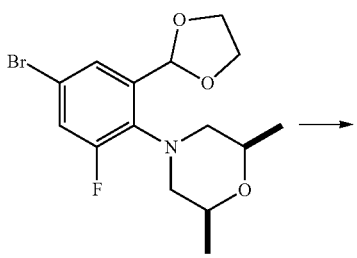

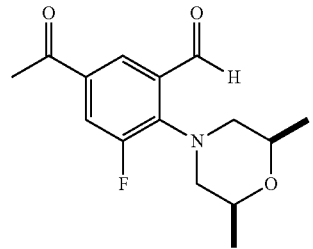

71
Step: 2
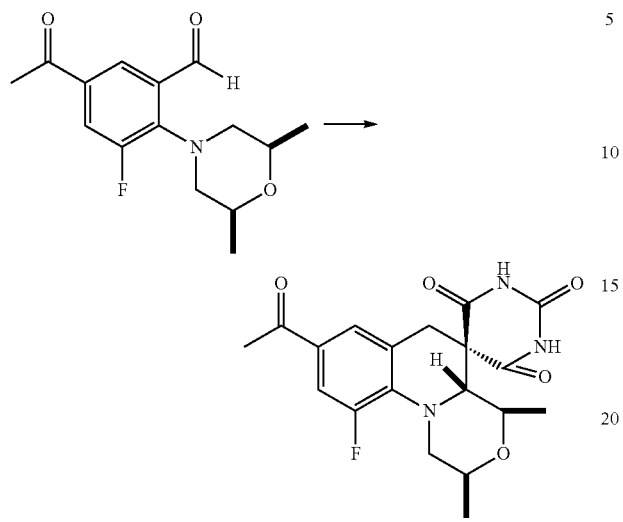
¹H NMR (400 MHz, DMSO-d₆) δ 11.9, 11.5, 7.55, 7.43, 4.00, 3.89, 3.75, 3.63, 3.54, 3.03, 2.93, 2.42, 1.11, 0.90.
Example 53
rel-(2R,4S,4aS)-8-acetyl-9,10-difluoro-1,2,4,4a-tetrahydro-2,4-dimethylspiro[[1,4]oxazino[4,3-a]quinoline-5(6H), 5'(2'H)-pyrimidine]-2',4',6'(1'H,3'H)-trione
Step 1
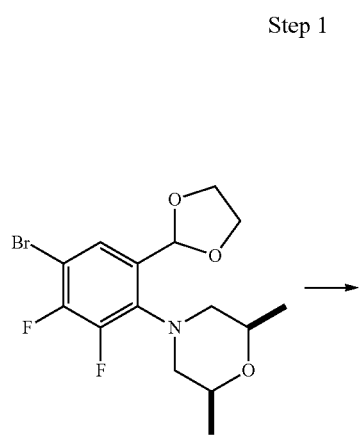
72
Step 2
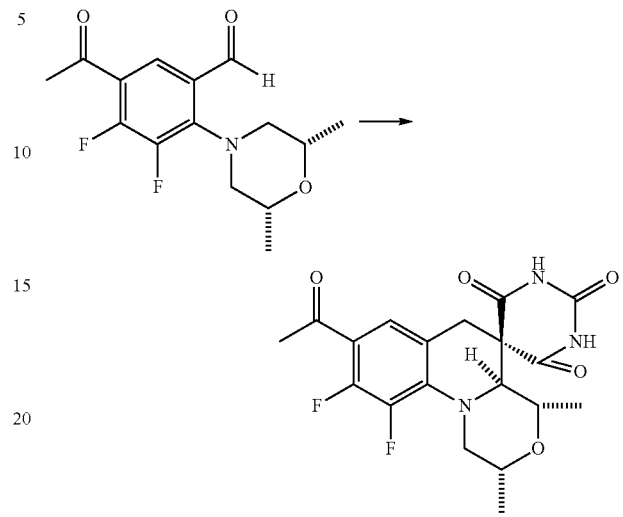
NMR (400 MHz, DMSO-d₆) δ 11.9, 11.5, 7.28, 4.10, 3.89, 3.74, 3.64, 3.56, 3.07, 2.85, 2.46, 1.12, 0.90.
Example 54
rel-(2R,4S,4aS)-10-fluoro-1,2,4,4a-tetrahydro-2,4-dimethyl-8-nitrospiro[[1,4]oxazino[4,3-a]quinoline-5(6H), 5'(2'H)-pyrimidine]-2',4',6'(1'H,3'H)-trione
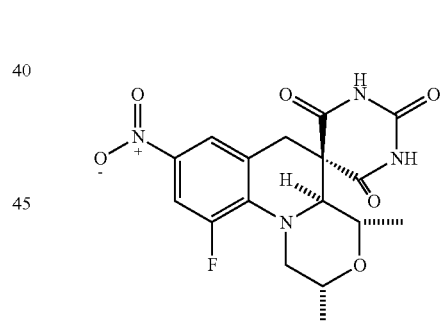
Step 1
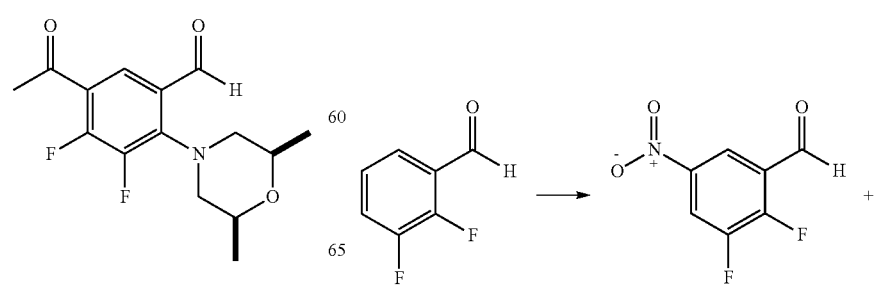

73
-continued

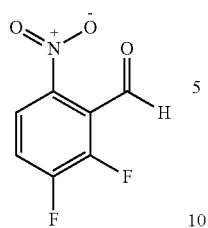

Nitric acid (2.8 ml) is slowly added dropwise to a solution of the 2,3 difluoro-benzaldehyde (2.0 g, Aldrich) in concentrated $H_2SO_4$ (14 ml) while cooling at 0° C. The resulting mixture is warmed to room temperature stirred for about 3 hours. The reaction is basified with sat'd $NaHCO_3$ and extracted with MTBE (2×), washed with brine, dried through $Na_2SO_4$, and concentrated by rotovap to produce a brownish red oil. The resulting oil is purified on a 90 g Biotage cartridge.

Step 2

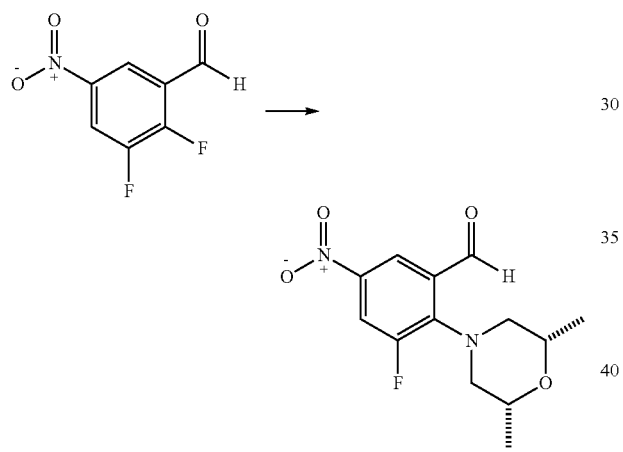

The nitro-difluoro-benzaldedhyde (0.94 g) is dissolved in $CH_3CN$ (10 ml) and $Et_3N$ (1.23 ml). The cis d-methyl-morpholine (0.78 ml) is added and the resulting mixture is refluxed for about 12 hours, cooled to room temperature and then to 0° C. for about 3 hours. The resulting mixture is filtered and the solids are rinsed with cold IPA and then dried at 100° C.

Step 3

74
-continued

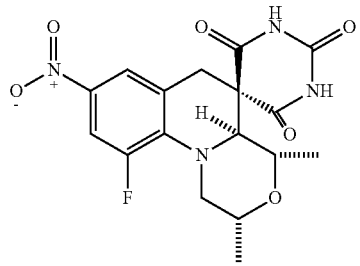

The fluoro-nitro aldehyde (0.5 g) and barbituric acid (0.243 g) are dissolved in IPA (8 ml) and refluxed for about 12 hours. The resulting mixture is cooled and stored at 0° C. for about 2 hours. The mixture is filtered and the solids are rinsed with cold IPA and dried at 90° C. for 2 days. $^1$H NMR (400 MHz, $CDCl_3$) δ 7.93, 7.78, 4.15, 3.97, 3.68, 3.10, 2.93, 1.13, 0.91.

Example 55

Oxadiazolyl Derivatives

Scheme 55.1

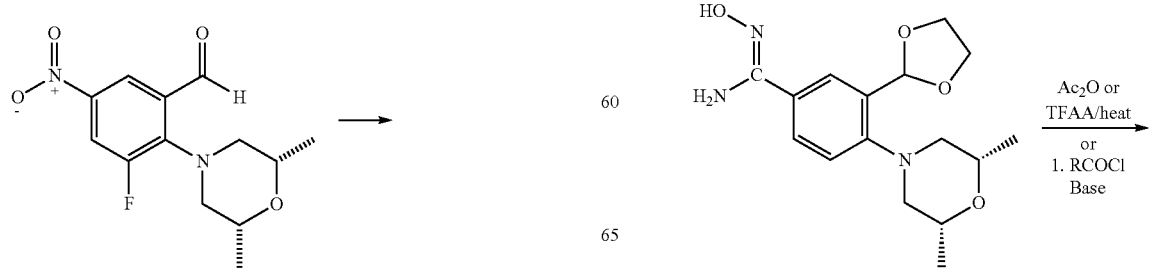

75
-continued
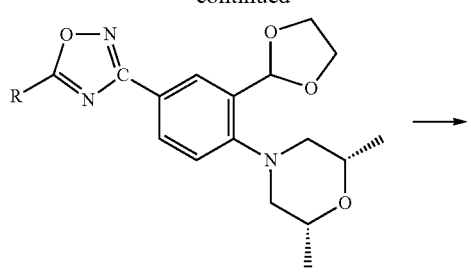
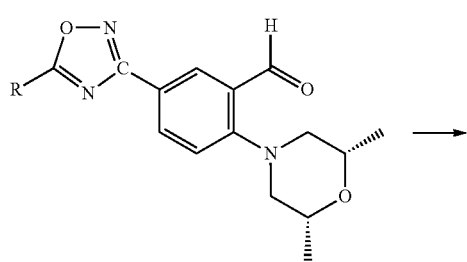
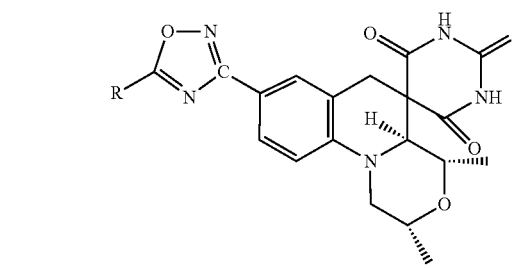
Racemate
Compounds Synthesized According to Scheme 1:
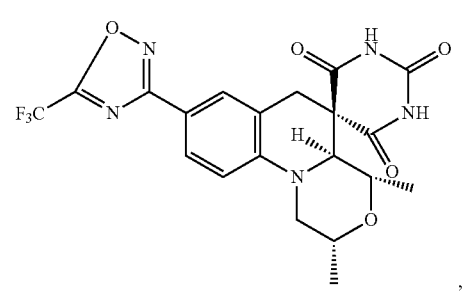
racemate
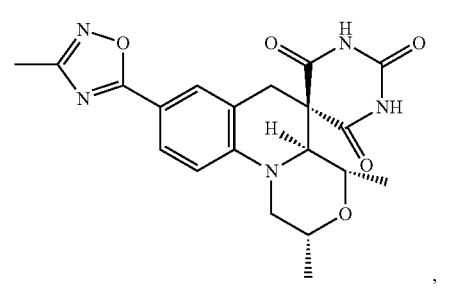
76
-continued
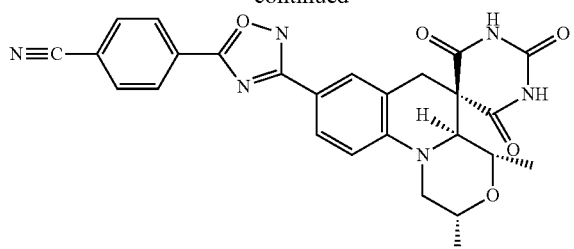
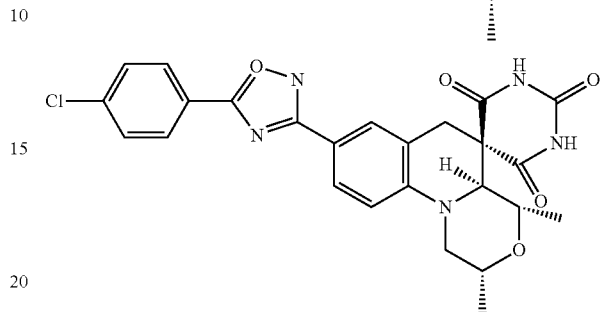
racemate
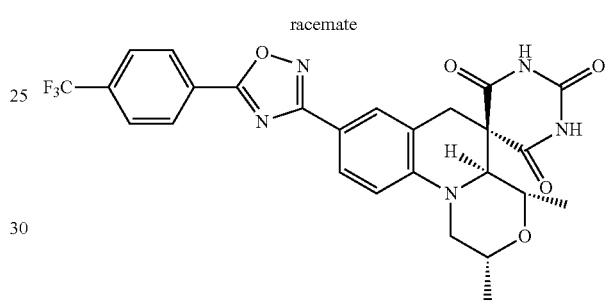
racemate
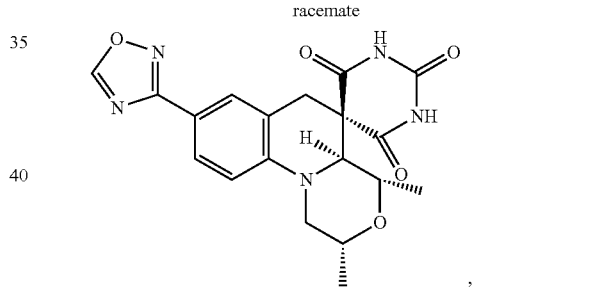
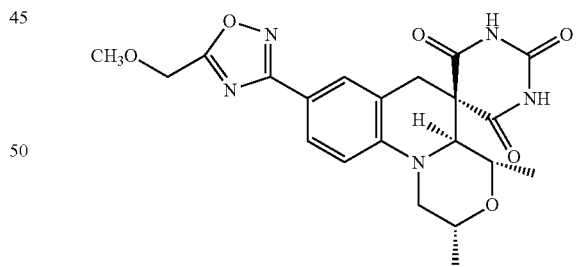
racemate
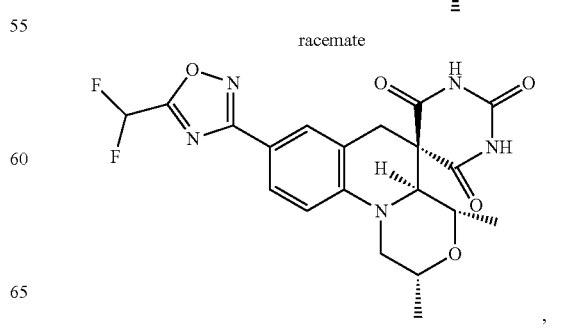

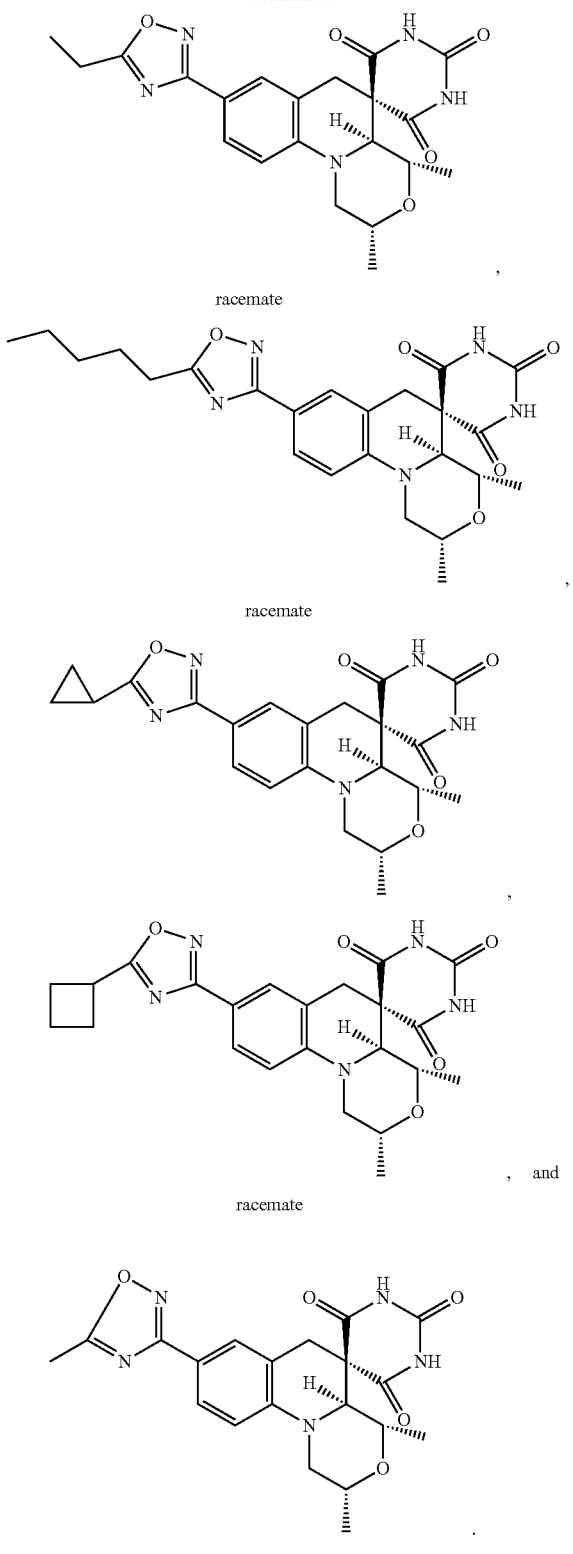
, racemate
, racemate
, racemate
, and racemate
.
IR (diffuse reflectance) 1750, 1724, 1708, 1617, 1596, 1487, 1451, 1409, 1374, 1346, 1335, 1196, 826, 788, 754 cm$^{-1}$. MS (EI) m/z (rel intensity) 411 (M$^+$,99), 412 (21), 411 (99), 326 (46), 296 (23), 284 (20), 283 (51), 280 (28), 240 (25), 239 (20), 238 (22). HRMS (ESI) calcd for $C_{20}H_{21}N_5O_5+H_1$ 412.1621, found 412.1631.
Scheme 55.2:
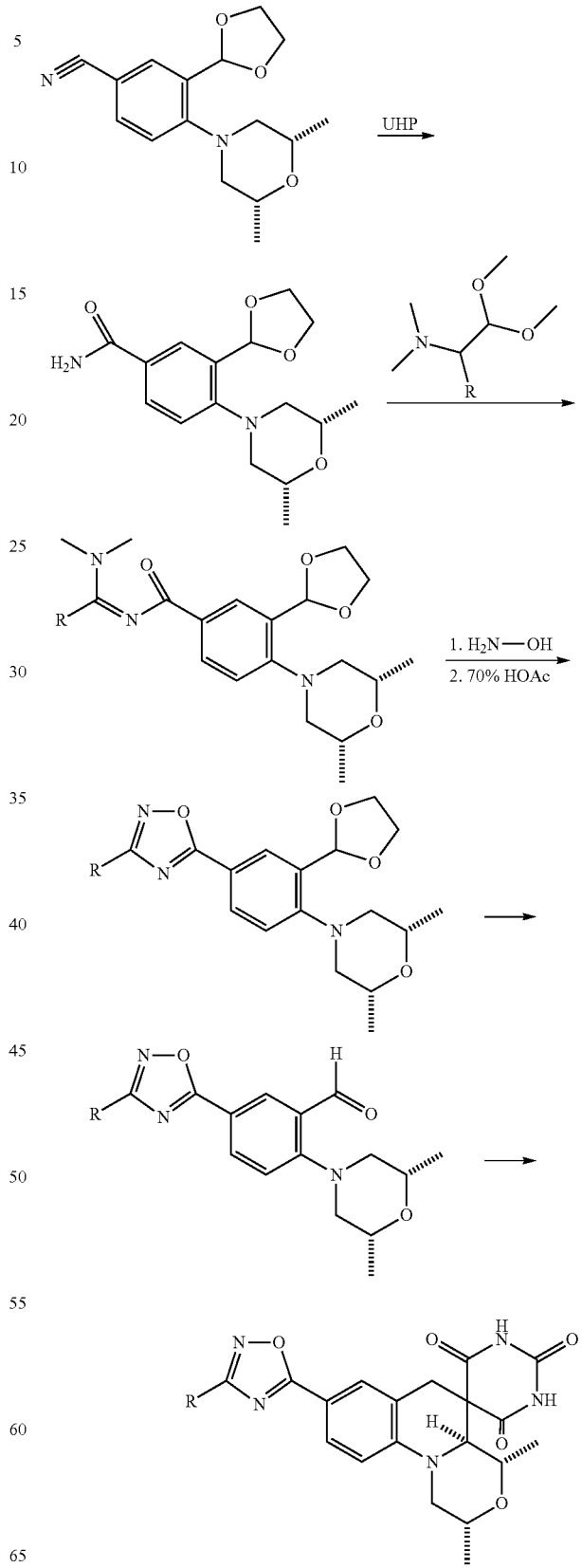

Example 56 rel-(2R,4S,4aS)-1,2,4,4a-tetrahydro-2,4-dimethyl-8-(3-methyl-1,2,4-oxadiazol-5-yl)spiro[[1,4]oxazino[4,3-a]quinoline-5(6H), 5'(2'H)-pyrimidine]-2',4',6'(1'H,3'H)-trione (R=CH₃ in scheme 55.2)

Step 1

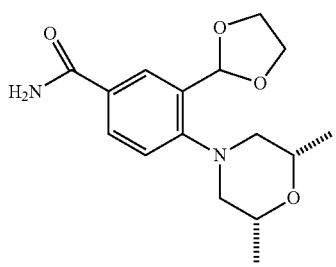 [SMILES: C[C@@H]1CN(c2ccc(C(N)=O)cc2C2OCCO2)C[C@H](C)O1]

Following a procedure reported in Syn Comm 23 (22) 3149-3155 (1993), urea hydrogen peroxide (UHP, 3.76 g, 0.04 mol) is added to a solution of nitrile (2.88 g, 0.01 mol), potassium carbonate (0.14 g, 0.001 mol) in acetone (~10 mL) and water (~10 mL). The yellow solution is stirred overnight at room temperature. The mixture is concentrated in vacuum to remove organic solvent and the white mixture is diluted with ~10 mL water. The mixture is stirred at room temperature for 1 h before filtration. The solid product is washed with water and vacuum dried at 60° C. overnight to give the desired amide product.

Step 2

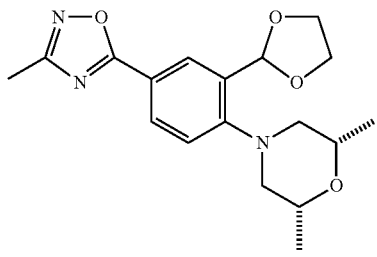

A mixture of amide acetal from step 1 (0.85 g, 2.77 mmol) and N,N-dimethylacetamide dimethylacetal (~3 mL) is heated to 120° C. for 1.5 h. The dark solution is cooled to room temperature and concentrated in vacuum at 70° C. to give 1.33 g of dark liquid which then is treated with a solution of aqueous 50% hydroxylamine (0.24 mL, 3.3 mmol) at room temperature for 30 minutes. The mixture is diluted with aqueous 10% sodium bicarbonate solution and dichloromethane. The phases are separated and the organic phase is concentrated in vacuum and to give a brown oily product.

Step 3

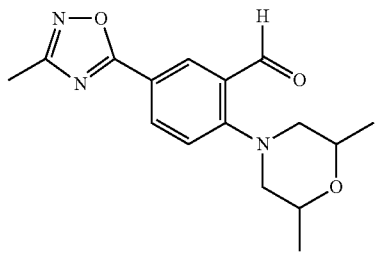

A solution of crude oxadiazole acetal from step 2, aqueous 2 N HCl (15 mL) and THF (15 mL) is heated to reflux for 30 minutes. The cooled solution is concentrated in vacuum to remove organic solvents. The aqueous phase is diluted with dichloromethane and aqueous sodium bicarbonate and the phases are separated. The organic phase is washed with water, dried (Na₂SO₄), concentrated in vacuum, and chromatographed on silica gel (20 mL), eluted with 20% ethyl acetate/dichloromethane to give an orange-yellow solid.

Step 4

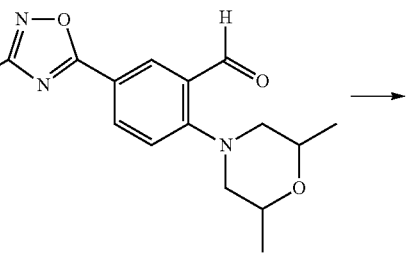

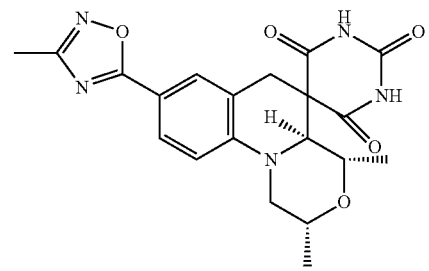

A mixture of the aldehyde from step 3, (0.545 g, 1.81 mmol) and barbituric acid (0.234 g, 1.82 mmol) in methanol (~8 mL) is slowly heated to reflux under nitrogen for 18 h. The solution is cooled to room temperature and concentrated to to give a yellow slurry mixture which is suspended in ether/hexane mixture. After cooling in an ice bath for 15 min, the mixture is filtered and the yellow solid is washed with ether to give the title compound. IR (diffuse reflectance) 3212, 1757, 1727, 1709, 1705, 1614, 1498, 1429, 1397, 1392, 1348, 1338, 1286, 1248, 755 cm$^{-1}$. MS (CI) m/z (rel intensity) 412 (MH⁺, 99), 414 (6), 413 (28), 412 (99), 411 (4), 410 (3), 116 (3), 114 (17), 98 (3), 96 (10), 59 (4). HRMS (ESI) calcd for $C_{20}H_{21}N_5O_5+H_1$ 412.1621, found 412.1630.

Example 57
Triazolyl Derivatives
Scheme 57.1 below illustrates an exemplary methodology for producing triazole derivatives.
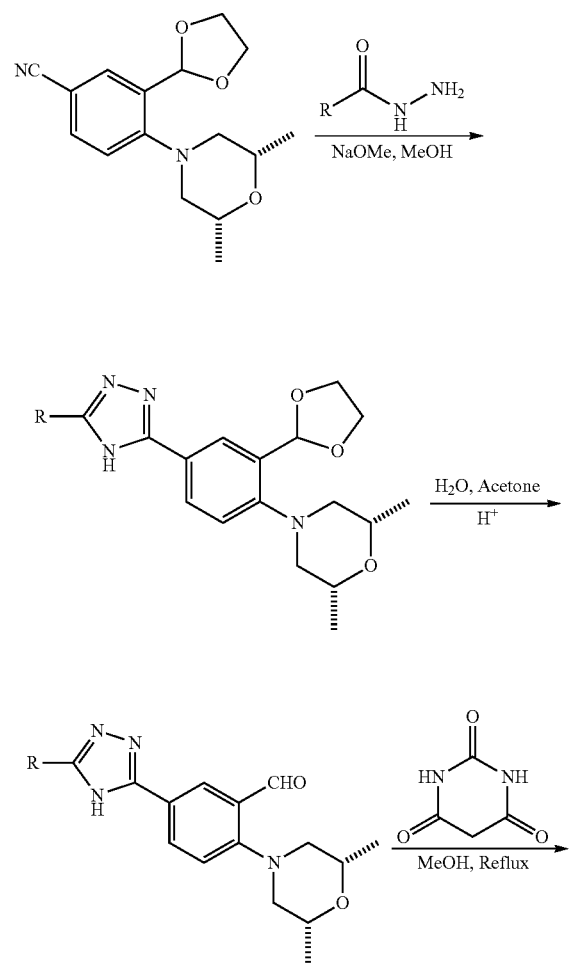
Example 58
Nitrogen-Coupled Amine/Het[1] Derivatives
Scheme 58.1 below illustrates an exemplary methodology for producing amine/het[1] derivatives
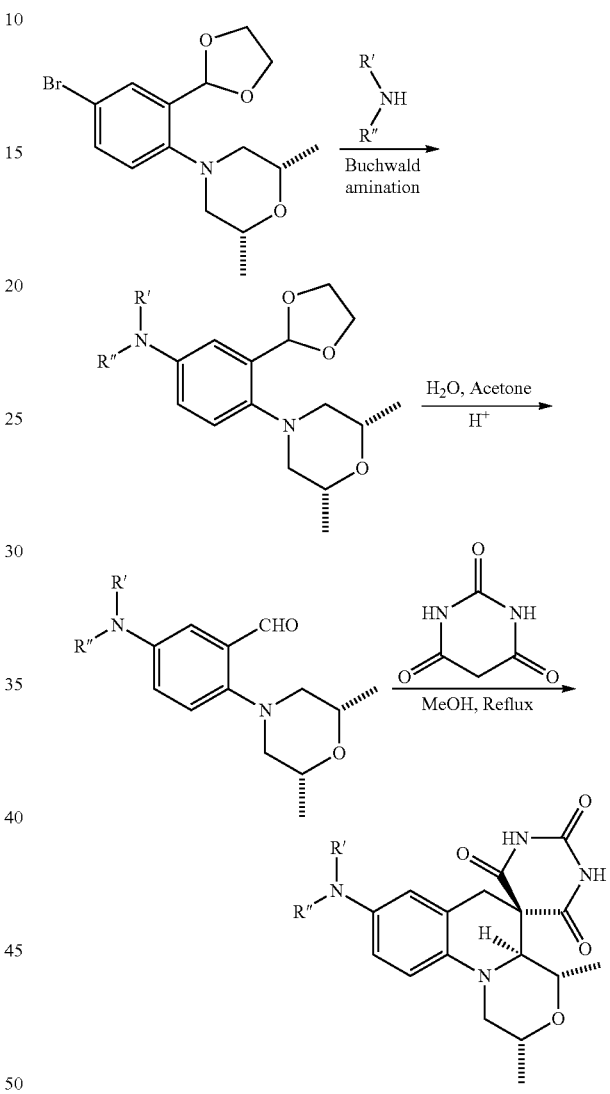
Example 59
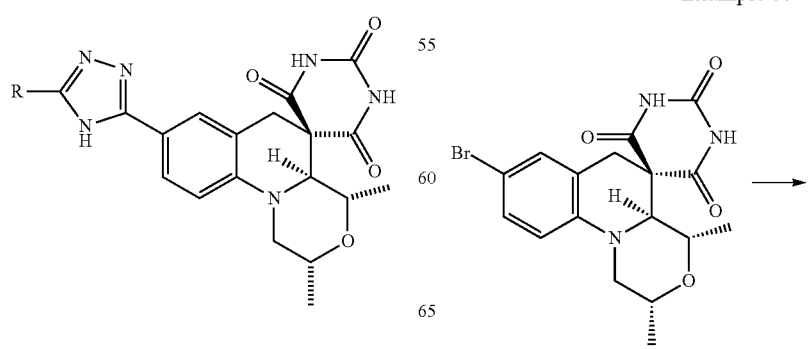

83
-continued

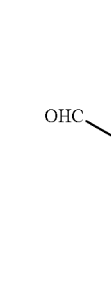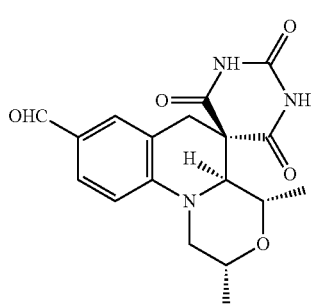

A solution of the bromo compound (5.0 g, 12.25 mmol) and tetramethyl ethylenediamine (6.0 ml, 4.62 g, 39.83 mmol) in dry THF (75 ml) is cooled in an ice bath under nitrogen. A 3M solution of MeMgBr in ether (10.0 ml, 30.0 mmol) is added and the mixture stirred for 15 min. The reaction is then cooled to −78° and a 1.7M solution of t-BuLi in pentane (25.0 ml, 42.5 mmol) is added. The reaction is monitored by hplc to follow the disappearance of the bromo derivative. Additional t-BuLi (7.0 ml, 11.9 mmol) is added after 1 hr. After 30 min dry DMF (10.0 ml, 9.44 g, 129.3 mmol) is added and the cooling bath removed and the reaction allowed to warm to ambient temp. Methanol (10 ml) is added and the solvent evaporated. The residual red gel/gum is partitioned between ethyl acetate (200 ml) and water (150 ml). The pH is adjusted to 4-5 with conc. HCl and the aqueous extracted further with ethyl acetate (2×250 ml). The organic extract is washed with water (2×150 ml), brine (100 ml), dried (MgSO4), filtered and evaporated to give an orange foam. Dissolution in ethyl acetate (25 ml) and filtration through silica gel (90 g) with ethyl acetate gives the aldehyde as an amber solid. $^1$H NMR (400 MHz, DMSO-$d_6$) δ 0.93, 1.16, 2.87, 2.97, 3.48, 3.53, 3.61, 3.86, 4.26, 4.26, 7.03, 7.40, 7.61, 9.62, 11.48, 11.83.

Example 60 rel-(2R,4S,4aS)-1,2,4,4a-tetrahydro-2,4-dimethyl-8-acetyl spiro[[1,4]oxazino[4,3-a]quinoline-5(6H), 5'(2'H)-pyrimidine]-2',4',6'(1'H,3'H)-trione

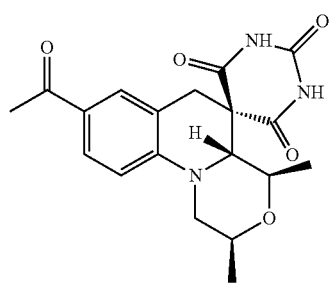

Step 1: 2-(5-bromo-2-fluorophenyl)-1,3-dioxolane

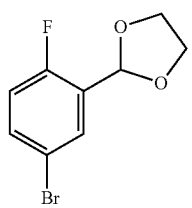 [SMILES: Fc1ccc(Br)cc1C1OCCO1]

5-Bromo-2-fluorobenzaldehyde (14.6 mL, 0.123 mol, Avocado) is combined with 4-methylbenzenesulfonic acid hydrate (2.34 g, 12.0 mmol, Aldrich), ethylene glycol (13.7 mL, 0.25 mol, Mallinkrodt) and toluene (75 mL). The mixture is heated to reflux overnight. The resulting solution is diluted into EtOAc (100 mL) and washed 2× with saturated NaHCO₃, 1× with water and 1× with brine (170 mL ea). The organic layer is dried over Na₂SO₄ and filtered. The solvent is removed by rotary evaporation and the product is purified on a Biotage Flash 75L (800 g silica) cartridge using 96:3:1 heptane:EtOAc:TEA as eluent.

Step 2: 5-Acetyl-2-fluorobenzaldehyde

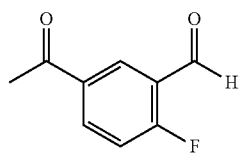

2-(5-bromo-2-fluorophenyl)-1,3-dioxolane (5.2 g, 21.2 mmol) is taken up in dry, preservative-free THF (30 mL) and the solution is cooled to −40° C. under N₂. A 1.6 M solution of n-butyllithium in hexanes (13.2 mL, 1 eq) is added via syringe and the solution is stirred for 25 minutes @−40° C. The lithiated substrate is added dropwise via cannula to a −40° C. solution of N-methoxy-N-methylacetamide (2.36 mL, 22.2 mmol, Aldrich) in 10 mL of dry, preservative-free THF. The solution is warmed to RT with stirring for 1 hour. The solution is poured into a flask containing 1.0M HCl (100 mL) and heated to 65° C. with vigorous stirring overnight. Upon cooling the oily product is extracted into EtOAc (200 mL) and the organic layer is washed with water and brine (200 mL each). The organic layer is dried over Na₂SO₄ and filtered. The solvent is removed by rotary evaporation and the product is purified on a Biotage Flash 75L (800 g silica) cartridge using 30% MTBE in heptane as eluent. The product containing fractions are pooled and the solvent is removed by rotary evaporation. The product is dried under vacuum yielding an oily yellow solid.

Step 3

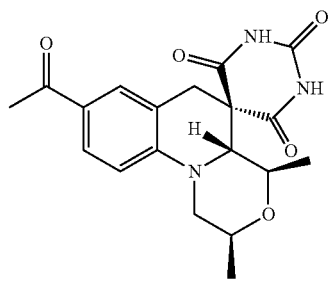

The aldehyde from step 2 is combined with cis-2,6-dimethylmorpholine (1.18 mL, 9.75 mmol, TCI-US), K₂CO₃ (2.15 g, 2.5 eq, Mallinkrodt) and CH₃CN (12 mL) in a flask and the heterogonous mixture is heated to 80° C. overnight with vigorous stirring. After filtration the solvent is removed by rotary evaporation. The orange oil is taken up in EtOAc (200 mL) and washed 2× with water and 1× with brine (175 mL each). The organic layer is dried over Na₂SO₄ and filtered. The solvent is removed by rotary evaporation and the product is purified on a Biotage Flash 75L (800 g silica) cartridge using 30% MTBE in heptane as eluent. The product containing fractions are pooled and the solvent is removed by rotary evaporation yielding 5-acetyl-2-cis-(2,6-dimethylmorpholin-4-yl)benzaldehyde as an orange-yellow oil. The aldehyde is taken up in CH₃OH (10 mL) and combined with barbituric acid (719 mg, 5.61 mmol, Aldrich) in a sealed vial. The reaction is heated to 80° C. on a shaker block for 3.5 hours. The vial is cooled in the freezer to precipitate out a mustard yellow solid. The solid is filtered and washed with CH₃OH. The solid was used as is for chiral resolution. $^1$H NMR (400 MHz, DMSO-d₆) δ ppm 0.91, 1.14, 2.38, 2.88, 3.42, 3.51, 3.59, 3.81, 4.20, 6.91, 7.50, 7.69, 11.47, 11.79.

Example 61

Additional compounds of the invention may be produced via the methodology described herein as well as methods known in the art. Examples of additional compounds of the invention include, but are not limited to, those compounds shown below.

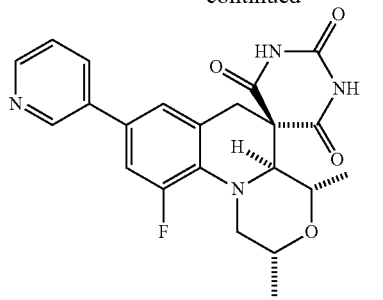

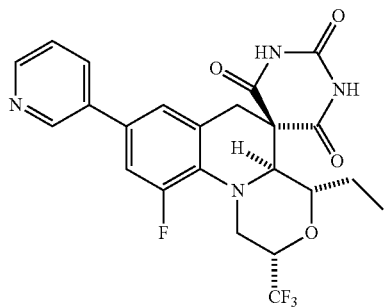

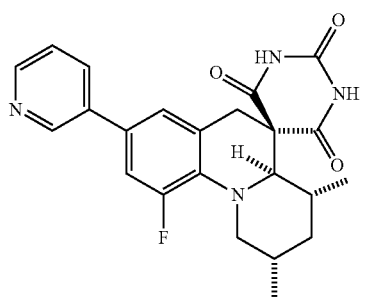

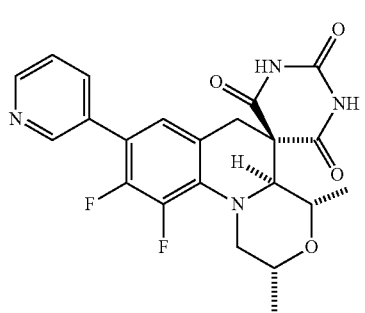

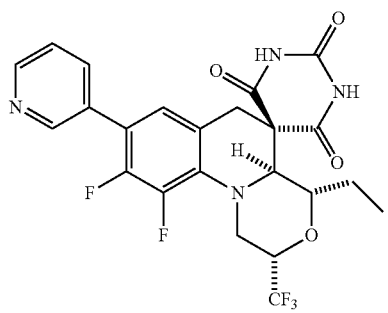

87
-continued
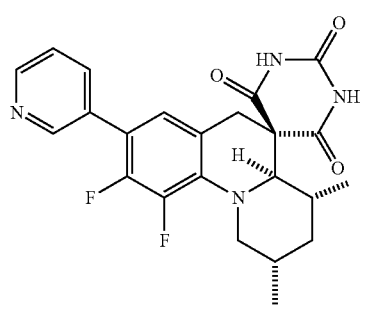
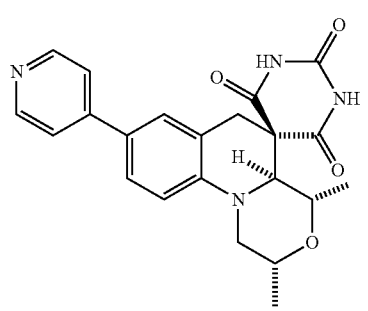
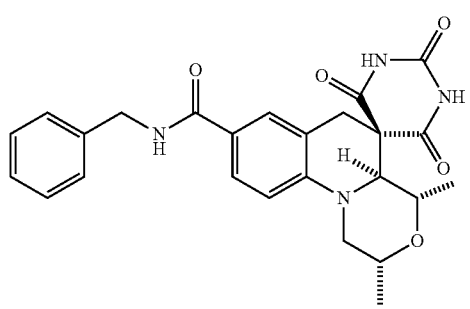
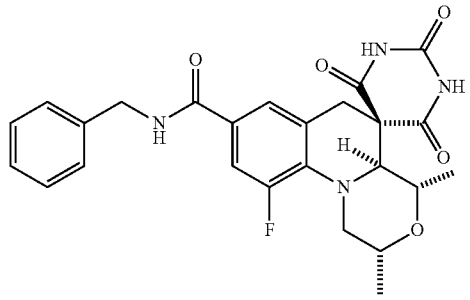
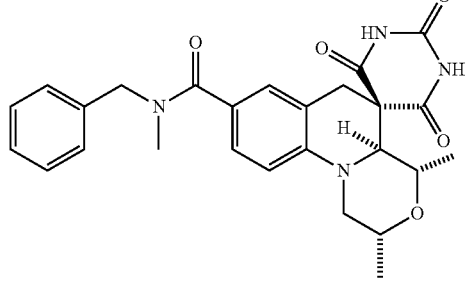
88
-continued
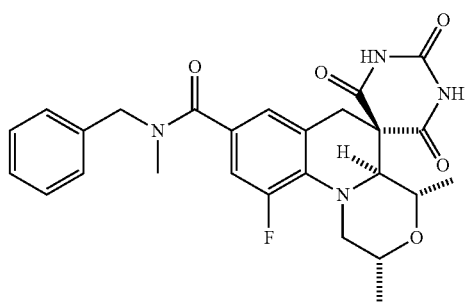
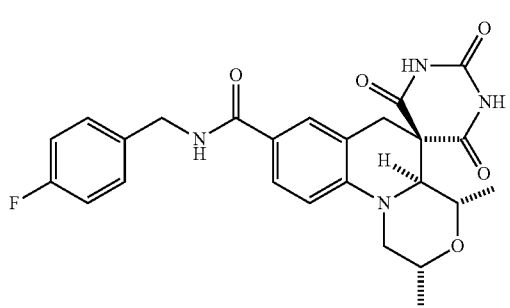
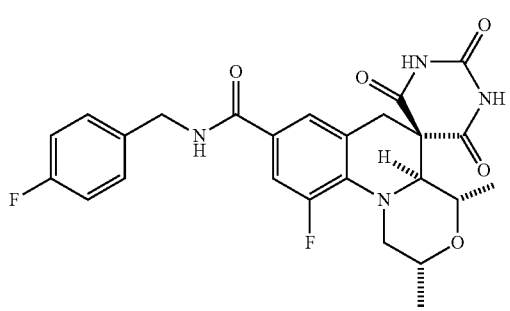
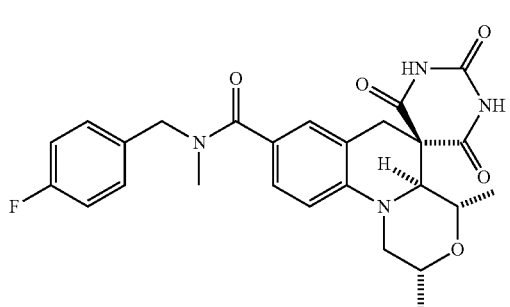
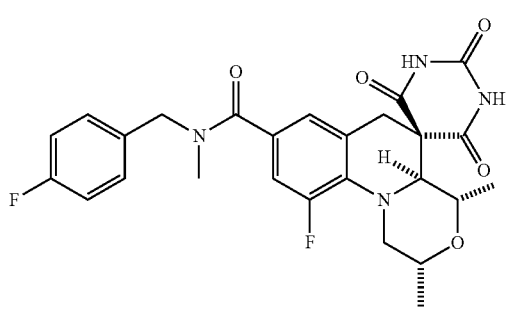

89
-continued
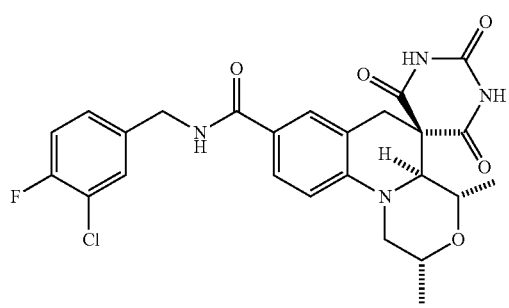
90
-continued
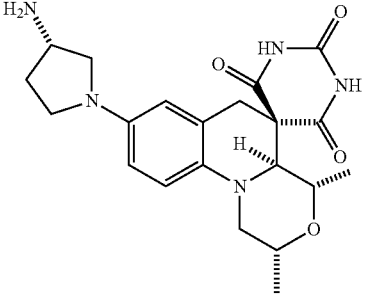
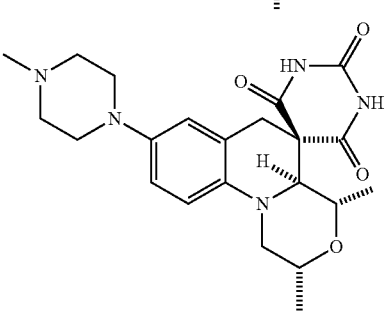
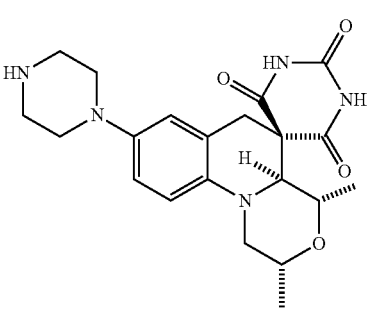
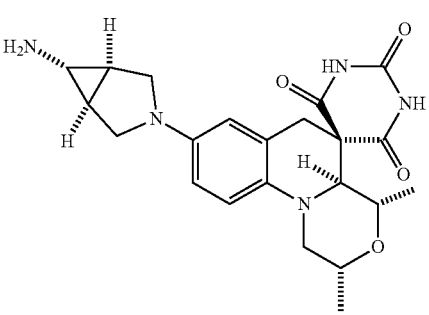
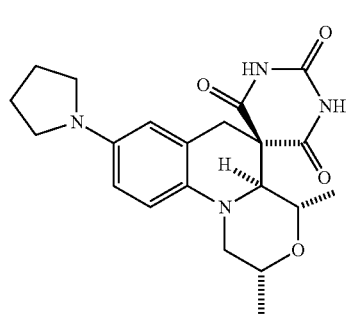
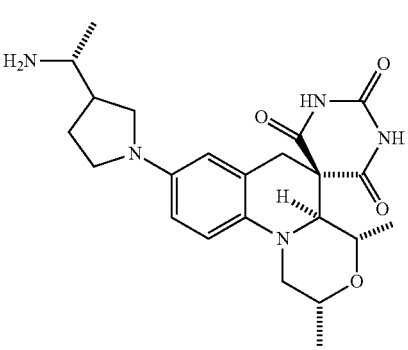

91
-continued
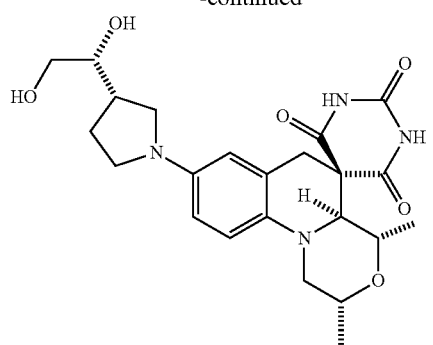
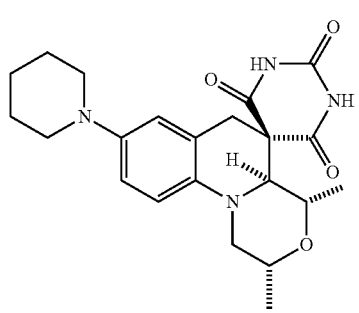
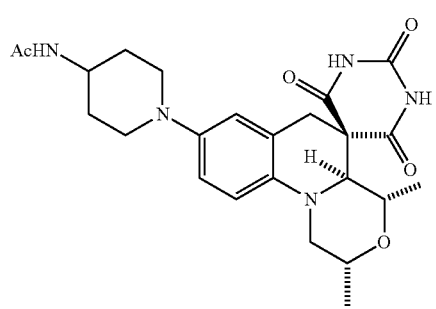
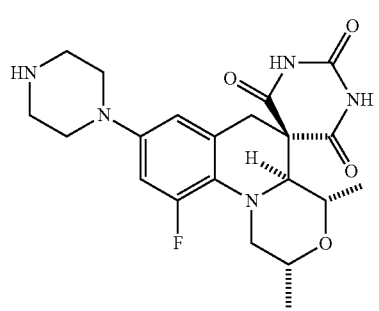
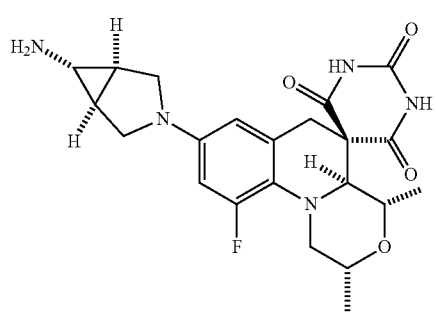
92
-continued
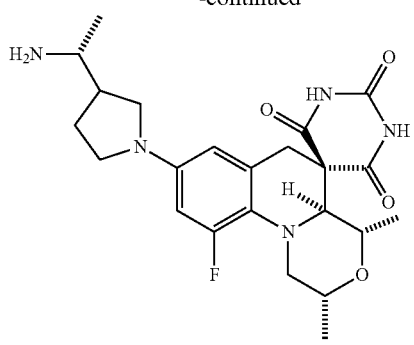
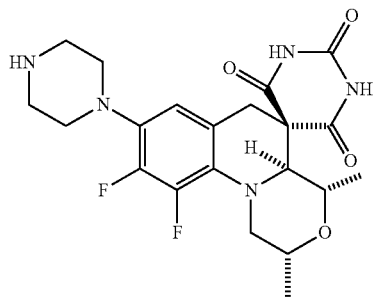
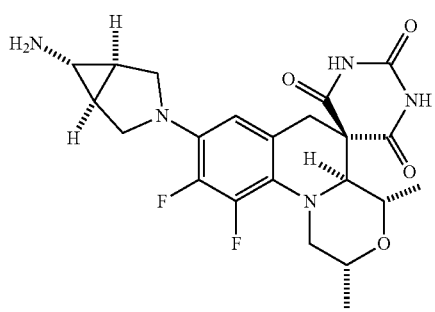
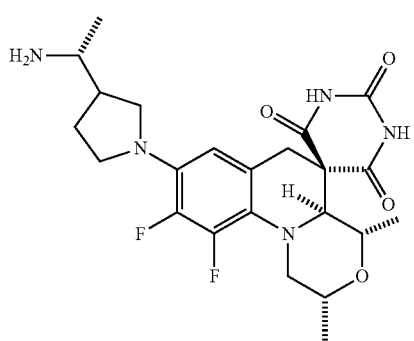
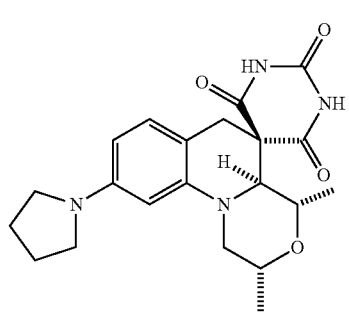

93
-continued
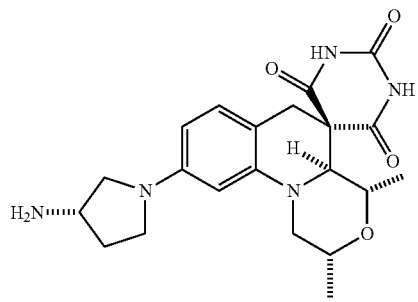
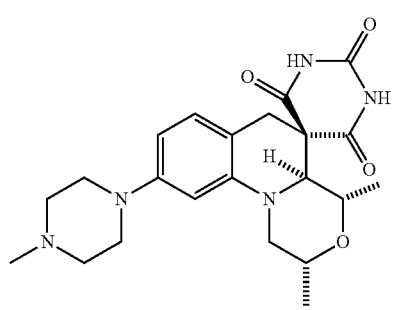
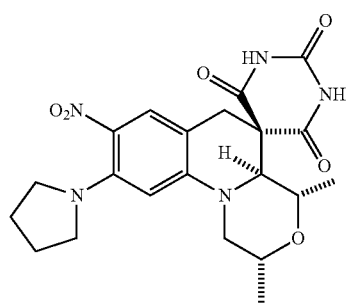
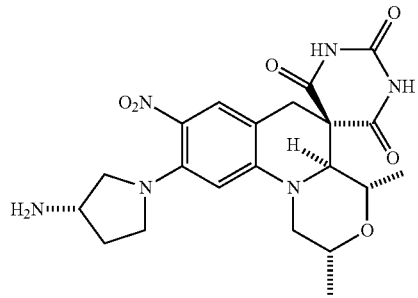
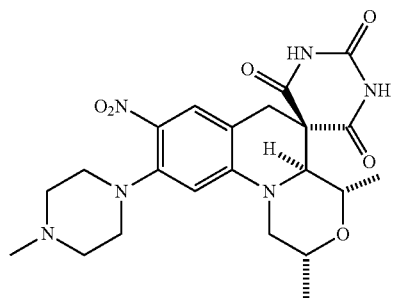
94
-continued
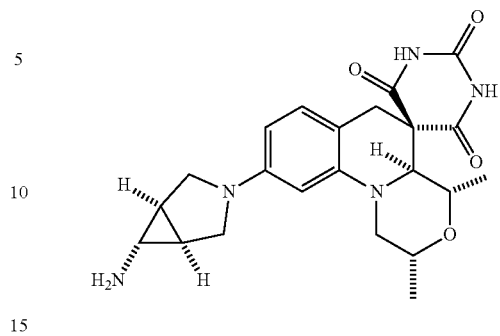
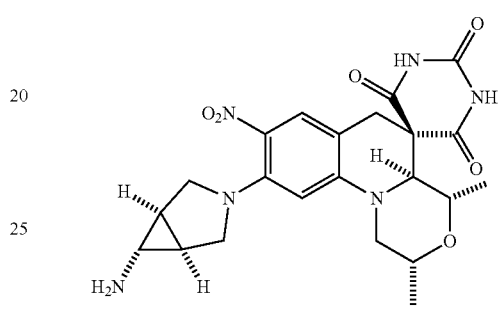
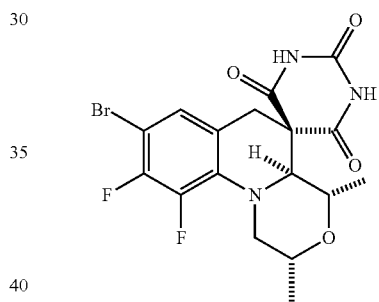
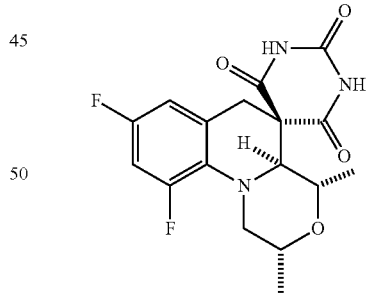
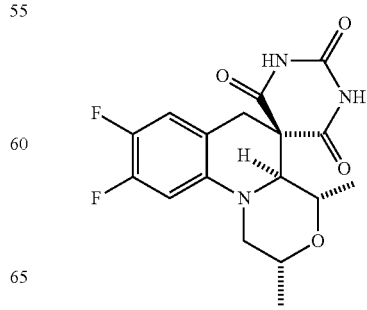

95
-continued
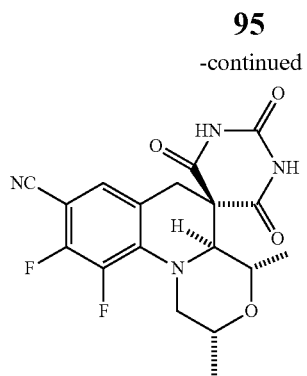
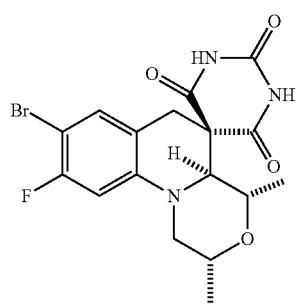
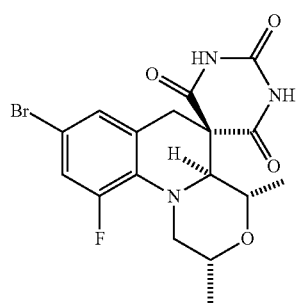
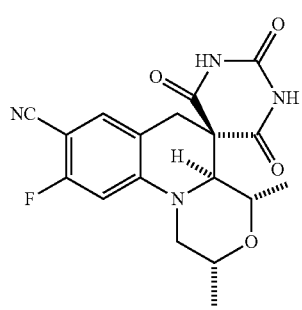
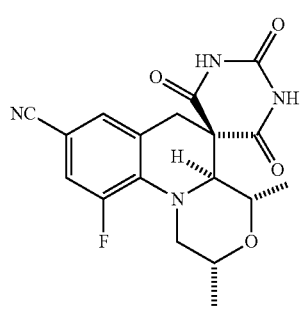
96
-continued
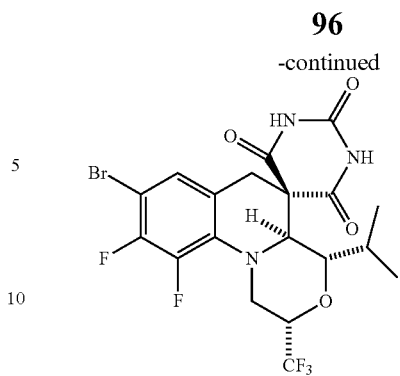
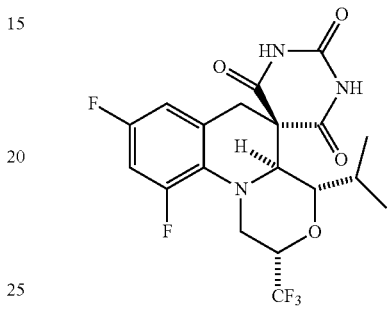
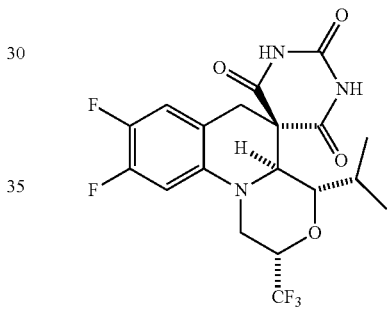
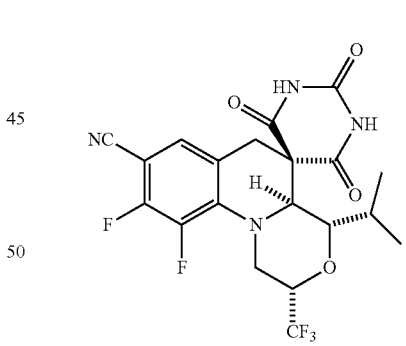
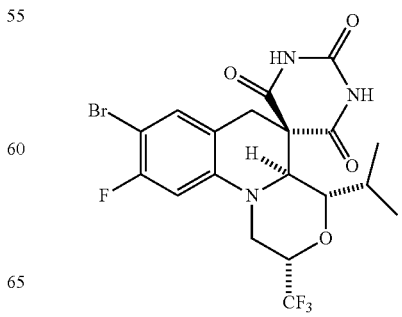

-continued
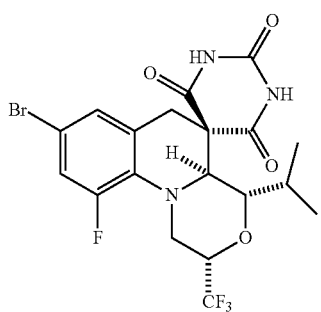
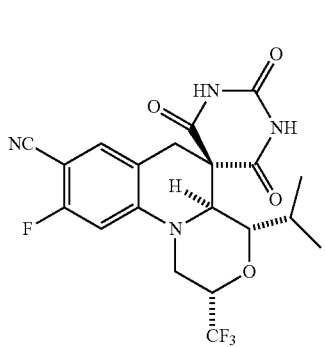
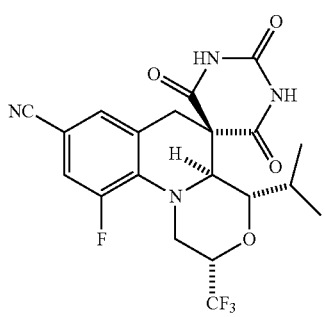
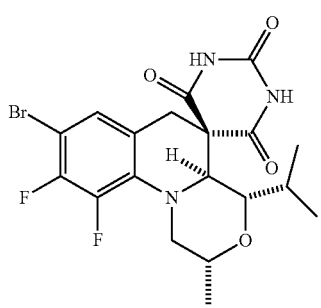
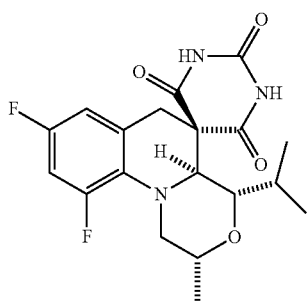
-continued
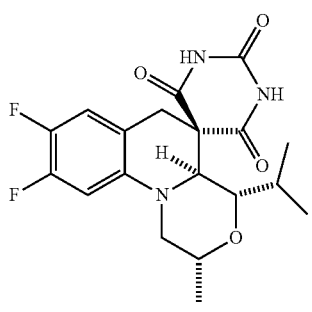
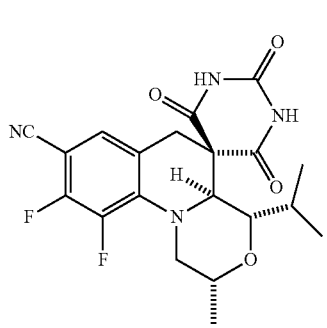
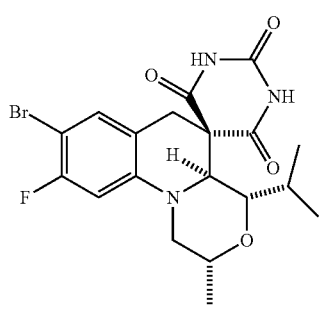
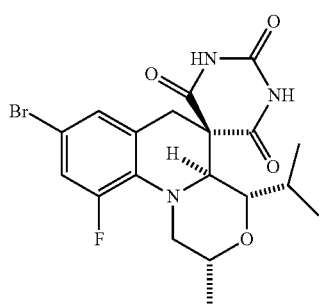
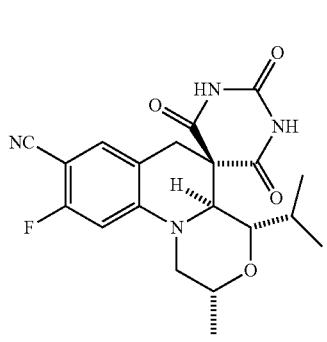

99
-continued
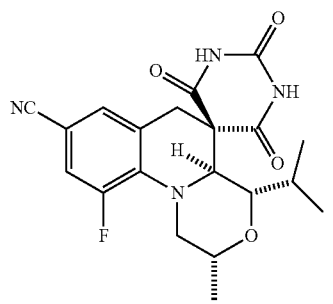
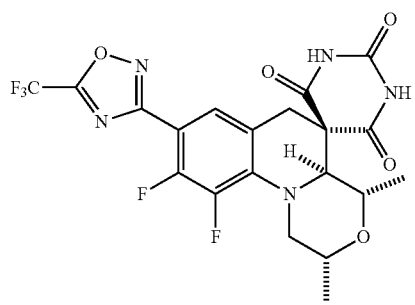
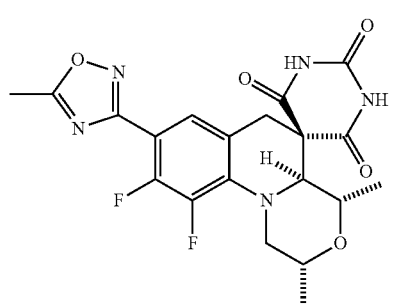
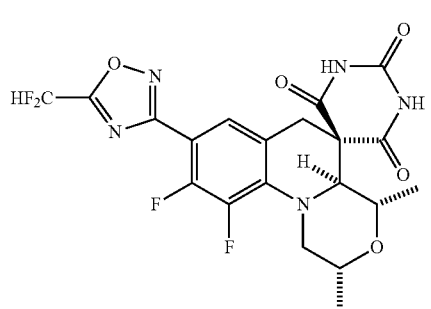
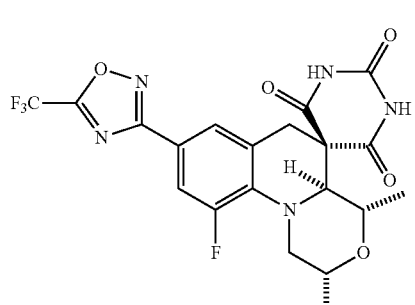
100
-continued
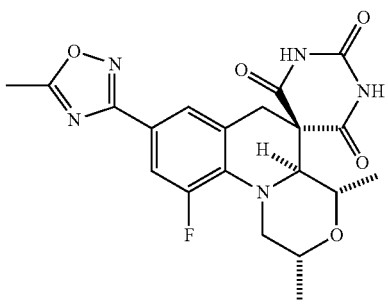
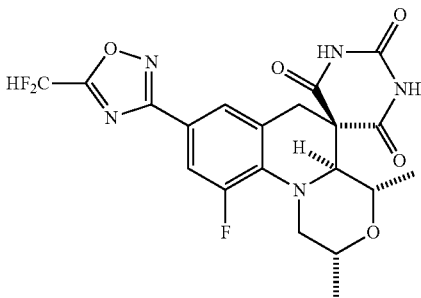
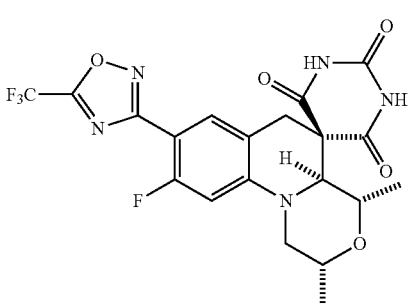
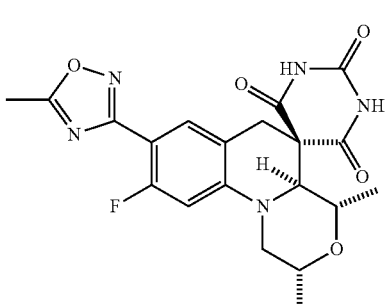
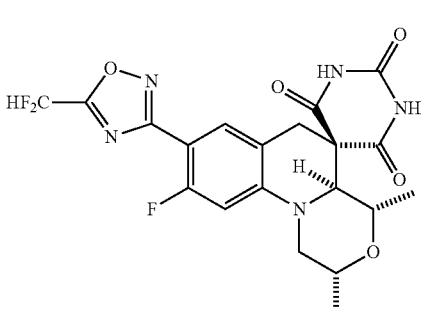

| 101 | 102 |
|---|---|
| -continued | -continued |
| 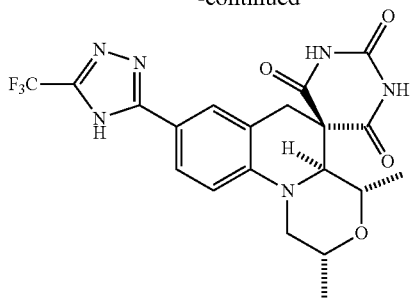 | 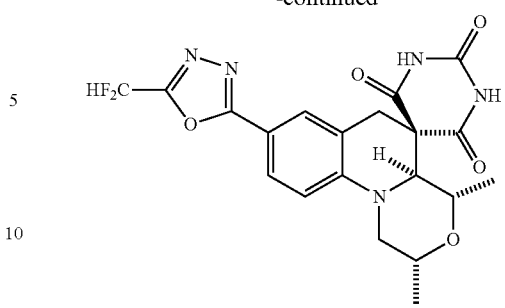 |
| 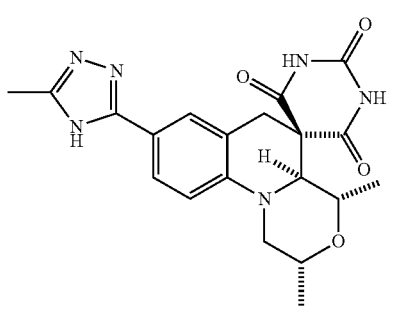 | 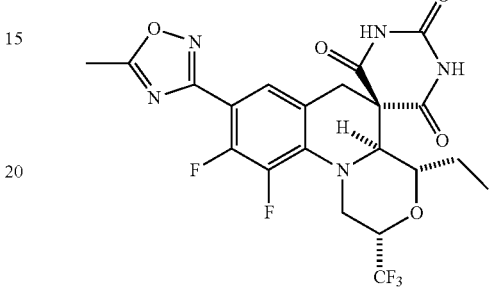 |
| 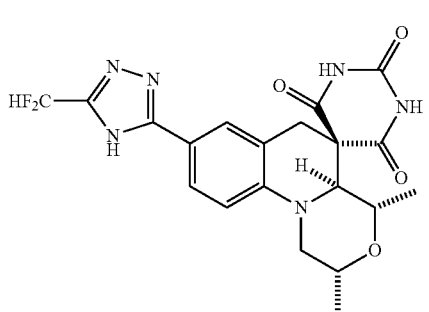 | 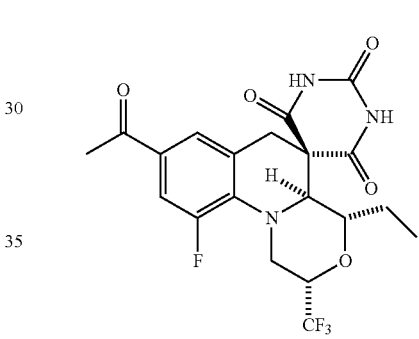 |
| 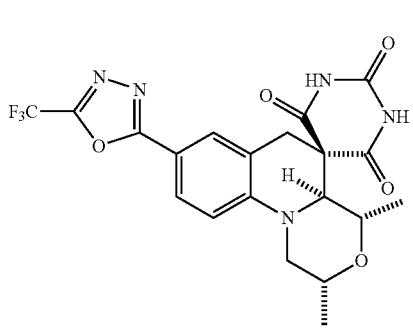 | 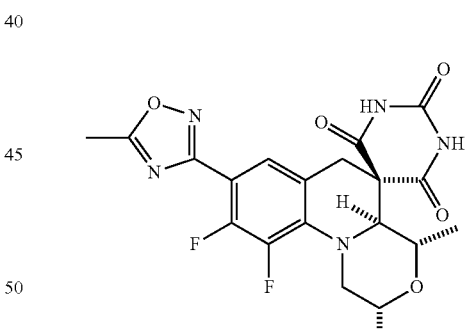 |
| 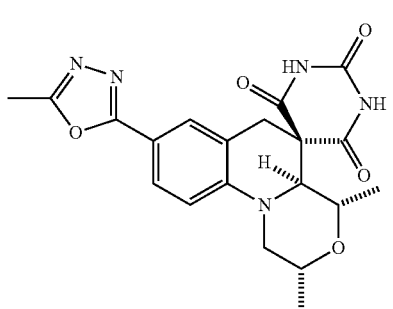 | 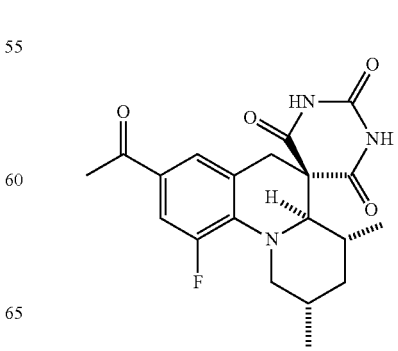 |

103
-continued
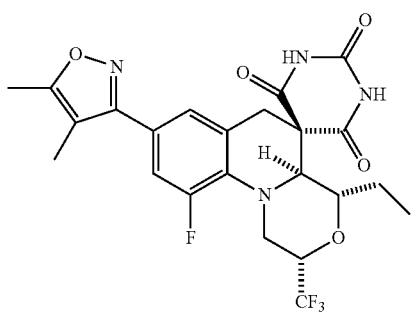
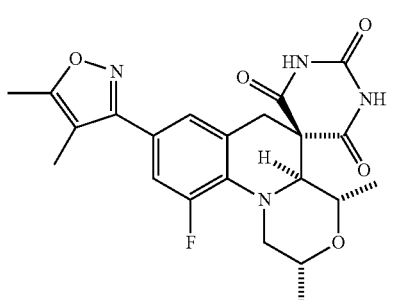
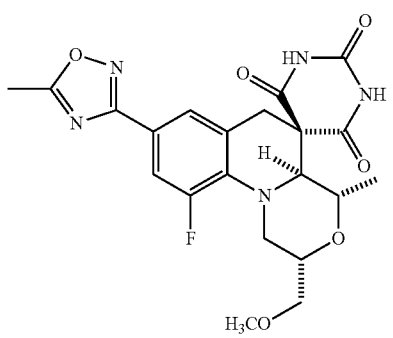
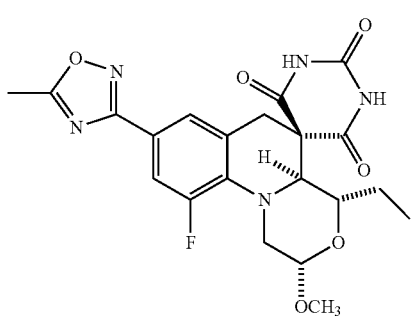
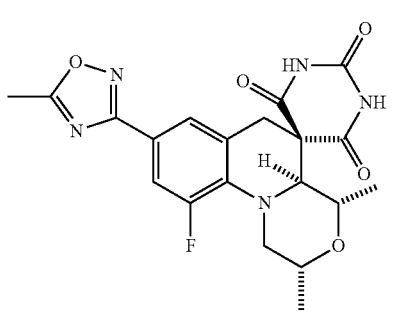
104
-continued
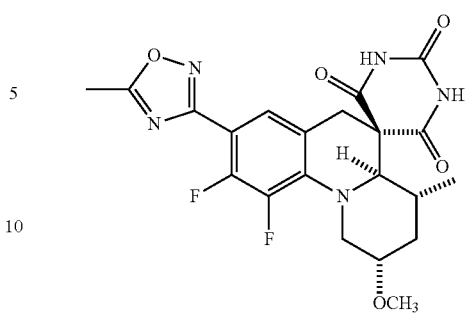
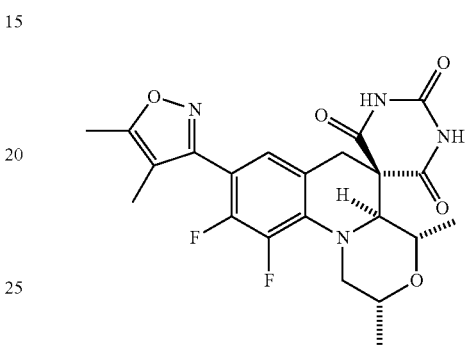
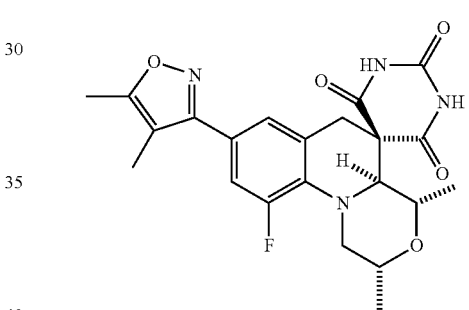
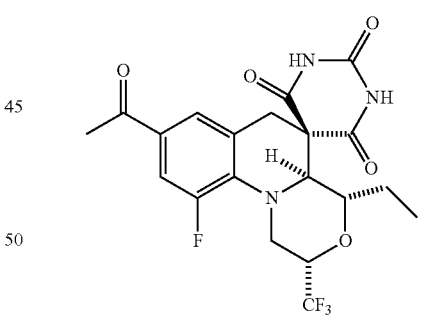
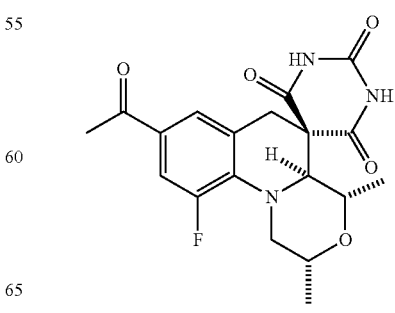

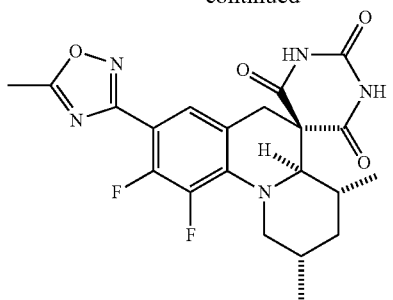
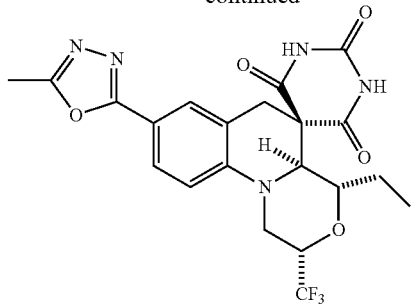
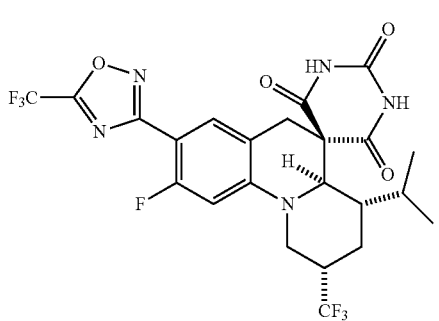
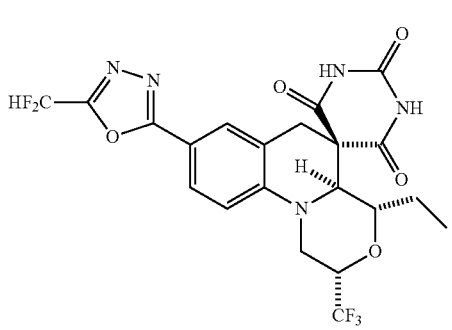
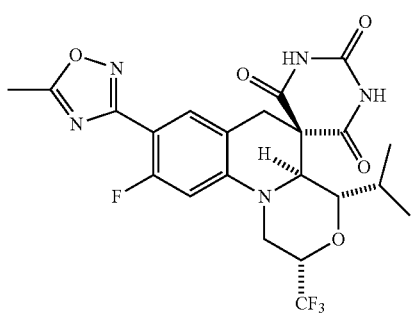
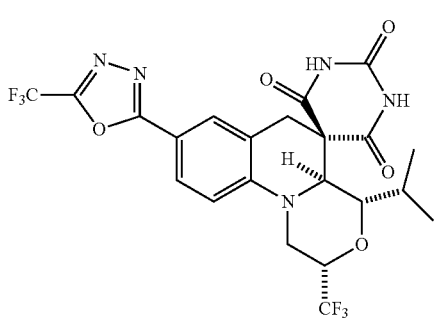
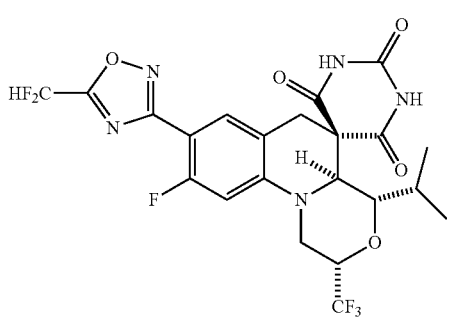
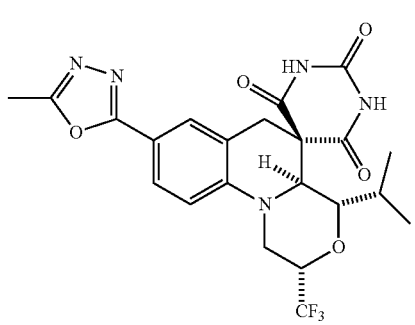
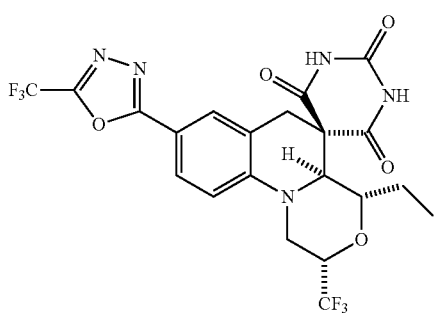
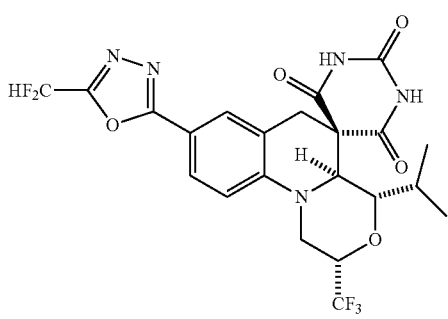

107
-continued
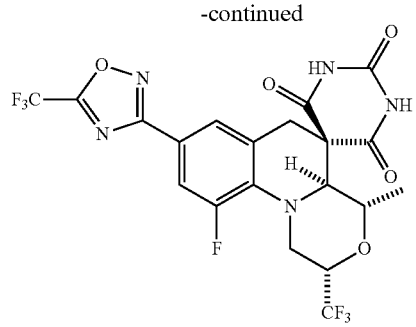
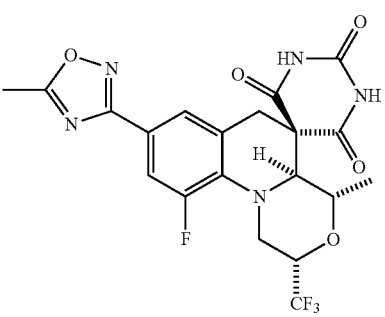
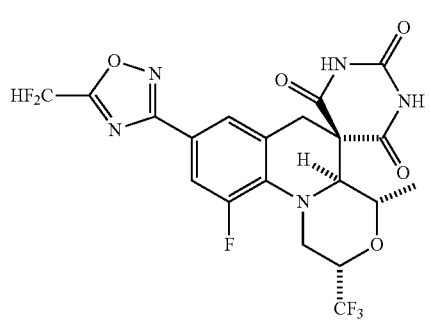
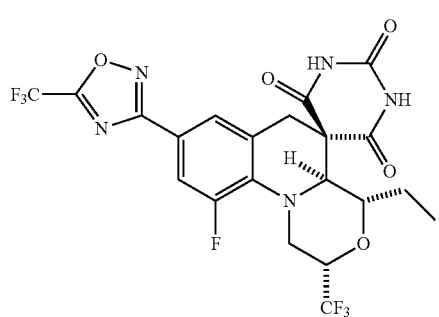
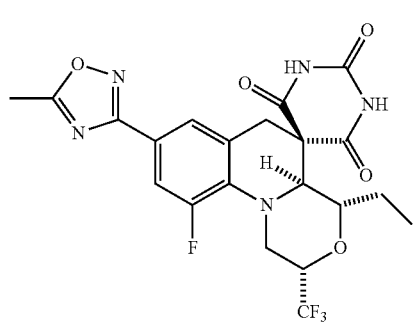
108
-continued
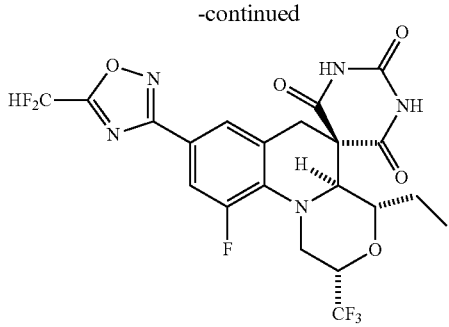
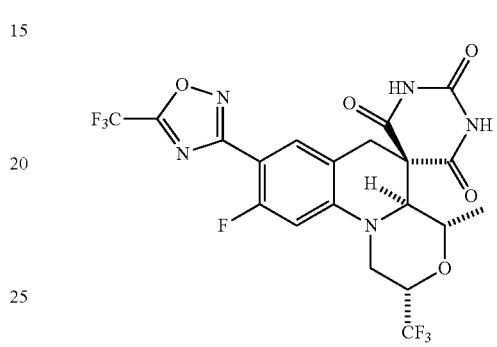
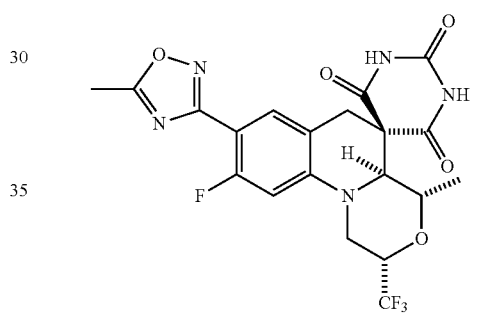
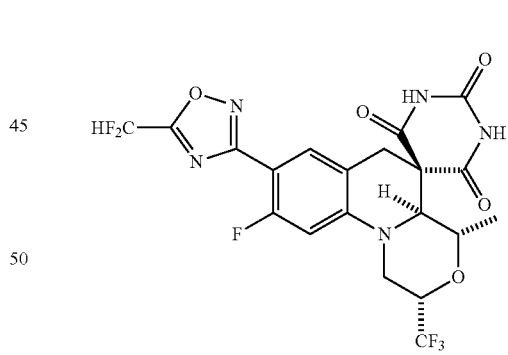
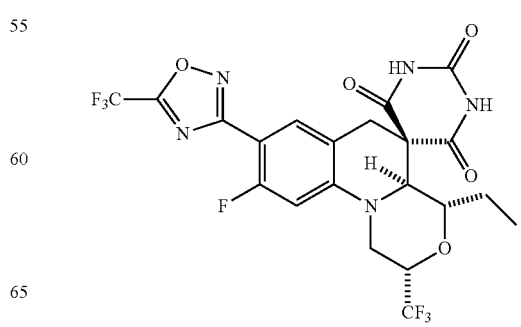

109
-continued
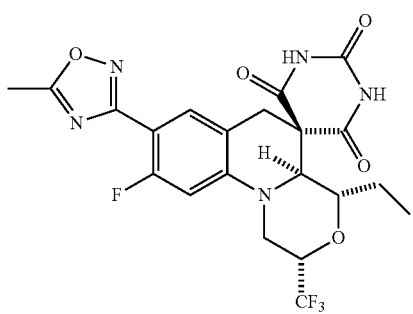
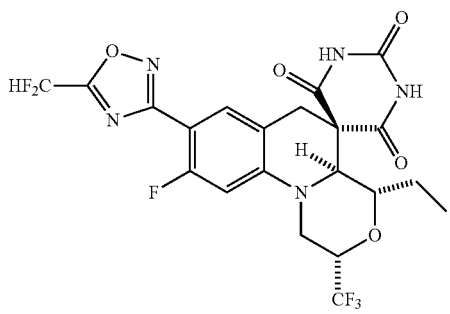
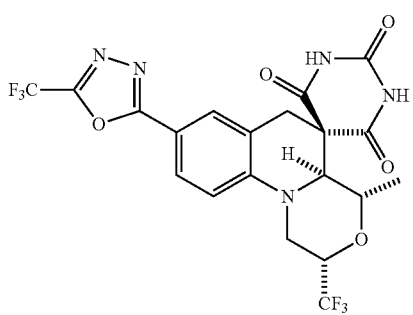
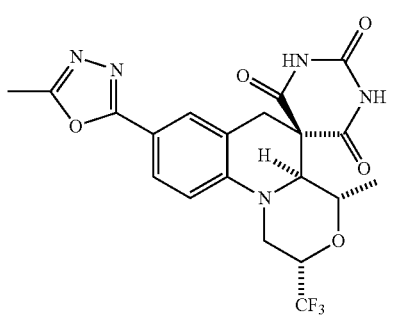
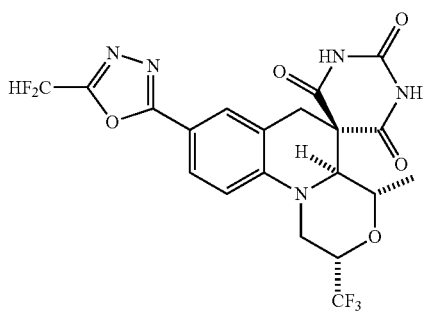
110
-continued
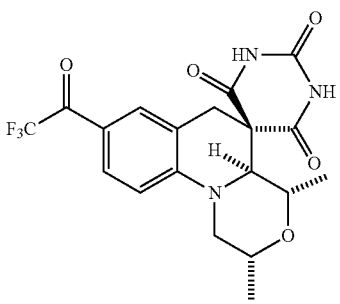
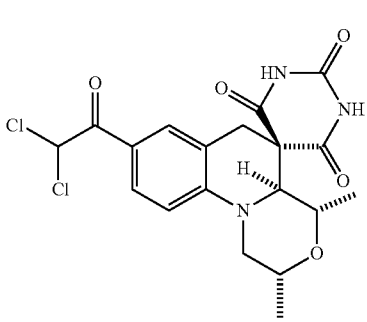
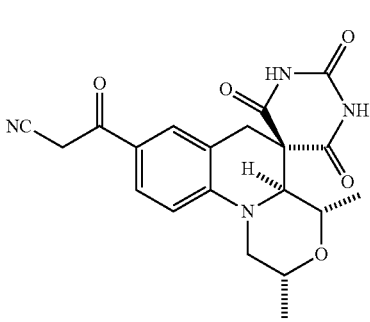
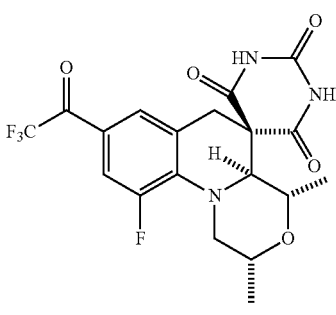
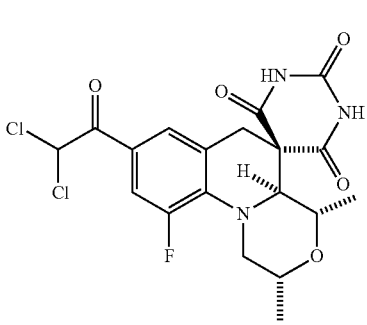

111
-continued
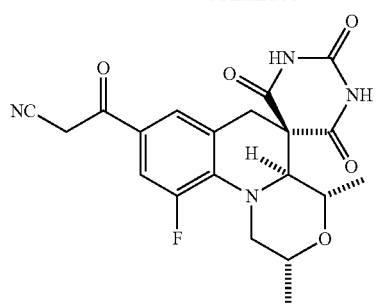
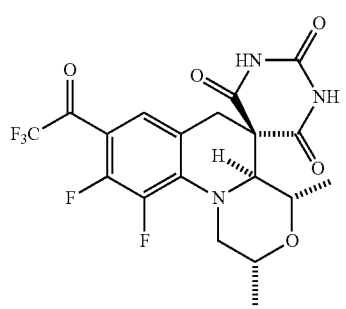
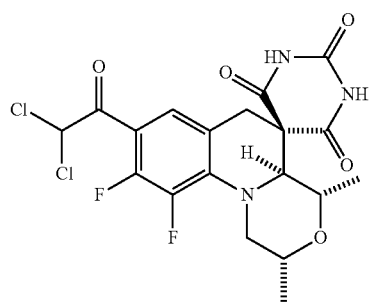
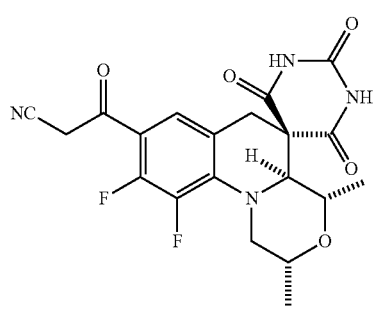
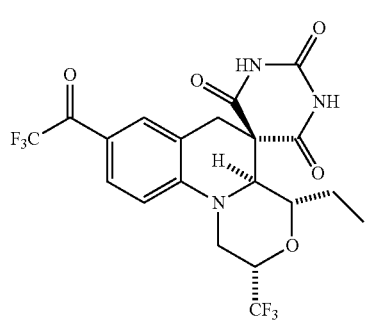
112
-continued
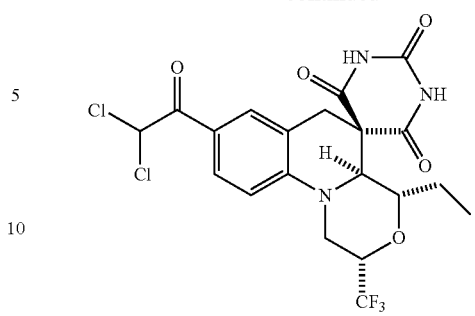
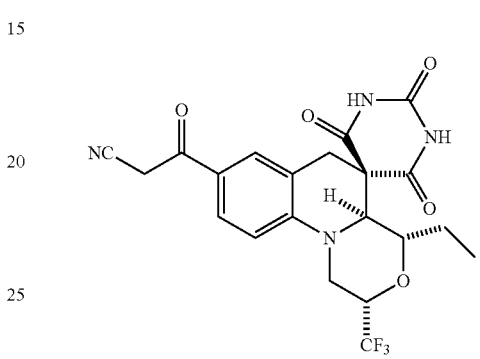
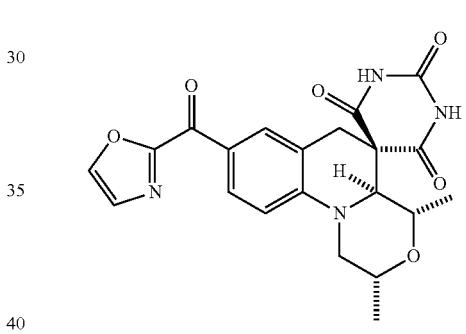
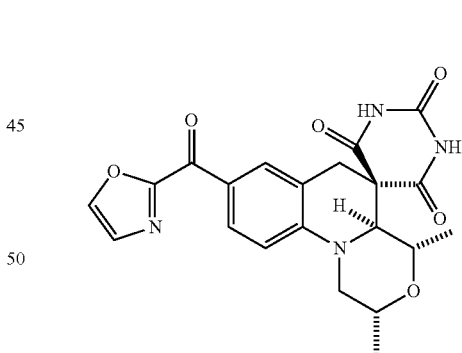
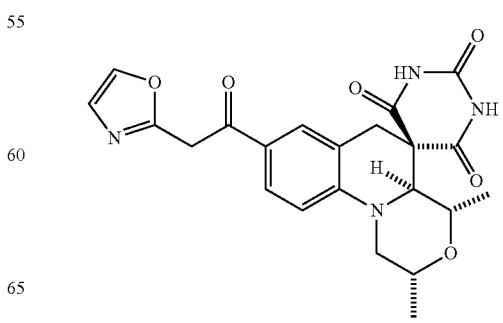

113
-continued
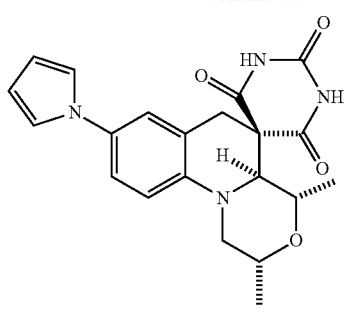
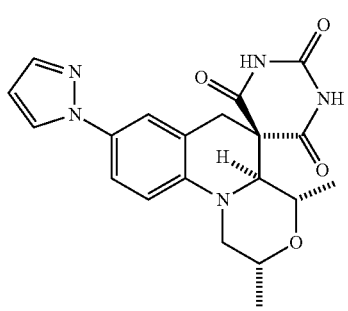
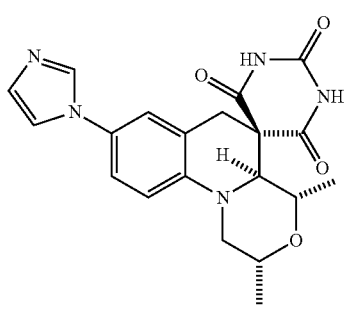
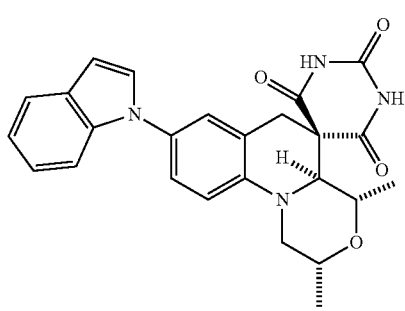
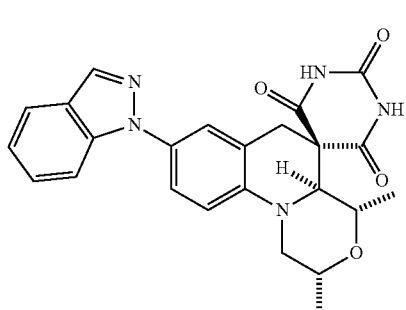
114
-continued
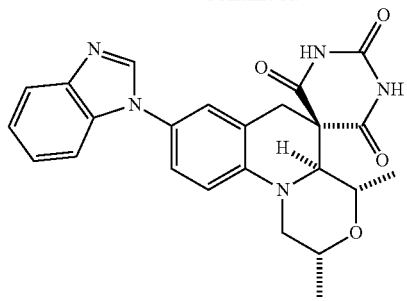
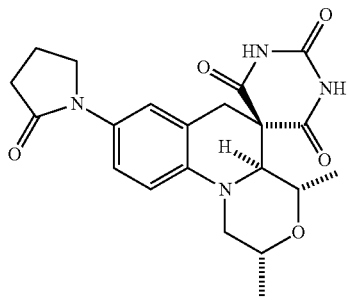
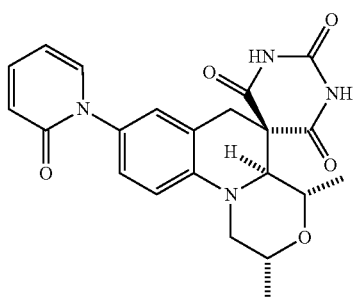
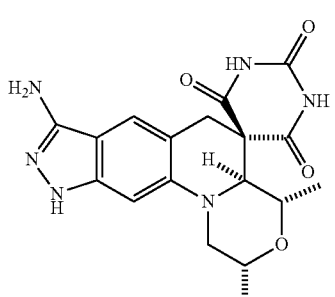
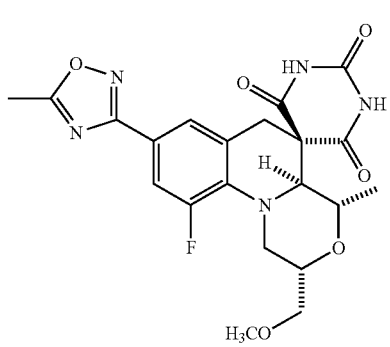

115
-continued
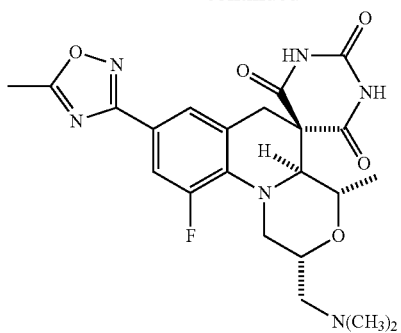
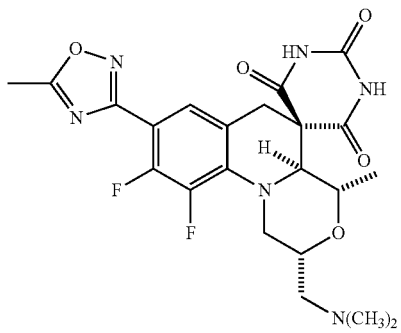
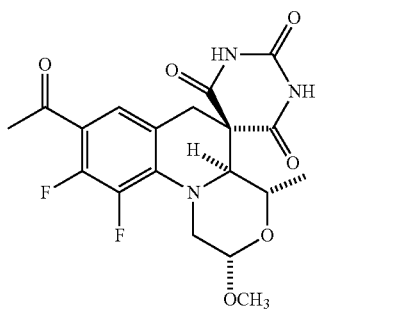
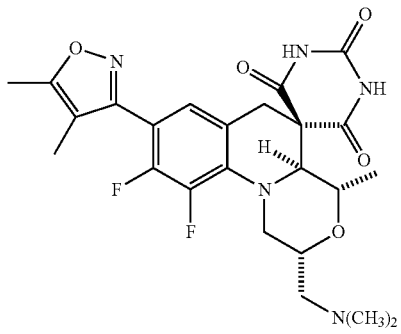
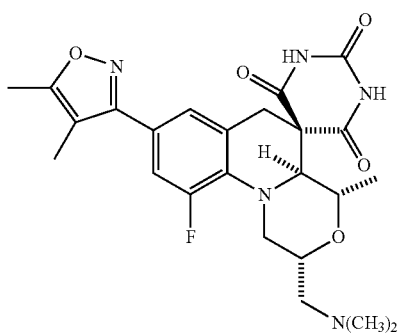
116
-continued
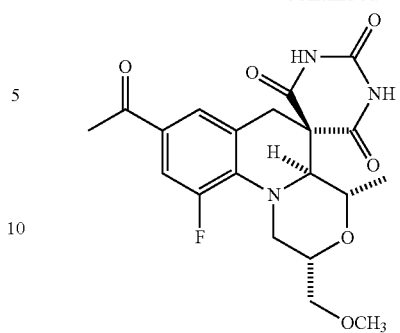
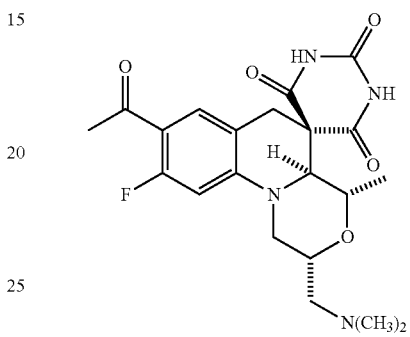
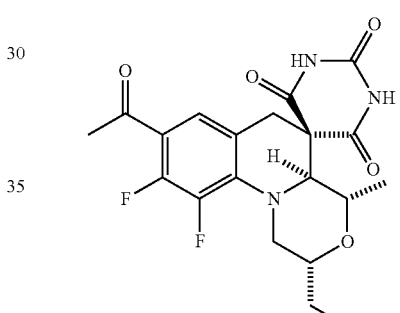
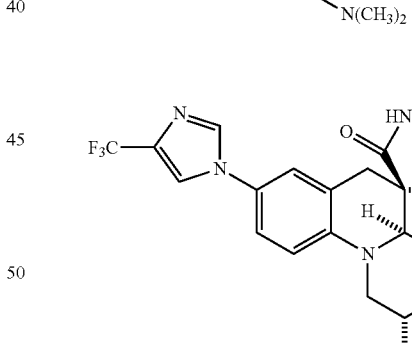
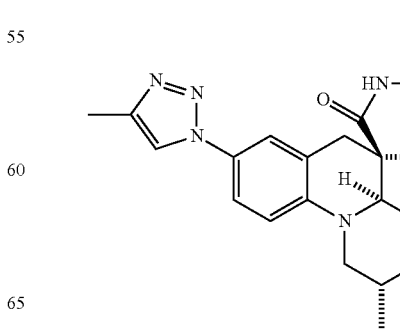

117
-continued
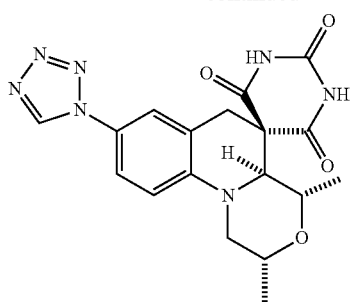
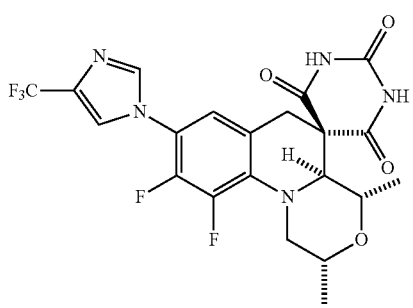
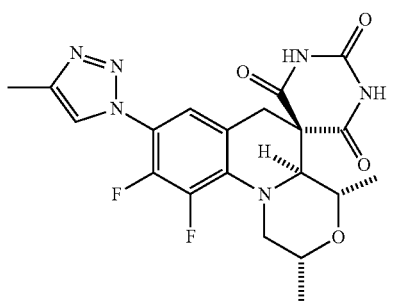
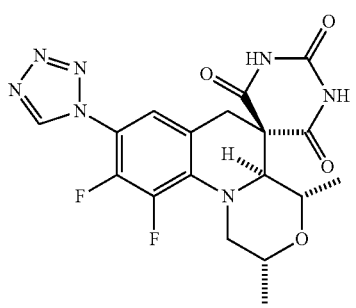
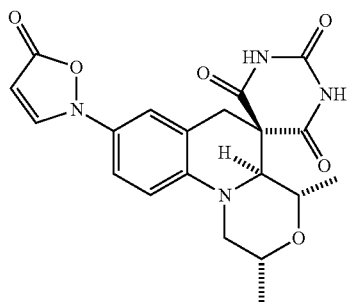
118
-continued
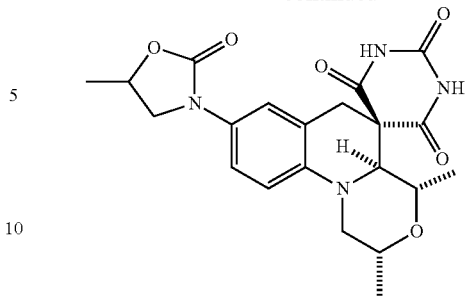
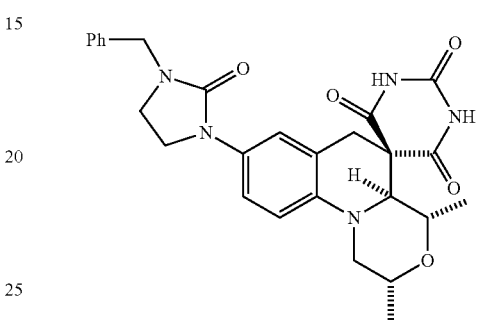
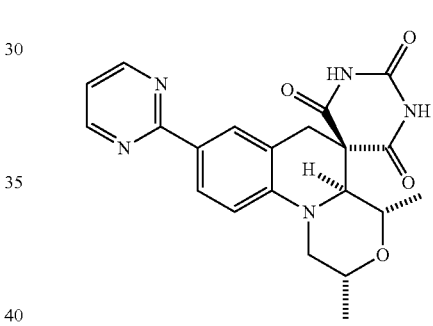
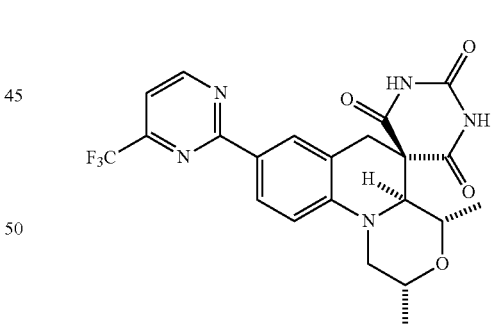
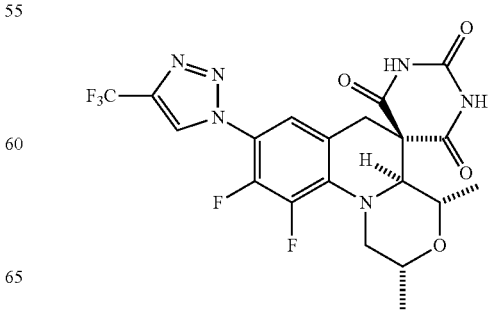

119
-continued
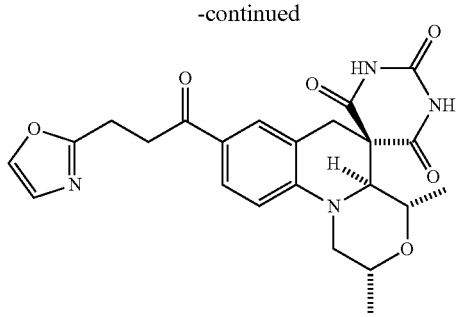
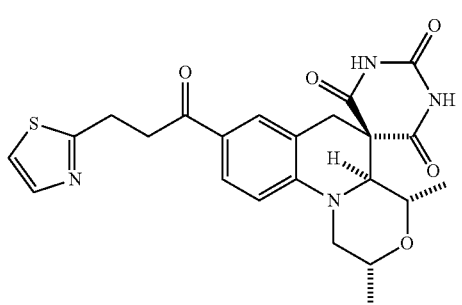
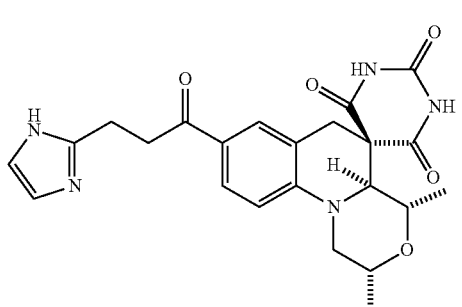
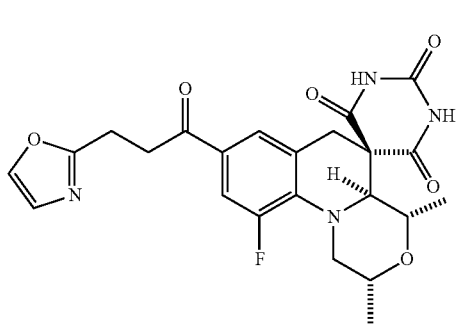
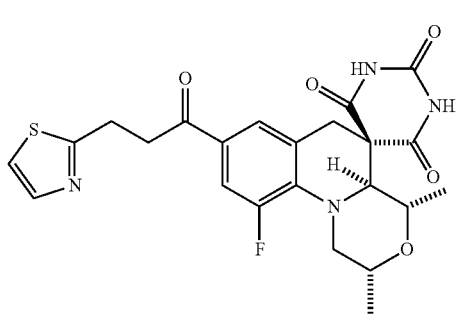
120
-continued
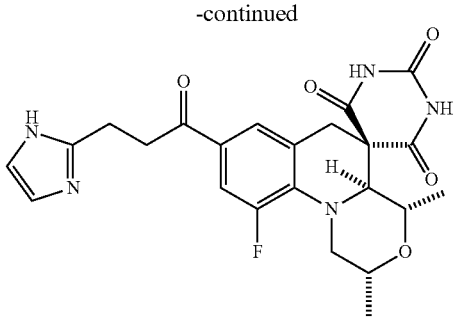
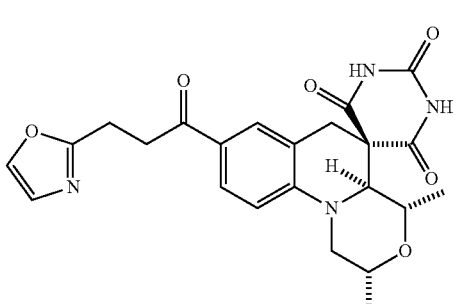
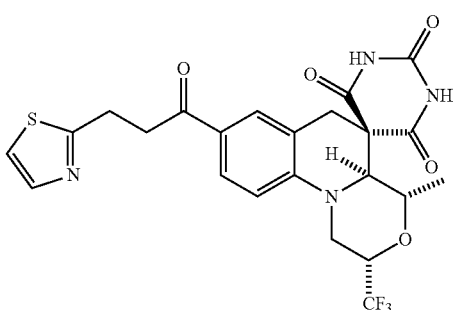
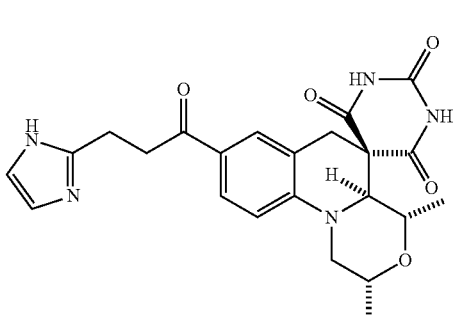
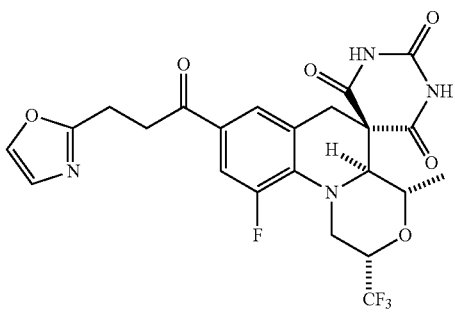

121
-continued
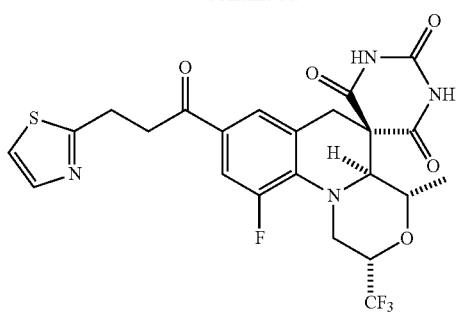
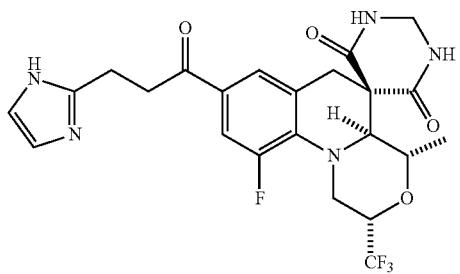
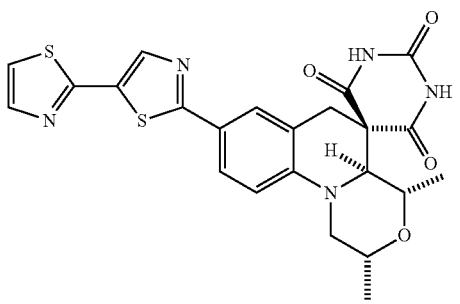
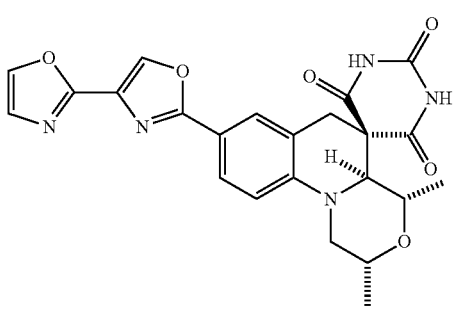
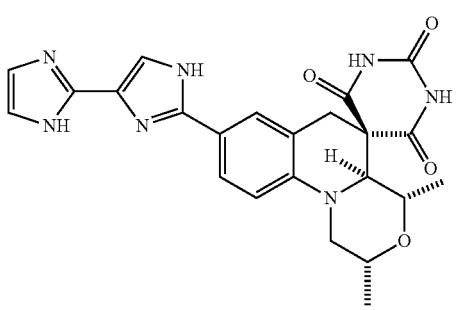
122
-continued
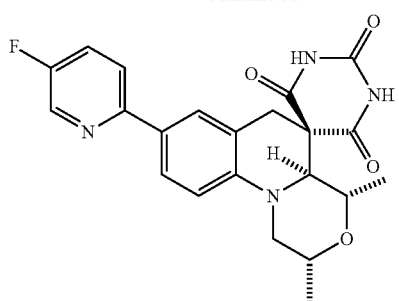
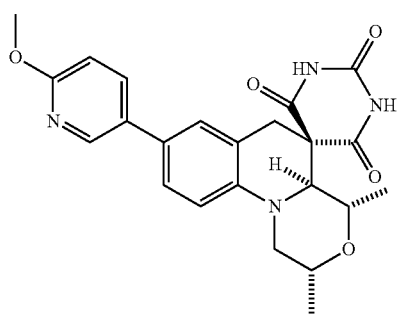
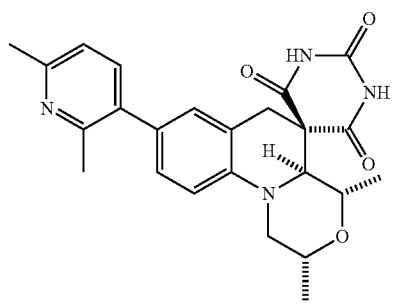
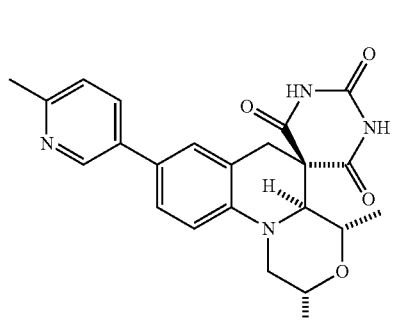
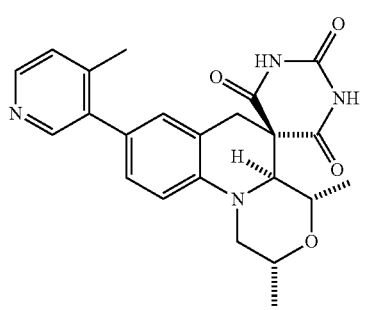

123
-continued
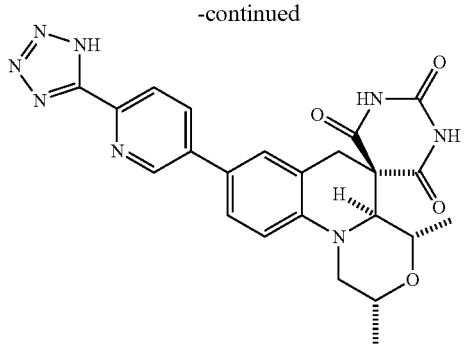
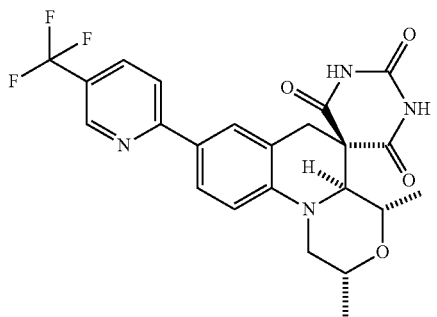
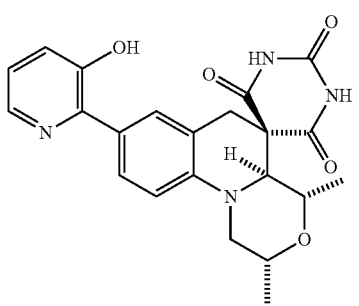
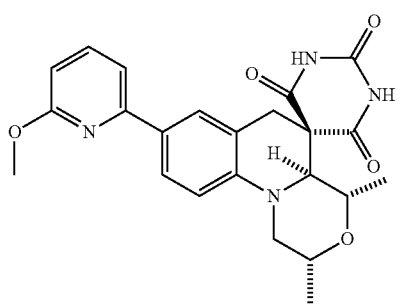
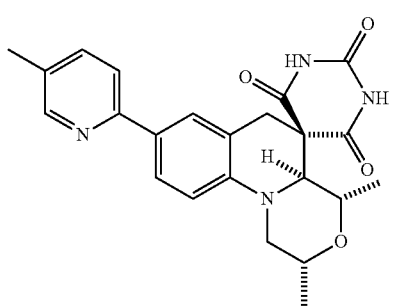
124
-continued
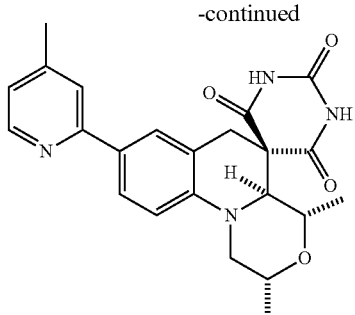
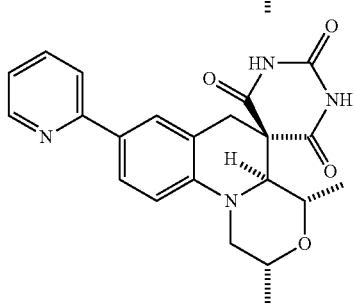
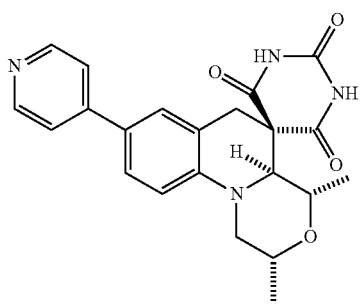
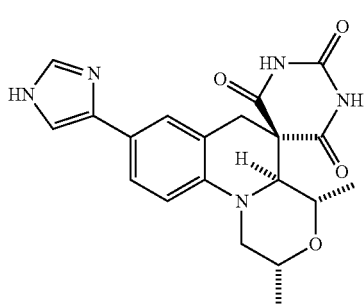
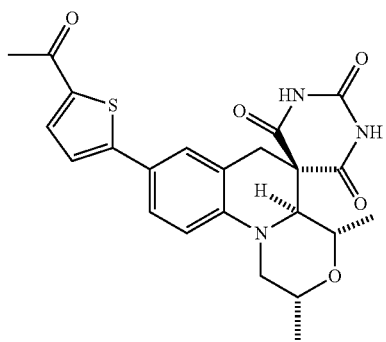

125
-continued
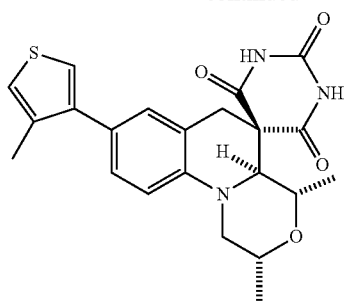
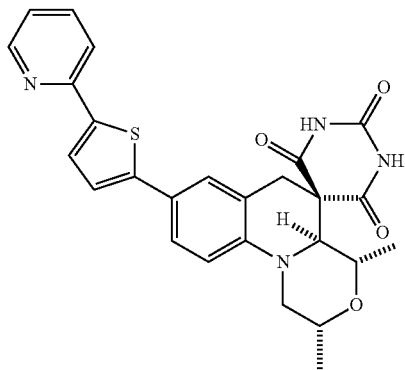
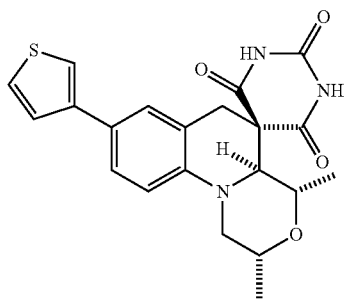
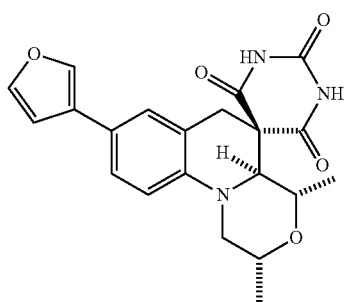
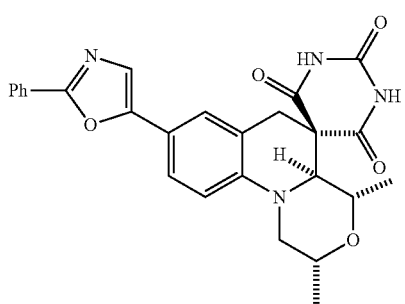
126
-continued
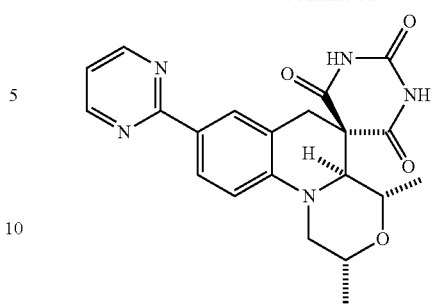
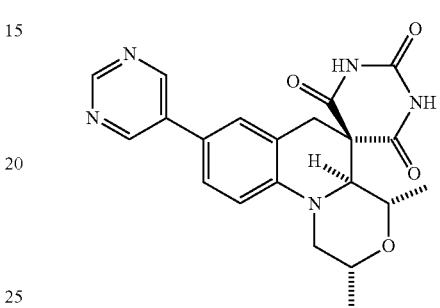
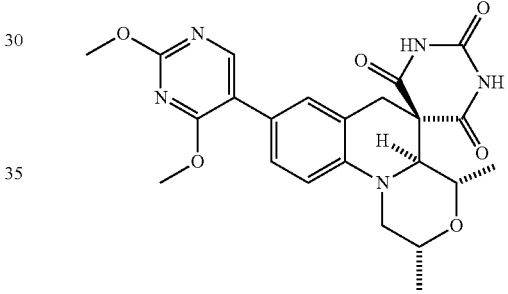
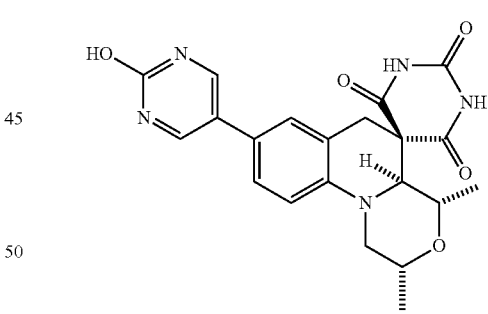
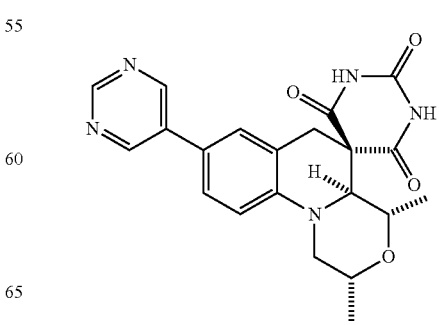

-continued

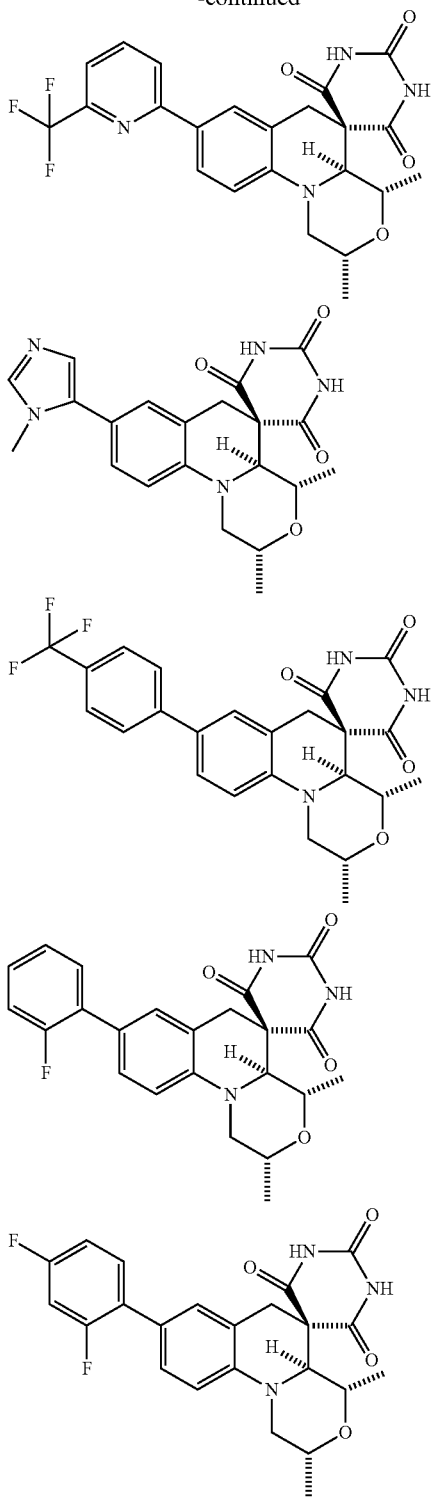

In Vitro DNA Gyrase Assay

DNA gyrase is a bacterial topoisomerase that introduces negative supercoils into DNA. The DNA gyrase assay measures the degree of enzymatic activity by quantitating relative amounts of relaxed vs. supercoiled DNA on an EtBr-stained 0.8% agarose gel. The substrate is relaxed pBR322. The enzyme is *E. coli* DNA gyrase which is purified from strains overexpressing each of the subunits individually (there are two: A and B and the holoenzyme consists of the heterodimer $A_2B_2$). See for example, Hallett et al. Cloning of the DNA gyrase genes under tac promoter control: overproduction of the gyrase A and B proteins. *Gene* 93: 139-142 (1990); Simon et al. Biochemical complementation studies in vitro of gyrase subunits from different species. *FEBS Lett* 373:88-92 (1995); and O'Dea et al. Mutations in the B subunit of *Escherichia coli* DNA gyrase that affect ATP-dependent reactions. *J. Biol Chem* 1996 271:9723-9 (1996).

In the below chart, racemic mixtures are denoted with (±)- and enantiomerically enriched samples are denoted by (−)- or (+)-.

| Prepared per Example No. | Structure | Gyrase IC50 (μM) |
|---|---|---|
| 1 | (±)- | 11.79 |
| 1 | (±)- | 18.96 |
| 1 | (−)-enantiomer | 6.1 |
| 2 | (±)- | 45.59 |

-continued
| Prepared per Example No. | Structure | Gyrase IC50 (μM) |
|---|---|---|
| 3 | 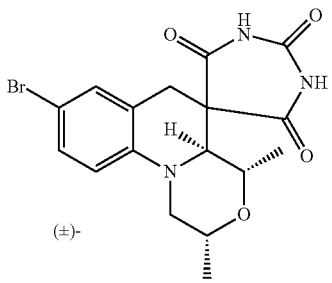 (±)- | 23.96 |
| 3 | 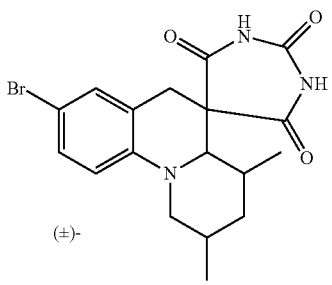 (±)- mixture of cis- and trans- isomers | 46.65 |
| 4 | 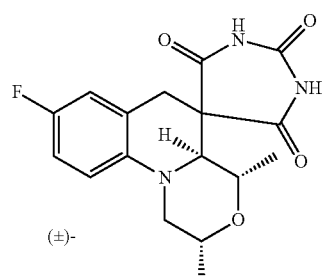 (±)- | 70.2 |
| 6 | 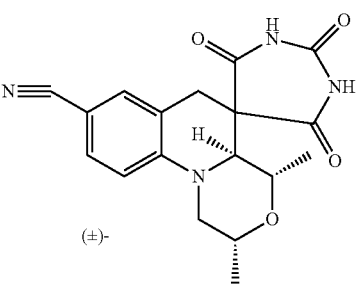 (±)- | 13.75 |
| 18 | 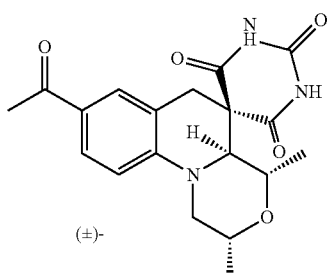 (±)- | 8.4 |
-continued
| Prepared per Example No. | Structure | Gyrase IC50 (μM) |
|---|---|---|
| 25 | 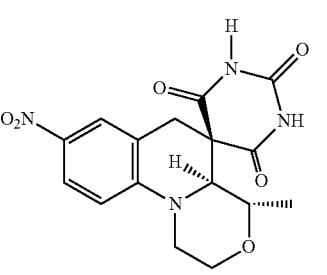 (-) enantiomer | 18.2 |
| 25 | 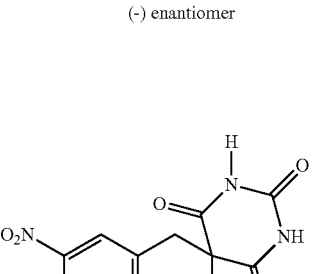 (±)- | 32 |
| 25 | 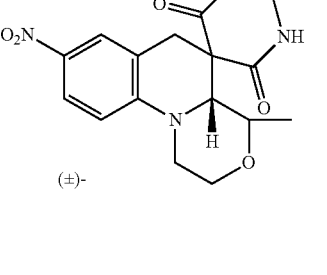 (±)- mixutre | |
| 43 | 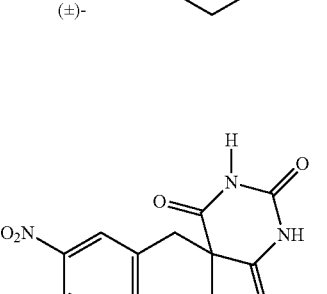 (±)- | 24 |

What is claimed is:

1. A compound of formula I, or a pharmaceutically acceptable salt thereof;

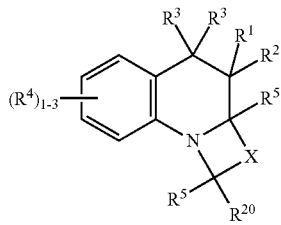

I wherein, $R^1$ is
(a) $R^{12}$
(b) C(=O)$R^6$, or
(c) CN;

$R^2$ is
(a) $R^{12}$
(b) C(=O)$R^7$,
(c) CN,
(d) —CH$_2$—$R^7$,
(e) —NR$^{17}R^7$,
(f) —CH$_2$CO$R^7$,
(g) —CH$_2$CH$_2$CO$R^7$;

Each $R^3$ is independently
(a) H,
(b) $R^{12}$,
(d) $C_{1-7}$ alkyl which is optionally partially unsaturated and is optionally substituted by one or more $R^{11}$,
(e) $C_{3-8}$ cycloalkyl which is optionally partially unsaturated and is optionally substituted by one or more $R^{11}$,
(f) aryl optionally substituted by one or more $R^8$,
(g) heteroaryl optionally substituted by one or more $R^8$, or
(h) halo; or
both $R^3$ taken together are oxo;

Each $R^4$ is independently
(a) H,
(b) halo,
(c) $OR^{12}$,
(d) OC(=O)NR$^9R^{10}$,
(e) $SR^{12}$,
(f) S(O)$_m R^{13}$,
(g) NR$^9R^{10}$,
(h) NR$^9$S(O)$_m R^{13}$,
(i) NR$^9$C(=O)OR$^{13}$,
(j) phenyl optionally substituted by one or more $R^8$,
(k) heteroaryl optionally substituted by one or more $R^8$,
(l) cyano,
(m) nitro,
(n) CONR$^9R^{10}$,
(o) CO$_2R^{12}$,
(p) C(=O)$R^{13}$,
(q) C(=NOR$^{12}$)$R^{13}$,
(r) S(O)$_m$NR$^9R^{10}$,
(s) NR$^9$C(=O)—$R^{12}$,
(t) $C_{1-7}$alkyl which is optionally partially unsaturated and is optionally substituted by one or more $R^{11}$,
(u) $C_{3-8}$cycloalkyl which is optionally partially unsaturated and is optionally substituted by one or more $R^{11}$,
(v) N$_3$,
(w) het$^1$ optionally substituted by one or more $R^8$, or
(x) C(O)O—$C_{1-4}$alkyl-$R^{12}$;

Each $R^5$ is independently,
(a) H,
(b) $C_{1-7}$alkyl which is optionally partially unsaturated and is optionally substituted by one or more $R^{11}$,
(c) $C_{3-8}$cycloalkyl which is optionally partially unsaturated and is optionally substituted by one or more $R^{11}$,
(d) aryl optionally substituted by one or more $R^8$, or
(e) heteroaryl optionally substituted by one or more $R^8$;

$R^6$ and $R^7$ are independently;
(a) $OR^{12}$,
(b) NR$^9R^{10}$,
(c) $R^{13}$, or
(e) $R^6$ and $R^7$ together with the 2 carbons to which they are attached form cyclohexane-1,3-dione optionally substituted by one or more $R^{13}$, cyclopentane-1,3-dione optionally substituted by one or more $R^{13}$, $R^6$ and $R^7$ together form —N(R$^{17}$)—S(O)$_m$—N(R$^{17}$)—, —N(R$^{17}$)—C(O)—N(R$^{17}$)—, —N(R$^{17}$)—C(S)—N(R$^{17}$)—, —N(R$^{17}$)—N(R$^{17}$)—, —N(R$^{17}$)—C(O)—, or —N(R$^{17}$)—, or $R^6$ and $R^7$ together form a phenyl ring;

$R^8$ is
(a) H,
(b) halo,
(c) $OR^{12}$,
(d) OCF$_3$,
(e) $SR^{12}$,
(f) S(O)$_m R^{13}$,
(g) NR$^9R^{10}$,
(h) NR$^9$S(O)$_m R^{13}$,
(i) NR$^9$C(=O)OR$^{13}$,
(j) phenyl optionally substituted by halo, cyano, $C_{1-7}$alkyl, or $C_{1-7}$alkoxy, in the alkyl portion of the $C_{1-7}$alkyl and $C_{1-7}$alkoxy is optionally substituted by one or more $R^{11}$;
(k) heteroaryl optionally substituted by halo, $C_{1-7}$alkyl, or $C_{1-7}$alkoxy,
(l) cyano,
(m) nitro,
(n) CONR$^9R^{10}$,
(o) CO$_2R^{12}$,
(p) C(=O)$R^{13}$,
(q) C(=NOR$^{12}$)$R^{13}$,
(r) S(O)$_m$NR$^9R^{10}$,
(s) NR$^9$C(=O)—$R^{12}$,
(t) $C_{1-7}$alkyl which is optionally partially unsaturated and is optionally substituted by one or more $R^{11}$,
(u) $C_{3-8}$cycloalkyl which is optionally partially unsaturated and is optionally substituted by one or more $R^{11}$,
(v) —C(O)H, or
(w) -het$^1$;

$R^9$ and $R^{10}$ are independently
(a) H,
(b) $OR^{12}$,
(c) aryl optionally substituted by one or more $R^{14}$,
(d) heteroaryl optionally substituted by one or more $R^{14}$,
(e) $C_{1-7}$alkyl which is optionally substituted by one or more $R^{11}$,
(f) $C_{3-8}$cycloalkyl which is optionally substituted by one or more $R^{11}$,
(g) (C=O)$R^{13}$, or
(h) $R^9$ and $R^{10}$ together with the nitrogen to which they are attached form morpholine, pyrrolidine, piperidine, thiazine, piperazine, each of the morpholine, pyrrolidine, piperidine, thiazine, piperazine being optionally substituted with $R^{11}$;

$R^{11}$ is
- (a) oxo,
- (b) phenyl optionally substituted by one or more $R^{14}$,
- (c) $OR^{12}$,
- (d) $SR^{12}$,
- (e) $NR^{12}R^{12}$,
- (f) halo,
- (g) $CO_2R^{12}$,
- (h) $CONR^{12}R^{12}$,
- (i) $C_{1-7}$alkyl which is optionally substituted oxo, halo, $OR^{12}$, $SR^{12}$, $C_{1-7}$alkyl, or $NR^{12}R^{12}$ substituents, or
- (j) $C_{3-8}$cycloalkyl which is optionally partially unsaturated and is optionally substituted by one or more oxo, halo, $OR^{12}$, $SR^{12}$, $C_{1-7}$alkyl, or $NR^{12}R^{12}$ substituents;

$R^{12}$ is
- (a) H,
- (b) $C_{1-7}$alkyl which is optionally partially unsaturated and is optionally substituted by oxo, halo, $C_{1-7}$alkyl, or $C_{1-7}$alkoxy substituents,
- (c) $C_{3-8}$cycloalkyl which is optionally partially unsaturated and is optionally substituted by one or more oxo, halo, $C_{1-7}$alkyl, or $C_{1-7}$alkoxy substituents,
- (d) aryl optionally substituted by one or more halo, $C_{1-7}$alkyl, or $C_{1-7}$alkoxy substituents, or
- (e) heteroaryl optionally substituted by one or more halo, $C_{1-7}$alkyl, or $C_{1-7}$alkoxy substituents;

$R^{13}$ is
- (a) $C_{1-7}$ alkyl which is optionally substituted by one or more oxo, halo, carboxyl, $C_{1-7}$alkyl, or $C_{1-7}$alkoxy substituents,
- (b) $C_{3-8}$cycloalkyl which is optionally partially unsaturated and is optionally substituted by one or more oxo, halo, $C_{1-7}$alkyl, or $C_{1-7}$alkoxy substituents,
- (c) aryl optionally substituted by one or more halo, $C_{1-7}$alkyl, or $C_{1-7}$alkoxy substituents;
- (d) heteroaryl optionally substituted by one or more halo, $C_{1-7}$alkyl, or $C_{1-7}$alkoxy substituents,
- (e) —C(O)OH $R^{14}$ is
- (a) H,
- (b) halo,
- (c) $C_{1-7}$alkyl,
- (d) $OR^{12}$,
- (e) $OCF_3$,
- (f) $SR^{12}$,
- (g) $S(O)_mR^{13}$,
- (h) $NR^{12}R^{12}$,
- (i) $NR^{12}S(O)_mR^{13}$,
- (j) $NR^{12}C(=O)OR^{13}$,
- (k) phenyl optionally substituted by halo, $C_{1-7}$alkyl, or $C_{1-7}$alkoxy,
- (l) heteroaryl optionally substituted by halo, $C_{1-7}$alkyl, or $C_{1-7}$alkoxy,
- (m) cyano,
- (n) nitro,
- (o) $CONR^{12}R^{12}$,
- (p) $CO_2R^{12}$,
- (q) $C(=O)R^{13}$,
- (r) $C(=NOR^{12})R^{13}$,
- (s) $S(O)_mNR^{12}R^{12}$,
- (t) $NR^9C(=O)—R^{12}$,
- (u) $C_{1-7}$alkyl which is optionally partially unsaturated and is optionally substituted by oxo, halo, $OR^{12}$, $SR^{12}$, $C_{1-7}$alkyl, or $NR^{12}R^{12}$ substituents, or
- (v) $C_{3-8}$cycloalkyl which is optionally partially unsaturated and is optionally substituted by oxo, halo, $OR^{12}$, $SR^{12}$, $C_{1-7}$alkyl, or $NR^{12}R^{12}$ substituents;

X is
—$(C(R^{15})_2)$—$NR^{16}$—$(C(R^{15})_2)$—;

Each $R^{15}$ is independently
- (a) H,
- (b) $OR^{11}$,
- (d) $C_{1-7}$ alkyl which is optionally substituted by one or more by one or more $R^{11}$ substituents,
- (e) $C_{3-8}$cycloalkyl which is optionally partially unsaturated and is optionally substituted by one or more by one or more $R^{11}$ substituents,
- (f) aryl optionally substituted by one or more $R^8$, or
- (g) heteroaryl optionally substituted by one or more $R^8$;
or both $R^{15}$ attached to the same carbon taken together are oxo;

$R^{16}$ is
- (a) H
- (b) $OR^{12}$,
- (c) $(C=O)R^{13}$,
- (d) $(C=O)OR^{13}$,
- (e) $(C=O)NR^9R^{10}$,
- (f) $S(O)_mR^{13}$,
- (g) $S(O)_mNR^9R^{10}$,
- (h) $C_{1-7}$ alkyl which is optionally substituted by one or more $R^{11}$ substituents,
- (i) $C_{3-8}$cycloalkyl which is optionally partially unsaturated and is optionally substituted by one or more $R^{11}$ substituents,
- (j) aryl optionally substituted by one or more $R^8$, or
- (k) heteroaryl optionally substituted by one or more $R^8$;

$R^{17}$ is
- (a) H,
- (b) —OH, and
- (c) $C_{1-4}$alkyl;

$R^{19}$ is
- (a) H,
- (b) $OR^{11}$,
- (c) Oxo,
- (d) $C_{1-7}$ alkyl which is optionally substituted by one or more by one or more $R^{11}$ substituents,
- (e) $C_{3-8}$cycloalkyl which is optionally partially unsaturated and is optionally substituted by one or more by one or more $R^{11}$ substituents,
- (f) aryl optionally substituted by one or more $R^8$, or
- (g) heteroaryl optionally substituted by one or more $R^8$;

$R^{20}$ is
- (a) H,
- (b) $C_{1-7}$alkyl which is optionally partially unsaturated and is optionally substituted by one or more $R^{11}$,
- (c) $C_{3-8}$cycloalkyl which is optionally partially unsaturated and is optionally substituted by one or more $R^{11}$,
- (d) aryl optionally substituted by one or more $R^8$,
- (e) heteroaryl optionally substituted by one or more $R^8$, or
- (f) $R^{20}$ and $R^{19}$, taken together, form —$CH_2$—;

wherein, "aryl" denotes a phenyl radical or an ortho-fused bicyclic carbocyclic radical having about nine to ten ring atoms in which at least one ring is aromatic;

wherein, "heteroaryl" encompasses a radical attached via a ring carbon or ring nitrogen of a monocyclic aromatic ring containing five or six ring atoms consisting of carbon and 1, 2, 3, or 4 heteroatoms, selected from oxygen (—O—), sulfur (—S—), oxygenated sulfur such as sulfinyl (S=O) and sulfonyl (S(=O)$_2$), or nitrogen N(Z) wherein Z is absent or is H, O, $C_{1-4}$alkyl, phenyl or benzyl, or a radical of an ortho-fused bicyclic heterocycle of about eight to ten ring atoms derived therefrom;

het$^1$ is a C- or N-linked five- (5), six- (6), seven- (7), or eight- (8) membered mono- or bicyclic ring, each mono- or bicyclic ring being fully saturated or partially unsaturated, and having 1-4 heteroatoms selected from the group consisting of oxygen, sulfur, and nitrogen; het$^1$ being optionally substituted by 1-2 substituents selected from $C_1$-$C_4$alkyl, amino, $C_1$-$C_4$alkylamino, $C_1$-$C_4$alkyloxy, halogen —CN, =O, =S;

each m is independently 0, 1, or 2;

provided that when each $R_4$ is H, that $R_1$ and $R_2$ are not simultaneously H, CN, or —C(O)—OCH$_3$ or that $R_1$ is not CN and $R_2$ is not —C(O)—OC$_{1-4}$alkyl;

when the compound is 1,2,4,4a-Tetrahydro-cis-2,4-dimethyl-8-nitrospiro[[1,4]oxazino[4,3-a]quinoline-5(6H), 5'(2'H)-pyrimidine]-2',4',6'(1'H,3'H)-trione that the compound is enantiomerically enriched (−) form of (2R,4S,4aS)-2,4-dimethyl-8-nitro-1,2,4,4a-tetrahydro-2'H,6H-spiro[1,4-oxazino[4,3-a]quinoline-5,5'-pyrimidine]-2',4',6'(1'H,3'H)-trione; and the compound is not 2,3,4,4a-tetrahydro-1',3'-dimethyl-spiro[1H 1-methyl pyrazino[1,2-a]quinoline-5(6H), 5'(2'H)-pyrimidine]-2'4'6'(1'H, 3'H)-trione.

2. The compound of claim 1, or a pharmaceutically acceptable salt thereof wherein each $R^4$ is independently
(a) H,
(b) halo,
(e) SR$^{12}$,
(f) S(O)$_m$R$^{13}$,
(g) NR$^9$R$^{10}$,
(h) NR$^9$S(O)$_m$R$^{13}$,
(i) NR$^9$C(=O)OR$^{13}$,
(j) phenyl optionally substituted by one or more R$^8$,
(k) heteroaryl optionally substituted by one or more R$^8$,
(l) cyano,
(m) nitro,
(n) CONR$^9$R$^{10}$,
(o) CO$_2$R$^{12}$,
(p) C(=O)R$^{13}$,
(q) C(=NOR$^{12}$)R$^{13}$,
(s) NR$^9$C(=O)—R$^{12}$,
(t) $C_{1-7}$alkyl which is optionally partially unsaturated and is optionally substituted by one or more R$^{11}$, or
(u) het$^1$ optionally substituted by one or more R$^8$.

3. The compound of claim 2, or a pharmaceutically acceptable salt thereof wherein each R$^4$ is independently selected from NO$_2$, H, Br, F, CF$_3$, CN, NH$_2$, —C(O)—OCH$_3$, —S—CH$_3$, —S(O)$_2$—CH$_3$, —N(OCH$_3$)—CH$_3$, —NH—C(O)—O-tbutyl, —NH—C(O)—CH$_3$, heteroaryl optionally substituted by one or more R$^8$, het$^1$ optionally substituted by one or more R$^8$, —S(O)$_2$—CH$_3$, or phenyl optionally substituted by one or more of NO$_2$, Cl, F, —OCH$_3$, and —OCF$_3$.

4. The compound of claim 1, or a pharmaceutically acceptable salt thereof wherein each R$^3$ is H.

5. The compound of claim 1, or a pharmaceutically acceptable salt thereof wherein R$^1$ is —C(O)R$^6$.

6. The compound of claim 1, or a pharmaceutically acceptable salt thereof wherein R$^2$ is —C(O)R$^7$.

7. The compound of claim 6, or a pharmaceutically acceptable salt thereof wherein R$^1$ is —C(O)R$^6$.

8. The compound of claim 7, or a pharmaceutically acceptable salt thereof wherein R$^6$ and R$^7$ form —N(R$^{17}$)—C(O)—N(R$^{17}$)— or —N(R$^{17}$)—C(S)—N(R$^{17}$)—.

9. The compound of claim 1, or a pharmaceutically acceptable salt thereof wherein each R$^{15}$ is independently H, $C_{1-7}$alkyl optionally substituted by one or more R$^{11}$ substituents.

10. The compound of claim 9, or a pharmaceutically acceptable salt thereof wherein X is —C(H)(C$_{1-4}$alkyl)-NR$^{16}$—C(H)(C$_{1-4}$ alkyl)-.

11. The compound of claim 1, or a pharmaceutically acceptable salt thereof wherein the compound has the formula of

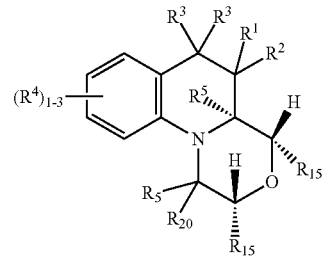

and each R$_{15}$ is independently
(b) OR$^{11}$,
(d) $C_{1-7}$ alkyl which is optionally substituted by one or more by one or more R$^{11}$ substituents,
(e) $C_{3-8}$cycloalkyl which is optionally partially unsaturated and is optionally substituted by one or more by one or more R$^{11}$ substituents,
(f) aryl optionally substituted by one or more R$^8$, or
(g) heteroaryl optionally substituted by one or more R$^8$.

12. The compound of claim 1, or a pharmaceutically acceptable salt thereof wherein the compound has the formula of

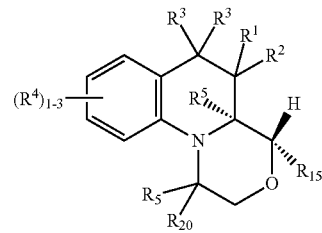

and each R$_{15}$ is independently
(b) OR$^{11}$,
(d) $C_{1-7}$ alkyl which is optionally substituted by one or more by one or more R$^{11}$ substituents,
(e) $C_{3-8}$cycloalkyl which is optionally partially unsaturated and is optionally substituted by one or more by one or more R$^{11}$ substituents,
(f) aryl optionally substituted by one or more R$^8$, or
(g) heteroaryl optionally substituted by one or more R$^8$.

13. The compound of claim 1, or a pharmaceutically acceptable salt thereof wherein R$^{16}$ is (C=O)OR$^{13}$ or $C_{1-7}$ alkyl.

14. The compound of claim 1, or a pharmaceutically acceptable salt thereof wherein each R$^5$ is independently H or $C_{1-7}$alkyl.

15. A compound selected from
8-Bromo-1,2,4,4a-tetrahydro-2,4-dimethylspiro[[1,4]piperazino[4,3-a]quinoline-5(6H), 5'(2'H)-pyrimidine]-2',4',6'(1'H,3'H)-trione;

2,3,4,4a-Tetrahydro-1',3,3'-trimethylspiro[1H-pyrazino[1,2-a]quinoline-5(6H), 5'(2'H)-pyrimidine]-2'4',6'(1'H,3'H)-trione;

2,3,4,4a-Tetrahydro-3-methylspiro[1H-pyrazino[1,2-a]quinoline-5(6H), 5'(2'H)-pyrimidine]-2',4'6'(1'H,3,H)-trione;

1,1-Dimethylethyl 1,1'2,3',4',4a,6'-octahydro-8-nitro-2',4',6'-trioxospiro[3H-pyrazino[1,2-a]quinoline-5(6H), 5'(2'H)-pyrimidine]-3-carboxylate;

1,1-Dimethylethyl-8-cyano-1,1',2,3',4,4',4a,6'-octahydro-2',4',6'-trioxospiro[3H-pyrazino[1,2-a]quinoline-5(6H), 5'(2'H)-pyrimidine]-3-carboxylate;

2,3,4,4a-Tetrahydro-3-methyl-8-nitro-2'-thioxospiro[1H-pyrazino[1,2-a]quinoline-5(6H), 5'(2'H)-pyrimidine]-4',6'(1'H,3'H)-dione);

1,2,3,3',4,4',4a,6'-Octahydro-2',4',6'-trioxospiro[1H-pyrazino[1,2-a]quinoline-5(6H), 5'(2'H)-pyrimidine-8-carbonitrile monohydrochloride; and 2,3,4,4a-Tetrahydro-8-nitrospiro[1H-pyrazino[1,2-a]quinoline-5(6H), 5'(2'H)-pyrimidine]-2',4',6'(1'H,3'H)-trione monohydrochloride.

16. The compound

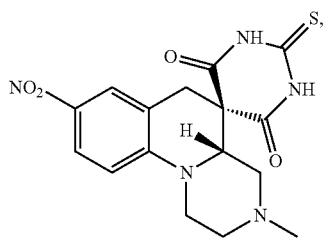

or a pharmaceutically acceptable salt thereof.

17. A method of treating a bacterial infection in a mammal, the method comprising administration of an effective amount of a compound of claim 1 or a pharmaceutically acceptable salt thereof to said mammal in need of treatment thereof.

18. The method of claim 17 wherein said compound of claim 1 or a pharmaceutically acceptable salt thereof is administered to the mammal orally, parenterally, transdermally, or topically in a pharmaceutical composition.

19. The method of claim 17 wherein said compound of claim 1 or a pharmaceutically acceptable salt thereof is administered in an amount of from about 0.1 to about 100 mg/kg of body weight/day.

20. The method of claim 17 wherein said compound of claim 1 or a pharmaceutically acceptable salt thereof is administered in an amount of from about 1 to about 50 mg/kg of body weight/day.

21. A pharmaceutical composition comprising a compound of claim 1 or a pharmaceutically acceptable salt thereof and a pharmaceutically acceptable carrier.

22. A pharmaceutical composition comprising one or more compounds of claim 1 or a pharmaceutically acceptable salt thereof and a pharmaceutically acceptable carrier.

23. The composition of claim 22 wherein the composition comprises an enantiomerically enriched form of a compound of formula I according to claim 1 or a pharmaceutically acceptable salt thereof.

24. The composition of claim 23, wherein the composition comprises at least 50% more of one enantiomer of a compound of formula I according to claim 1 relative to the other enantiomer of the compound.

25. The compositions of claim 24, wherein the composition comprises at least 80% more of one enantiomer of a compound of formula I according to claim 1 relative to the other enantiomer of the compound.

26. The compositions of claim 24, wherein the composition comprises at least 90% more of one enantiomer of a compound of formula I according to claim 1 relative to the other enantiomer of the compound.

27. The compound 2,3,4,4a-Tetrahydro-1',3,3'-trimethylspiro[1H-pyrazino[1,2-a]quinoline-5(6H), 5'(2'H)-pyrimidine]-2'4',6'(1'H,3'H)-trione; or a pharmaceutically acceptable salt thereof.

* * * * *